United States Patent [19]

Hamaguchi et al.

[11] Patent Number: 4,843,068
[45] Date of Patent: Jun. 27, 1989

[54] PYRAZOLE OXIME DERIVATIVES AND COMPOSITIONS

[75] Inventors: Hiroshi Hamaguchi, Kyoto; Hideo Takaishi; Tetsuji Ohshima, both of Nishinomiya, all of Japan; Takamichi Konno, Raleigh, N.C.; Yukio Miyagi, Osaka, Japan; Shiraiwa Yutaka, Sakai, Japan; Takayuki Akita, Yachiyo, Japan

[73] Assignee: Nihon Nohyaku Co., Ltd., Tokyo, Japan

[21] Appl. No.: 947,408

[22] Filed: Dec. 29, 1986

[30] Foreign Application Priority Data

Dec. 27, 1985 [JP] Japan .................................. 60-295759
Dec. 27, 1985 [JP] Japan .................................. 60-295760
Feb. 8, 1986 [JP] Japan .................................. 61-26582
Jun. 27, 1986 [JP] Japan .................................. 61-151187
Sep. 2, 1986 [JP] Japan .................................. 61-206442
Sep. 3, 1986 [JP] Japan .................................. 61-206993

[51] Int. Cl.$^4$ .................... A01N 43/56; A01N 55/00; C07D 231/20; C07F 7/10
[52] U.S. Cl. ................................. 514/63; 514/188; 514/189; 514/232.2; 514/236.5; 514/316; 514/326; 514/341; 514/376; 514/407; 544/64; 544/69; 544/82; 544/140; 546/14; 546/187; 546/211; 546/279; 548/103; 548/110; 548/231; 548/377

[58] Field of Search .............. 548/377, 110, 229, 103, 548/231; 514/407, 234, 326, 341, 376, 63, 188, 189, 232.2, 236.5, 316; 544/140, 64, 69, 82; 546/211, 279, 14, 187

[56] References Cited

U.S. PATENT DOCUMENTS 4,477,462 10/1984 Aoyagi ............................... 548/376

Primary Examiner—Robert W. Ramsuer
Attorney, Agent, or Firm—Cushman, Darby & Cushman

[57] ABSTRACT

A pyrazole oxime derivative represented by the general formula (I) which is useful as an insecticide and fungicide,

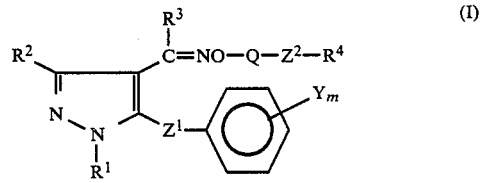

wherein the structural elements are defined in the specification, and the method of controlling said pests. The compounds represented by the general formula (I) can be synthesized by the methods disclosed in the specification.

8 Claims, No Drawings

PYRAZOLE OXIME DERIVATIVES AND COMPOSITIONS

The present invention relates to a pyrazole oxime derivative, its production and an insecticidal and acaricidal composition containing it as an active ingredient for use in agriculture and horticulture, said pyrazole oxime derivative being represented by the general formula (I),

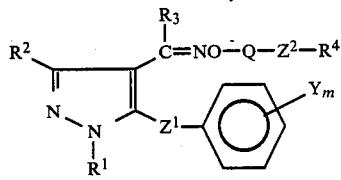

wherein $R^1$ represents $C_1$-$C_4$ alkyl or phenyl; $R^2$ represents hydrogen, $C_1$-$C_5$ alkyl, $C_1$-$C_3$ haloalkyl or phenyl; $R^3$ represents hydrogen, $C_1$-$C_4$ alkyl or phenyl; $R^4$ represents hydrogen, $C_2$-$C_4$ alkylcarbonyl, benzoyl, naphthyl or a substituent of the formula

[in which X represents hydrogen; halogen; $C_1$-$C_{12}$ alkyl; $C_1$-$C_6$ alkyl substituted with halogen, cyano, hydroxy, $C_1$-$C_5$ alkoxy or $C_2$-$C_6$ alkoxycarbonyl; $C_3$-$C_8$ cycloalkyl; cycloalkyl substituted with from one to three members selected from the group consisting of $C_1$-$C_4$ alkyl, halogen and cyano; $C_2$-$C_4$ alkenyl substituted with halogen, hydroxy, $C_2$-$C_4$ alkoxycarbonyl or $C_2$-$C_6$ alkylcarbonyl; phenyl; hydroxy; $C_1$-$C_6$ alkoxy; $C_1$-$C_4$ alkoxy substituted with halogen or $C_2$-$C_6$ alkoxycarbonyl; phenoxy which may or may not be substituted with $C_1$-$C_3$ haloalkyl; benzyloxy; $C_1$-$C_3$ alkylenedioxy formed by two adjacent Xs; pyridyloxy which may or may not be substituted with halogen or $C_1$-$C_3$ haloalkyl; a substituent of the formula, —$S(O)_pR^5$ (in which $R^5$ represents $C_1$-$C_6$ alkyl, $C_1$-$C_5$ haloalkyl or phenyl, and p represents an integer of 0, 1 or 2; cyano; formyl; nitro; a substituent of the formula —$COOR^6$ {in which $R^6$ represents hydrogen; alkali metal; $C_1$-$C_{10}$ alkyl; $C_1$-$C_5$ alkyl substituted with halogen, $C_1$-$C_4$ alkoxy, phenoxy, $C_2$-$C_4$ alkoxycarbonyl or phenoxyphenyl; $C_2$-$C_7$ alkenyl; $C_3$-$C_7$ alkynyl; $C_3$-$C_8$ cycloalkyl; $C_3$-$C_8$ cycloalkyl substituted with $C_1$-$C_3$ alkyl; phenyl; or a substituent of the formula,

(in which $R^7$, $R^8$ and $R^9$, which may be the same or different, represent $C_1$-$C_4$ alkyl or $C_3$-$C_8$ cycloalkyl)}; $C_2$-$C_6$ alkylcarbonyl; $C_2$-$C_6$ alkylcarbonyl substituted with cyano or $C_2$-$C_6$ alkylcarbonyl; benzoyl which may or may not be substituted with halogen or $C_1$-$C_6$ alkyl; $C_2$-$C_6$ alkylthiocarbonyl; $C_3$-$C_7$ alkoxycarbonylcarbonyl; a substituent of the formula,

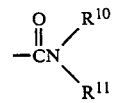

(in which $R^{10}$ and $R^{11}$, which may be the same or different, represent hydrogen, $C_1$-$C_6$ alkyl or phenyl); piperidinocarbonyl; morpholinocarbonyl which may or may not be substituted with one or two $C_1$-$C_4$ alkyls; a substituent of the formula,

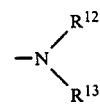

(in which $R^{12}$ represents hydrogen or $C_1$-$C_5$ alkyl, and $R^{13}$ represents formyl, $C_2$-$C_{12}$ alkoxycarbonyl, or $C_2$-$C_5$ alkoxycarbonyl substituted with halogen or $C_1$-$C_4$ alkoxy); a substituent of the formula,

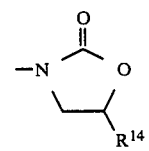

(in which $R^{14}$ represents hydrogen, $C_1$-$C_4$ alkyl or $C_2$-$C_6$ alkoxyalkyl); a substituent of the formula,

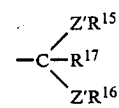

(in which $R^{15}$ and $R^{16}$, which may be the same or different, represent $C_1$-$C_4$ alkyl or, taken together, may form $C_1$-$C_4$ alkylene, $R^{17}$ represents $C_1$-$C_5$ alkyl, cyano or $C_2$-$C_6$ alkoxycarbonyl, and $Z^1$ represents oxygen or sulfur); a substituent of the formula,

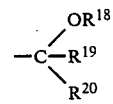

(in which $R^{18}$ represents hydrogen or $C_2$-$C_4$ alkylcarbonyl, and $R^{19}$ and $R^{20}$, which may be the same or different, represent hydrogen or $C_1$-$C_6$ alkyl); a substituent of the formula,

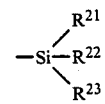

(in which $R^{21}$, $R^{22}$ and $R^{23}$, which may be the same or different, represent $C_1$-$C_4$ alkyl); or a substituent of the formula, $$-O-Si\begin{matrix}R^{24}\\-R^{25}\\R^{26}\end{matrix}$$

(in which $R^{24}$, $R^{25}$, and $R^{26}$, which may be the same or different, represent $C_1$–$C_4$ alkyl), and n represents an integer of from 1 to 5, and when n represents an integer of from 2 to 5, X may be the same or different]; Y represents hydrogen, $C_1$–$C_6$ alkyl, $C_1$–$C_4$ haloalkyl, halogen, hydroxy, $C_1$–$C_4$ alkoxy, $C_1$–$C_4$ haloalkoxy, $C_1$–$C_3$ alkylenedioxy, phenoxy which may or may not be substituted with trifluoromethyl, a substituent of the formula, $-S(O)_qR^{27}$ (in which $R^{27}$ represents $C_1$–$C_3$ alkyl and q represents an integer of 0, 1 or 2), hydroxycarbonyl, $C_2$–$C_5$ alkoxycarbonyl or a substituent of the formula $$-N\begin{matrix}R^{28}\\R^{29}\end{matrix}$$

(in which $R^{28}$ and $R^{29}$, which may be the same or different, represent hydrogen, $C_1$–$C_4$ alkyl, or benzyl which may or may not be substituted with $C_2$–$C_6$ alkoxycarbonyl); $Z^1$ represents oxygen or sulfur; $Z^2$ represents oxygen, sulfur or single bond; Q represents $C_1$–$C_8$ alkylene, $C_1$–$C_8$ alkylene substituted with halogen or phenyl, $C_3$–$C_{12}$ alkenylene, $C_3$–$C_{12}$ haloalkenylene or $C_3$–$C_6$ alkylene; and m represents an integer of from 1 to 3, and when m represents an integer of 2 or 3, Y may be the same or different.

The terms "alkyl, alkylene, alkenylene and alkynylene" as used herein mean straight-chain or branched alkyl, alkylene, alkenylene and alkynylene groups, respectively. The term "halo" means halogen such as fluorine, bromine, chlorine, etc., and the term "haloalkyl" means an alkyl group substituted with one or more halogen atoms which may be the same or different.

The compounds represented by the foregoing general formula (I) are novel compounds not described in the literatrues. They have excellent insecticidal activity against insects belonging to Lepidoptera such as diamond-back moth, cabbage armyworm, tobacco cutworm, rice stem borer, etc., insects belonging to Hemiptera such as brown planthoper, green peach aphid, etc. and mites. In addition, they have ecellent fungicidal activity against diseases of vegetables, fruit trees, flowers and ornamental plants, etc., such a rice blast, powdery mildew, downy mildew, crown rust, leaf blight, sheath blight, purple stain, etc.

Of the compounds of the present invention, those which are particularly useful as an insecticide and acaricide will be shown below:

Tert-butyl 4-[(1,3-dimethyl-5-phenoxypyrazol-4-yl)methyleneaminooxymethyl]benzoate
Tert-butyl 4-[{5-(4-fluorophenoxy)-1,3-dimethylpyrazol-4-yl}-methyleneaminooxymethyl]benzoate
Tert-pentyl 4-[(1,3-dimethyl-5-phenoxypyrazol-4-yl)methyleneaminooxymethyl]benzoate
Cyclohexyl 4-[(1,3-dimethyl-5-phenoxypyrazol-4-yl)methyleneaminooxymethyl]benzoate
1-Methylcyclohexyl 4-[1,3-dimethyl-5-phenoxypyrazol-4-yl)methyleneaminooxymethyl]benzoate
2-Chloromethyl-2-propyl 4-[(1,3-dimethyl-5-phenoxypyrazol-4-yl)methyleneaminooxymethyl]benzoate
Tert-pentyl 4-[(1-methyl-5-phenoxy-3-trifluoromethylpyrazol-4-yl)methyleneaminooxymethyl]benzoate
1,3-Dimethyl-5-phenoxypyrazole-4-carbaldehyde oxime O-4-tert-butylbenzyl ether
1,3-Dimethyl-5-phenoxypyrazole-4-carbaldehyde oxime O-4-(1-cyanocyclopentyl)benzyl ether
1,3-Dimethyl-5-phenoxypyrazole-4-carbaldehyde oxime O-4-(2,2-dichloro-1-methylcyclopropyl)benzyl ether
1,3-Dimethyl-5-phenoxypyrazole-4-carbaldehyde oxime O-4-trimethylsilylbenzyl ether
1,3-Dimethyl-5-phenoxypyrazole-4-carbaldehyde oxime O-4-(1,1,2,2-tetrafluoroethoxy)benzyl ether
1,3-Dimethyl-5-phenoxypyrazole-4-carbaldehyde oxime O-4-tert-butoxybenzyl ether
1,3-Dimethyl-5-phenoxypyrazole-4-carbaldehyde oxime O-4-(heptafluoropropylthio)benzyl ether
1,3-Dimethyl-5-phenoxypyrazole-4-carbaldehyde oxime O-4-(heptafluoropropylsulfinyl)benzyl ether
1,3-Dimethyl-5-phenoxypyrazole-4-carbaldehyde oxime O-4-(1,1,2,2-tetrafluoroethylthio)benzyl ether
N,N-diisopropyl 4-[(1,3-dimethyl-5-phenoxypyrazol-4-yl)methyleneaminooxymethyl]benzamide
Tert-butyl 4-[(1,3-dimethyl-5-phenoxypyrazol-4-yl)methyleneaminooxymethyl]phenyl ketone
2-Isopropyl-2-[4-{(1,3-dimethyl-5-phenoxypyrazol-4-yl)methyleneaminooxymethyl}phenyl]-1,3-dioxolane
2-Isopropyl-2-[4-{(1,3-dimethyl-5-phenoxypyrazol-4-yl)methyleneaminooxymethyl}phenyl]-1,3-dithiolane
Tert-butyl N-4-[(1,3-dimethyl-5-phenoxypyrazol-4-yl)methyleneaminooxymethyl]phenyl-N-ethylcarbamate
1,3-Dimethyl-5-phenoxypyrazole-4-carbaldehyde oxime O-2-(4-tert-butylphenoxy)ethyl ether Also, compounds particularly useful as a fungicide will be shown below:
Isopropyl 4-[(1,3-dimethyl-5-phenoxypyrazol-4-yl)methyleneaminooxymethyl]benzoate
Isopropyl 4-[{5-(4-fluorophenoxy)-1,3-dimethylpyrazol-4-yl}-methyleneaminooxymethyl]benzoate
1,3-Dimethyl-5-phenoxypyrazole-4-carbaldehyde oxime O-4-(methylthio)benzyl ether
1,3-Dimethyl-5-phenoxypyraxole-4-carbaldehyde oxime O-4-(difluoromethylsulfinyl)benzyl ether
N,N-dimethyl 4-[(1,3-dimethyl-5-phenoxyprazol-4-yl)methyleneaminooxymethyl]benzamide
Methyl N-4-[(1,3-dimethyl-5-phenoxypyrazol-4-yl)methyleneaminooxymethyl]phenyl-N-ethylcarbamate
5-Ethyl-3-[N'-4-{(1,3-dimethyl-5-phenoxypyrazol-4-yl)methyleneaminooxymethyl}phenyl]-2-oxazolidine The compounds represented by the general formula (I) can be synthesized, for example, by methods A, B, C and D shown below in chemical formulae.

Method A (II)

$Hal-Q-Z^2-R^4 \longrightarrow$ (III)

-continued

Method A

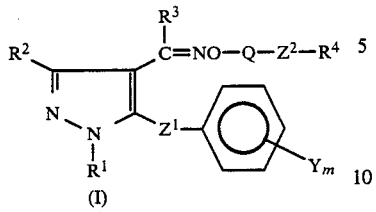

(I)

wherein $R^1$, $R^2$, $R^3$, $R^4$, Q, Y, $Z^1$, $Z^2$, m and n are as defined above, Hal represents a halogen atom and $M^1$ represents a hydrogen atom or an alkali metal atom.

The pyrazole oxime derivatives represented by the general formula (I) ca be obtained by reacting a compound of the general formula (II) what a compound of the general formula (III) in an inert solvent in the presence or absence of a base.

Solvents which can be used in the present invention may be any of those not disturbing the reaction, and include for example alcohols (e.g. isopropanol, tert-butanol, diethylene glycol), ketones (e.g. acetone, methyl ethyl ketone, cyclohexanone), ethers (e.g. diethyl ether, diisopropyl ether, tetrahydrofuran, dioxane, monoglyme, diglyme) halogenated hydrocarbons (e.g. dichloroethane, chloroform, carbon tetrachloride, tetrachloroethane), aromatic hydrocarbons (e.g. benzene, chlorobenzene, nitrobenzene, toluene), nitriles (e.g. acetonitrile), dimethyl sulfoxide, dimethylformamide and water. These solvents can be used alone or in combination. When a two-phase reaction is carried out using the solvents in combination, phase transfer catalysts such as triethylbenzylammonium chloride, trioctylmethylammonium chloride, etc. may be used.

For the base, inorganic and organic bases can be used. The inorganic bases include for example alkali or alkaline earth metal carbonates such as sodium carbonate, potassium carbonate, calcium carbonate, sodium hydrogencarbonate, etc., alkali or alkaline earth metal hydroxides such as sodium hydroxide, potassium hydroxide, calcium hydroxide, etc., and alkali metal hydrides such as lithium hydride, sodium hydride, etc.

The organic bases include for example diethylamine, triethylamine, pyridine, 4-dimethylaminopyridine, etc.

As to the amount of the base used, it suffices to use an amount equimolar to the compound represented by the general formula (II), but amounts in excess thereof will do.

The compound of the general formula (II) used in the present invention can be produced, for example, by the method described below:

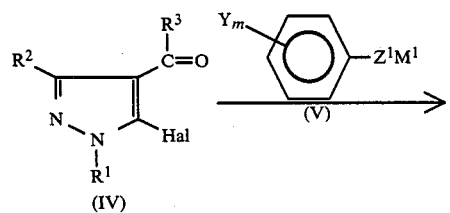

-continued

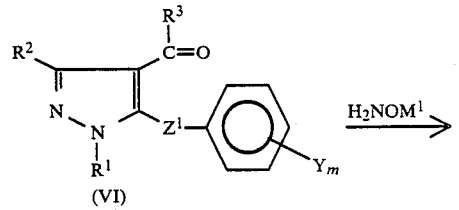

(VI)

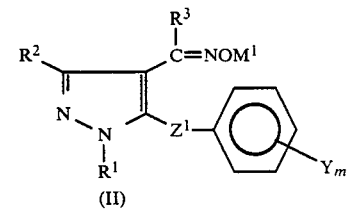

(II)

wherein $R^1$, $R^2$, $R^3$, Y, $Z^1$, m, Hal and $M^1$ are as defined above.

That is, the compound of the general formula (II) can be produced by reacting a compound of the general formula (IV) with a compound of the general formula (V) in a suitable solvent and subsequently reacting the resulting compound of the general formula (VI) with hydroxylamine.

Among the compounds represented by the general formula (III), especially when Q is methylene, $Z^2$ is a single bond and $R^4$ is substituted phenyl group, are also some novel compounds, but they can be produced in the same manner as in the case of the known compounds.

Method B

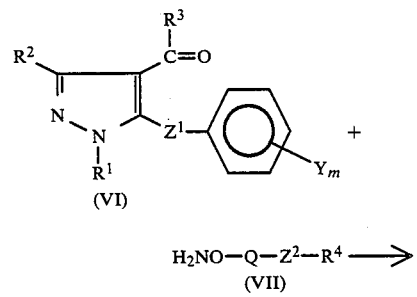

(VI)

$H_2NO-Q-Z^2-R^4 \longrightarrow$
(VII)

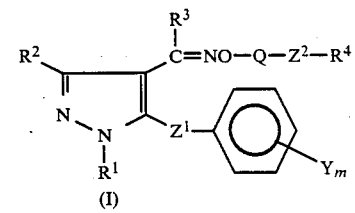

(I)

wherein $R^1$, $R^2$, $R^3$, $R^4$, Q, Y, $Z^1$, $Z^2$, m and n are as defined above.

The pyrazole oxime derivatives represented by the general formula (I) can be obtained by reacting a compound of the general formula (VI) with a compound of the general formula (VII) in an inert solvent.

For the solvent which can be used in this reaction, there are mentioned the solvents except ketones shown in Method A.

The compound represented by the general formula (VII) can be produced according to the well-known method, for example, described in Methoden der Organishen Chemie (Hougen Weyl) Band X/I Stickstoffverbindungen Teil I, P 1192.

Method C

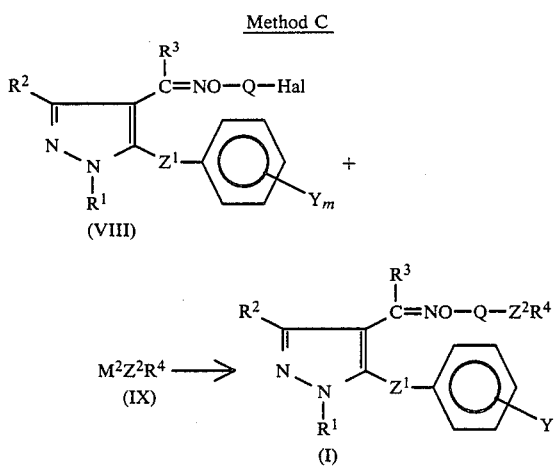

wherein $R^1$, $R^2$, $R^3$, $R^4$, Q, Y, $Z^1$, $Z^2$, m and n are as defined above, and $M^2$ represents a hydrogen atom or an alkali metal atom.

The pyrazole oxime derivatives represented by the general formula (I) can be obtained by reacting a compound of the general formula (VIII) with a compound of the general formula (IX) in an inert solvent in the presence or absence of a base.

For the solvent and base which can be used in this reaction, there are mentioned the solvents and bases shown in Method A.

Method D

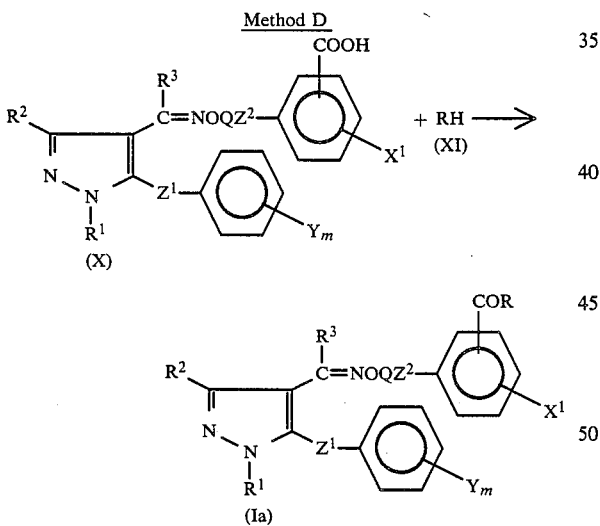

wherein $R^1$, $R^2$, $R^3$, Q, Y, $Z^1$, $Z^2$ and m are as defined above; $X^1$ represents hydrogen or $C_1$-$C_4$ alkyl; and R represents a substituent of the formula, —OW {in which W represents alkali metal; $C_1$-$C_{10}$ alkyl; alkyl substituted with halogen, $C_1$-$C_4$ alkoxy, phenoxy, $C_2$-$C_4$ alkoxycarbonyl or phenyl; $C_2$-$C_7$ alkenyl; $C_3$-$C_8$ cycloalkyl; $C_3$-$C_8$ cycloalkyl substituted with $C_1$-$C_3$ alkyl; phenyl; or a substituent of the formula,

(in which $R^7$, $R^8$, $R^9$, which may be the same or different, represent $C_1$-$C_4$ alkyl or $C_3$-$C_8$ cycloalkyl)}, a substituent of the formula,

(in which $R^{10}$ and $R^{11}$, which may be the same or different, represent hydrogen, $C_1$-$C_6$ alkyl or phenyl); piperidino; morpholino which may or may not be substituted with one or two $C_1$-$C_4$ alkyls; or $C_2$-$C_6$ alkylthio.

That is, the pyrazole oxime derivatives represented by the general formula (Ia) can be obtained by reacting a compound of the general formula (X) with a compound of the general formula (XI) in an inert solvent in the presence of a dehydrating agent. The compound (X) may be reacted with the compound (XI) after converting it to acid chloride.

Solvents which can be used in this reaction may be any of those not disturbing the reaction, and include for example ethers (e.g. diethyl ether, tetrahydrofuran, dioxane, diethylene glycol), halogenated hydrocarbons (e.g. dichloromethane, chloroform, carbon tetrachloride), dimethyl sulfoxide, dimethylformamide, etc. These solvents may be used alone or in combination.

In the methods A to D, the reaction temperature may properly be selected from a range of from room temperature to the boiling point of the solvent. The reaction time depends upon the reaction temperature and reaction scale, but it may properly be selected from a range of from 1 minute to 48 hours.

As to the molar ratio of the reagents in practicing the reaction of the present invention, they are used in equimolar amounts because this reaction is an equimolar reaction, but either one of them may be used in excess of the other.

After completion of the reaction, the desired compound can be separated by the usual methods, and if necessary, can be purified by recrystallization, column chromatography, etc.

The pyrazole oxime derivatives represented by the general formula (I) have two isomers, E-isomer and Z-isomer. In the scope of the present invention are also included the both isomers and their mixtures.

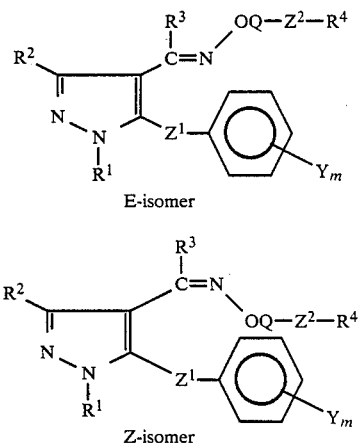

Representative examples of the pyrazole oxime derivatives represented by the general formula (I) will be shown in Table 1, but the derivatives are not limited to these examples.

TABLE 1(a)

This formula corresponds to the general formula (I) wherein Q is a methylene group, $Z^2$ is a single bond and $R^4$ is

[structure (Ib): phenyl with $X_n$ and phenyl with $Y_m$ attached to the main scaffold containing $R^1$, $R^2$, $R^3$, $Z^1$]

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 1 | $CH_3$ | $CH_3$ | H | 2-$COOCH_3$ | H | O | $n_D^{20}$ 1.5772 |
| 2 | $CH_3$ | $CH_3$ | H | 2-$COOCH_3$ | 4-F | O | $n_D^{20}$ 1.5656 |
| 3 | $CH_3$ | $CH_3$ | H | 2-$COOCH_3$ | 4-Cl | O | $n_D^{20}$ 1.5788 |
| 4 | $CH_3$ | $CH_3$ | H | 2-$COOCH_3$ | 4-$OCH_3$ | O | $n_D^{20}$ 1.5654 |
| 5 | $CH_3$ | $CH_3$ | H | 2-$COOC_4H_9$—t | H | O | $n_D^{20}$ 1.5462 |
| 6 | $CH_3$ | $CH_3$ | H | 2-$COOC_4H_9$—t | 4-F | O | $n_D^{20}$ 1.5446 |
| 7 | $CH_3$ | $CH_3$ | H | 2-$COOC_4H_9$—t | 4-$OCH_3$ | O | $n_D^{20}$ 1.5579 |
| 8 | $CH_3$ | $CH_3$ | H | 3-$COOC_4H_9$—t | H | O | $n_D^{20}$ 1.5548 |
| 9 | $CH_3$ | $CH_3$ | H | 3-$COOC_4H_9$—t | 4-F | O | $n_D^{20}$ 1.5457 |
| 10 | $CH_3$ | $CH_3$ | H | 3-$COOC_4H_9$—t | 4-$OCH_3$ | O | $n_D^{20}$ 1.5560 |
| 11 | $CH_3$ | $CH_3$ | H | 3-$COOC(CH_3)_2C_2H_5$ | H | O | $n_D^{20}$ 1.5429 |
| 12 | $CH_3$ | $CH_3$ | H | 3-$COOC(CH_3)_2C_2H_5$ | 3-F | O | $n_D^{20}$ 1.5501 |
| 13 | $CH_3$ | $CH_3$ | H | 3-$COOC(CH_3)_2C_2H_5$ | 4-$OCH_3$ | O | $n_D^{20}$ 1.5555 |
| 14 | $CH_3$ | $CH_3$ | H | 4-COOH | H | O | m.p. 183.3 |
| 15 | $CH_3$ | $CH_3$ | H | 4-COONa | H | O | $n_D^{20}$ 1.5612 |
| 16 | $CH_3$ | $CH_3$ | H | 4-$COOCH_3$ | H | O | m.p. 66.0 |
| 17 | $CH_3$ | $CH_3$ | H | 4-$COOCH_3$ | 4-F | O | $n_D^{20}$ 1.5800 |
| 18 | $CH_3$ | $CH_3$ | H | 4-$COOCH_3$ | 4-Cl | O | m.p. 55.7 |
| 19 | $CH_3$ | $CH_3$ | H | 4-$COOCH_3$ | 4-$OCH_3$ | O | $n_D^{20}$ 1.5613 |
| 20 | $CH_3$ | $CH_3$ | H | 4-$COOC_2H_5$ | H | O | $n_D^{20}$ 1.5561 |
| 21 | $CH_3$ | $CH_3$ | H | 4-$COOC_2H_5$ | 4-F | O | $n_D^{20}$ 1.5658 |
| 22 | $CH_3$ | $CH_3$ | H | 4-$COOC_2H_5$ | 4-Cl | O | $n_D^{20}$ 1.5664 |
| 23 | $CH_3$ | $CH_3$ | H | 4-$COOC_2H_5$ | 4-$OCH_3$ | O | $n_D^{20}$ 1.5660 |
| 24 | $CH_3$ | $CH_3$ | H | 4-$COOC_3H_7$—n | H | O | $n_D^{20}$ 1.5579 |
| 25 | $CH_3$ | $CH_3$ | H | 4-$COOC_3H_7$—n | 4-F | O | $n_D^{20}$ 1.5628 |
| 26 | $CH_3$ | $CH_3$ | H | 4-$COOC_3H_7$—n | 4-$OCH_3$ | O | $n_D^{20}$ 1.5321 |
| 27 | $CH_3$ | $CH_3$ | H | 4-$COOC_3H_7$—i | H | O | $n_D^{20}$ 1.5608 |
| 28 | $CH_3$ | $CH_3$ | H | 4-$COOC_3H_7$—i | 4-$CH_3$ | O | $n_D^{20}$ 1.5512 |
| 29 | $CH_3$ | $CH_3$ | H | 4-$COOC_3H_7$—i | 3-$C_2H_5$ | O | $n_D^{20}$ 1.5579 |
| 30 | $CH_3$ | $CH_3$ | H | 4-$COOC_3H_7$—i | 4-$C_2H_5$ | O | $n_D^{20}$ 1.5471 |
| 31 | $CH_3$ | $CH_3$ | H | 4-$COOC_3H_7$—i | 4-$C_4H_9$—t | O | $n_D^{20}$ 1.5523 |
| 32 | $CH_3$ | $CH_3$ | H | 4-$COOC_3H_7$—i | 2-F | O | $n_D^{20}$ 1.5531 |
| 33 | $CH_3$ | $CH_3$ | H | 4-$COOC_3H_7$—i | 3-F | O | $n_D^{20}$ 1.5541 |
| 34 | $CH_3$ | $CH_3$ | H | 4-$COOC_3H_7$—i | 4-F | O | $n_D^{20}$ 1.5610 |
| 35 | $CH_3$ | $CH_3$ | H | 4-$COOC_3H_7$—i | 3-Cl | O | $n_D^{20}$ 1.5608 |
| 36 | $CH_3$ | $CH_3$ | H | 4-$COOC_3H_7$—i | 4-Cl | O | $n_D^{20}$ 1.5640 |
| 37 | $CH_3$ | $CH_3$ | H | 4-$COOC_3H_7$—i | 2,4-$Cl_2$ | O | $n_D^{20}$ 1.5648 |
| 38 | $CH_3$ | $CH_3$ | H | 4-$COOC_3H_7$—i | 3,4-$Cl_2$ | O | $n_D^{20}$ 1.5618 |
| 39 | $CH_3$ | $CH_3$ | H | 4-$COOC_3H_7$—i | 4-Br | O | $n_D^{20}$ 1.5586 |
| 40 | $CH_3$ | $CH_3$ | H | 4-$COOC_3H_7$—i | 2-$OCH_3$ | O | $n_D^{20}$ 1.5586 |

Note: Compound 15 entry shows m.p. >300.

TABLE 1(a)-continued

This formula corresponds to the general formula (Ib) (I) wherein Q is a methylene group, $Z^2$ is a single bond and $R^4$ is —

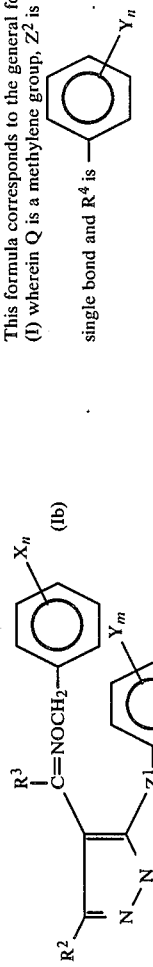

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 41 | $CH_3$ | $CH_3$ | H | 4-$COOC_3H_7$—i | 3-$OCH_3$ | O | $n_D^{20}$ 1.5585 |
| 42 | $CH_3$ | $CH_3$ | H | 4-$COOC_3H_7$—i | 4-$OCH_3$ | O | $n_D^{20}$ 1.5597 |
| 43 | $CH_3$ | $CH_3$ | H | 4-$COOC_3H_7$—i | 3,5-$(OCH_3)_2$ | O | $n_D^{20}$ 1.5621 |
| 44 | $CH_3$ | $CH_3$ | H | 4-$COOC_3H_7$—i | 4-$OC_2H_5$ | O | $n_D^{20}$ 1.5536 |
| 45 | $CH_3$ | $CH_3$ | H | 4-$COOC_3H_7$—i | 4-$SCH_3$ | O | $n_D^{20}$ 1.5819 |
| 46 | $CH_3$ | $CH_3$ | H | 4-$COOC_3H_7$—i | 4-$S(O)CH_3$ | O | $n_D^{20}$ 1.5729 |
| 47 | $CH_3$ | $CH_3$ | H | 4-$COOC_3H_7$—i | 4-$S(O)_2CH_3$ | O | $n_D^{20}$ 1.5633 |
| 48 | $CH_3$ | $CH_3$ | H | 4-$COOC_3H_7$—i | 3,4(—$OCH_2O$—) | O | $n_D^{20}$ 1.5593 |
| 49 | $CH_3$ | $CH_3$ | H | 4-$COOC_3H_7$—i | 3-$N(CH_3)_2$ | O | $n_D^{20}$ 1.5649 |
| 50 | $CH_3$ | $CH_3$ | H | 4-$COOC_4H_9$—n | H | O | $n_D^{20}$ 1.5619 |
| 51 | $CH_3$ | $CH_3$ | H | 4-$COOC_4H_9$—n | 4-F | O | $n_D^{20}$ 1.5536 |
| 52 | $CH_3$ | $CH_3$ | H | 4-$COOC_4H_9$—n | 4-Cl | O | $n_D^{20}$ 1.5629 |
| 53 | $CH_3$ | $CH_3$ | H | 4-$COOC_4H_9$—n | 4-$OCH_3$ | O | $n_D^{20}$ 1.5536 |
| 54 | $CH_3$ | $CH_3$ | H | 4-$COOC_4H_9$—s | H | O | $n_D^{20}$ 1.5602 |
| 55 | $CH_3$ | $CH_3$ | H | 4-$COOC_4H_9$—s | 4-F | O | $n_D^{20}$ 1.5541 |
| 56 | $CH_3$ | $CH_3$ | H | 4-$COOC_4H_9$—s | 4-$OCH_3$ | O | $n_D^{20}$ 1.5594 |
| 57 | $CH_3$ | $CH_3$ | H | 4-$COOC_4H_9$—i | H | O | $n_D^{20}$ 1.5629 |
| 58 | $CH_3$ | $CH_3$ | H | 4-$COOC_4H_9$—i | 4-F | O | $n_D^{20}$ 1.5561 |
| 59 | $CH_3$ | $CH_3$ | H | 4-$COOC_4H_9$—i | 4-$OCH_3$ | O | $n_D^{20}$ 1.5608 |
| 60 | $CH_3$ | $CH_3$ | H | 4-$COOC_4H_9$—t | H | O | m.p. 101.7 |
| 61 | $CH_3$ | $CH_3$ | H | 4-$COOC_4H_9$—t | 4-$CH_3$ | O | m.p. 73.0 |
| 62 | $CH_3$ | $CH_3$ | H | 4-$COOC_4H_9$—t | 3-$C_2H_5$ | O | $n_D^{20}$ 1.5542 |
| 63 | $CH_3$ | $CH_3$ | H | 4-$COOC_4H_9$—t | 4-$C_2H_5$ | O | $n_D^{20}$ 1.5440 |
| 64 | $CH_3$ | $CH_3$ | H | 4-$COOC_4H_9$—t | 4-$C_4H_9$—t | O | $n_D^{20}$ 1.5423 |
| 65 | $CH_3$ | $CH_3$ | H | 4-$COOC_4H_9$—t | 2-F | O | m.p. 92.1 |
| 66 | $CH_3$ | $CH_3$ | H | 4-$COOC_4H_9$—t | 3-F | O | m.p. 73.9 |
| 67 | $CH_3$ | $CH_3$ | H | 4-$COOC_4H_9$—t | 4-F | O | m.p. 86.8 |
| 68 | $CH_3$ | $CH_3$ | H | 4-$COOC_4H_9$—t | 3-Cl | O | $n_D^{20}$ 1.5653 |
| 69 | $CH_3$ | $CH_3$ | H | 4-$COOC_4H_9$—t | 4-Cl | O | $n_D^{20}$ 1.5632 |
| 70 | $CH_3$ | $CH_3$ | H | 4-$COOC_4H_9$—t | 4-Br | O | Paste |
| 71 | $CH_3$ | $CH_3$ | H | 4-$COOC_4H_9$—t | 3-$CF_3$ | O | $n_D^{20}$ 1.5660 |
| 72 | $CH_3$ | $CH_3$ | H | 4-$COOC_4H_9$—t | 2-$OCH_3$ | O | $n_D^{20}$ 1.5150 |
| 73 | $CH_3$ | $CH_3$ | H | 4-$COOC_4H_9$—t | 3-$OCH_3$ | O | $n_D^{20}$ 1.5663 |
| 74 | $CH_3$ | $CH_3$ | H | 4-$COOC_4H_9$—t | 4-OH | O | m.p. 72.3 |
| 75 | $CH_3$ | $CH_3$ | H | 4-$COOC_4H_9$—t | 4-$OC_2H_5$ | O | $n_D^{20}$ 1.5566 |
| 76 | $CH_3$ | $CH_3$ | H | 4-$COOC_4H_9$—t | 4-$SCH_3$ | O | m.p. 145.0 |
| 77 | $CH_3$ | $CH_3$ | H | 4-$COOC_4H_9$—t | 4-$S(O)CH_3$ | O | $n_D^{20}$ 1.5487 |
| 78 | $CH_3$ | $CH_3$ | H | 4-$COOC_4H_9$—t | 4-$S(O)_2CH_3$ | O | $n_D^{20}$ 1.5620 |
| 79 | $CH_3$ | $CH_3$ | H | 4-$COOC_4H_9$—t | 4-$CO_2C_3H_7$—n | O | $n_D^{20}$ 1.5521 |
| 80 | $CH_3$ | $CH_3$ | H | 4-$COOC_4H_9$—t | 4-$CO_2C_3H_7$—n | O | $n_D^{20}$ 1.5641 |

TABLE 1(a)-continued

This formula corresponds to the general formula (I) wherein Q is a methylene group, $Z^2$ is a single bond and $R^4$ is $$\underset{R^2}{\overset{R^3}{\underset{N-N}{\overset{C=NOCH_2}{\bigcirc}}}}\underset{Y_m}{\overset{X_n}{\bigcirc}} \quad (Ib)$$

a phenyl group $\underset{Y_n}{\bigcirc}$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 81 | $CH_3$ | $CH_3$ | H | 4-COOC$_4$H$_9$—t | 3,4(—OCH$_2$O—) | O | $n_D^{20}$ 1.5515 |
| 82 | $CH_3$ | $CH_3$ | H | 4-COOC$_4$H$_9$—t | 3-N(CH$_3$)$_2$ | O | $n_D^{20}$ 1.5538 |
| 83 | $CH_3$ | $CH_3$ | H | 4-COOC$_4$H$_9$—t | 4-NHCH$_2$—⬡—CO$_2$C$_4$H$_9$—t | O | $n_D^{20}$ 1.5605 |
| 84 | $CH_3$ | $CH_3$ | H | 4-COOC$_4$H$_9$—t | 4-N(CH$_2$—⬡—CO$_2$C$_4$H$_9$—t)$_2$ | O | $n_D^{20}$ 1.5689 |
| 85 | $CH_3$ | $CH_3$ | H | 4-COOC(CH$_3$)$_2$C$_2$H$_5$ | H | O | $n_D^{20}$ 1.5564 |
| 86 | $CH_3$ | $CH_3$ | H | 4-COOC(CH$_3$)$_2$C$_2$H$_5$ | 3-F | O | $n_D^{20}$ 1.5413 |
| 87 | $CH_3$ | $CH_3$ | H | 4-COOC(CH$_3$)$_2$C$_2$H$_5$ | 4-F | O | $n_D^{20}$ 1.5529 |
| 88 | $CH_3$ | $CH_3$ | H | 4-COOC(CH$_3$)$_2$C$_2$H$_5$ | 3-OCH$_3$ | O | $n_D^{20}$ 1.5530 |
| 89 | $CH_3$ | $CH_3$ | H | 4-COOC(CH$_3$)$_2$C$_2$H$_5$ | 4-OCH$_3$ | O | $n_D^{20}$ 1.5592 |
| 90 | $CH_3$ | $CH_3$ | H | 4-COOCH(C$_2$H$_5$)$_2$ | H | O | $n_D^{20}$ 1.5590 |
| 91 | $CH_3$ | $CH_3$ | H | 4-COOCH(C$_2$H$_5$)$_2$ | 4-F | O | $n_D^{20}$ 1.5502 |
| 92 | $CH_3$ | $CH_3$ | H | 4-COOCH(C$_2$H$_5$)$_2$ | 4-OCH$_3$ | O | $n_D^{20}$ 1.5591 |
| 93 | $CH_3$ | $CH_3$ | H | 4-COOCH$_2$C$_4$H$_9$—t | H | O | $n_D^{20}$ 1.5538 |
| 94 | $CH_3$ | $CH_3$ | H | 4-COOCH$_2$C$_4$H$_9$—t | 4-F | O | $n_D^{20}$ 1.5470 |
| 95 | $CH_3$ | $CH_3$ | H | 4-COOCH$_2$C$_4$H$_9$—t | 4-OCH$_3$ | O | $n_D^{20}$ 1.5509 |
| 96 | $CH_3$ | $CH_3$ | H | 4-COO—⬠ | H | O | $n_D^{20}$ 1.5653 |
| 97 | $CH_3$ | $CH_3$ | H | 4-COO—⬠ | 4-F | O | $n_D^{20}$ 1.5537 |

TABLE 1(a)-continued

This formula corresponds to the general formula (Ib) wherein Q is a methylene group, $Z^2$ is a single bond and $R^4$ is

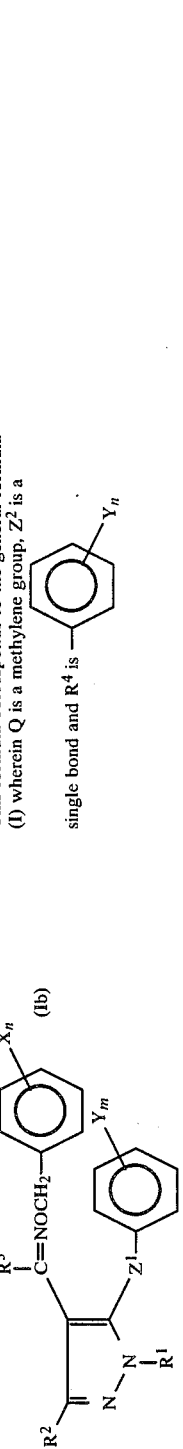

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 98 | $CH_3$ | $CH_3$ | H | 4-COO-cyclopentyl | 4-$OCH_3$ | O | $n_D^{20}$ 1.5695 |
| 99 | $CH_3$ | $CH_3$ | H | 4-COO-(1-methylcyclopentyl) | H | O | $n_D^{20}$ 1.5604 |
| 100 | $CH_3$ | $CH_3$ | H | 4-COO-(1-methylcyclopentyl) | 4-F | O | $n_D^{20}$ 1.5525 |
| 101 | $CH_3$ | $CH_3$ | H | 4-COO-(1-methylcyclopentyl) | 4-$OCH_3$ | O | $n_D^{20}$ 1.5599 |
| 102 | $CH_3$ | $CH_3$ | H | 4-COOC$(CH_3)_2$CH=$CH_2$ | H | O | $n_D^{20}$ 1.5611 |
| 103 | $CH_3$ | $CH_3$ | H | 4-COOC$(CH_3)_2$CH=$CH_2$ | 4-F | O | $n_D^{20}$ 1.5558 |
| 104 | $CH_3$ | $CH_3$ | H | 4-COOC$(CH_3)_2$CH=$CH_2$ | 4-$OCH_3$ | O | $n_D^{20}$ 1.5620 |
| 105 | $CH_3$ | $CH_3$ | H | 4-COOC$(C_2H_5)_2$C≡CH | H | O | $n_D^{20}$ 1.5633 |
| 106 | $CH_3$ | $CH_3$ | H | 4-COOC$_6H_{13}$—n | H | O | $n_D^{20}$ 1.5543 |
| 107 | $CH_3$ | $CH_3$ | H | 4-COOC$_6H_{13}$—n | 4-F | O | $n_D^{20}$ 1.5468 |
| 108 | $CH_3$ | $CH_3$ | H | 4-COOC$_6H_{13}$—n | 4-$OCH_3$ | O | $n_D^{20}$ 1.5549 |
| 109 | $CH_3$ | $CH_3$ | H | 4-COOC$(CH_3)_2$C$_3$H$_7$—i | H | O | $n_D^{20}$ 1.5525 |
| 110 | $CH_3$ | $CH_3$ | H | 4-COOC$(CH_3)_2$C$_3$H$_7$—i | 3-F | O | $n_D^{20}$ 1.5465 |
| 111 | $CH_3$ | $CH_3$ | H | 4-COOC$(CH_3)_2$C$_3$H$_7$—i | 4-F | O | $n_D^{20}$ 1.5425 |
| 112 | $CH_3$ | $CH_3$ | H | 4-COOC$(C_2H_5)_2$CH$_3$ | H | O | $n_D^{20}$ 1.5480 |
| 113 | $CH_3$ | $CH_3$ | H | 4-COOC$(C_2H_5)_2$CH$_3$ | 4-F | O | $n_D^{20}$ 1.5431 |
| 114 | $CH_3$ | $CH_3$ | H | 4-COOC$(C_2H_5)_2$CH$_3$ | 4-$OCH_3$ | O | $n_D^{20}$ 1.5540 |
| 115 | $CH_3$ | $CH_3$ | H | 4-COOCH$(CH_3)C_4H_9$—t | H | O | $n_D^{20}$ 1.5529 |
| 116 | $CH_3$ | $CH_3$ | H | 4-COOCH$(CH_3)C_4H_9$—t | 4-F | O | $n_D^{20}$ 1.5478 |
| 117 | $CH_3$ | $CH_3$ | H | 4-COOCH$(CH_3)C_4H_9$—t | 4-$OCH_3$ | O | $n_D^{20}$ 1.5509 |

TABLE 1(a)-continued

This formula corresponds to the general formula (I) wherein Q is a methylene group, $Z^2$ is a single bond and $R^4$ is

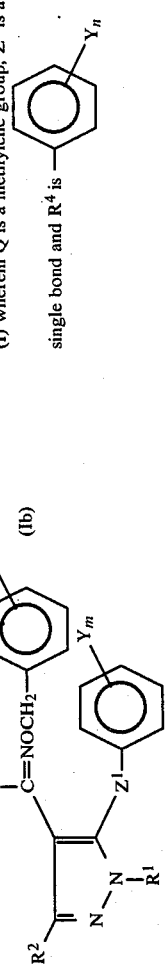

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 118 | $CH_3$ | $CH_3$ | H | 4-COO-cyclohexyl | H | O | Paste |
| 119 | $CH_3$ | $CH_3$ | H | 4-COO-cyclohexyl | 4-F | O | $n_D^{20}$ 1.5863 |
| 120 | $CH_3$ | $CH_3$ | H | 4-COO-cyclohexyl | 4-Cl | O | $n_D^{20}$ 1.5960 |
| 121 | $CH_3$ | $CH_3$ | H | 4-COO-cyclohexyl | 4-OCH$_3$ | O | $n_D^{20}$ 1.5976 |
| 122 | $CH_3$ | $CH_3$ | H | 4-COO-(1-methylcyclohexyl) | H | O | $n_D^{20}$ 1.5621 |
| 123 | $CH_3$ | $CH_3$ | H | 4-COO-(1-methylcyclohexyl) | 4-F | O | $n_D^{20}$ 1.5511 |

TABLE 1(a)-continued

This formula corresponds to the general formula (I) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 124 | CH$_3$ | CH$_3$ | H | 4-COO-(1-CH$_3$-cyclohexyl) | 4-OCH$_3$ | O | $n_D^{20}$ 1.5541 |
| 125 | CH$_3$ | CH$_3$ | H | 4-COO-(2,6-diCH$_3$-cyclohexyl) | H | O | $n_D^{20}$ 1.5584 |
| 126 | CH$_3$ | CH$_3$ | H | 4-COO-(2,6-diCH$_3$-cyclohexyl) | 4-F | O | $n_D^{20}$ 1.5370 |
| 127 | CH$_3$ | CH$_3$ | H | 4-COO-(2,6-diCH$_3$-cyclohexyl) | 4-OCH$_3$ | O | $n_D^{20}$ 1.5492 |

TABLE 1(a)-continued

This formula corresponds to the general formula (I) wherein Q is a methylene group, $Z^2$ is a single bond and $R^4$ is —[phenyl with $Y_n$]

Structure (Ib): $R^2-C(=N-N(R^1))-C(R^3)=C(-Z^1-\text{phenyl}(Y_m))-C(R^3)=NOCH_2-\text{phenyl}(X_n)$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 128 | $CH_3$ | $CH_3$ | H | 4-COO-(2-CH₃,6-iC₃H₇-cyclohexyl) | H | O | $n_D^{20}$ 1.5552 |
| 129 | $CH_3$ | $CH_3$ | H | 4-COO-(2-CH₃,6-iC₃H₇-cyclohexyl) | 4-OCH₃ | O | $n_D^{20}$ 1.5541 |
| 130 | $CH_3$ | $CH_3$ | H | 4-COOCH(C₃H₇—i)₂ | H | O | $n_D^{20}$ 1.5471 |
| 131 | $CH_3$ | $CH_3$ | H | 4-COOCH(C₃H₇—i)₂ | 4-F | O | $n_D^{20}$ 1.5400 |
| 132 | $CH_3$ | $CH_3$ | H | 4-COOCH(C₃H₇—i)₂ | 4-OCH₃ | O | $n_D^{20}$ 1.5490 |
| 133 | $CH_3$ | $CH$ | H | 4-COOC(C₂H₅)₃ | H | O | $n_D^{20}$ 1.5465 |
| 134 | $CH_3$ | $CH_3$ | H | 4-COOC(C₂H₅)₃ | 4-F | O | $n_D^{20}$ 1.5462 |
| 135 | $CH_3$ | $CH_3$ | H | 4-COOC(C₂H₅)₃ | 4-OCH₃ | O | $n_D^{20}$ 1.5518 |
| 136 | $CH_3$ | $CH_3$ | H | 4-COOCH(CH₃)-phenyl | H | O | $n_D^{20}$ 1.5730 |
| 137 | $CH_3$ | $CH_3$ | H | 4-COOCH₂-(3-phenoxyphenyl) | H | O | $n_D^{20}$ 1.5901 |

TABLE 1(a)-continued

This formula corresponds to the general formula (Ib) wherein Q is a methylene group, $Z^2$ is a single bond and $R^4$ is a phenyl group with $Y_n$ substituents.

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 138 | $CH_3$ | $CH_3$ | H | 4-$COOC_2H_4O$-phenyl | H | O | $n_D^{20}$ 1.5675 |
| 139 | $CH_3$ | $CH_3$ | H | 4-$COOC_2H_4OCH_3$ | H | O | $n_D^{20}$ 1.5672 |
| 140 | $CH_3$ | $CH_3$ | H | 4-$COOCH(CH_3)CH_2OCH_3$ | H | O | $n_D^{20}$ 1.5563 |
| 141 | $CH_3$ | $CH_3$ | H | 4-$COOC(CH_3)_2CO_2CH_3$ | H | O | $n_D^{20}$ 1.5583 |
| 142 | $CH_3$ | $CH_3$ | H | 4-$COOC_2H_4O$-phenyl | 4-F | O | $n_D^{20}$ 1.5655 |
| 143 | $CH_3$ | $CH_3$ | H | 4-$COOC_2H_4O$-phenyl | 4-Cl | O | $n_D^{20}$ 1.5685 |
| 144 | $CH_3$ | $CH_3$ | H | 4-$COOC_2H_4O$-phenyl | 4-$OCH_3$ | O | $n_D^{20}$ 1.5764 |
| 145 | $CH_3$ | $CH_3$ | H | 4-$COOC_2H_4OCH_3$ | 4-$OCH_3$ | O | $n_D^{20}$ 1.5695 |
| 146 | $CH_3$ | $CH_3$ | H | 4-$COOCH_2CF_3$ | H | O | $n_D^{20}$ 1.5491 |
| 147 | $CH_3$ | $CH_3$ | H | 4-$COOCH_2CF_3$ | 4-F | O | $n_D^{20}$ 1.5409 |
| 148 | $CH_3$ | $CH_3$ | H | 4-$COOCH_2CF_3$ | 4-Cl | O | $n_D^{20}$ 1.5450 |
| 149 | $CH_3$ | $CH_3$ | H | 4-$COOCH_2CF_3$ | 4-$OCH_3$ | O | $n_D^{20}$ 1.5459 |
| 150 | $CH_3$ | $CH_3$ | H | 4-$COOCH(CF_3)_2$ | H | O | $n_D^{20}$ 1.5563 |
| 151 | $CH_3$ | $CH_3$ | H | 4-$COOCH(CF_3)_2$ | 4-F | O | $n_D^{20}$ 1.5632 |
| 152 | $CH_3$ | $CH_3$ | H | 4-$COOC(CF_3)_2$ | 4-$OCH_3$ | O | $n_D^{20}$ 1.5664 |
| 153 | $CH_3$ | $CH_3$ | H | 4-$COOC(CH_2Cl)_2$ | H | O | $n_D^{20}$ 1.5451 |
| 154 | $CH_3$ | $CH_3$ | H | 4-$COOC(CH_3)_2CH_2Cl$ | H | O | $n_D^{20}$ 1.5662 |
| 155 | $CH_3$ | $CH_3$ | H | 4-$COOC(CH_3)_2CH_2Cl$ | 3-F | O | $n_D^{20}$ 1.5520 |
| 156 | $CH_3$ | $CH_3$ | H | 4-$COOC(CH_3)_2CH_2Cl$ | 4-F | O | $n_D^{20}$ 1.5598 |

TABLE 1(a)-continued

This formula corresponds to the general formula (I) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 157 | $CH_3$ | $CH_3$ | H | 4-COOC($CH_3$)$_2CH_2Cl$ | 3-Cl | O | $n_D^{20}$ 1.5651 |
| 158 | $CH_3$ | $CH_3$ | H | 4-COOC($CH_3$)$_2CH_2Cl$ | 4-Cl | O | $n_D^{20}$ 1.5639 |
| 159 | $CH_3$ | $CH_3$ | H | 4-COOC($CH_3$)$_2CH_2Cl$ | 3-OCH$_3$ | O | $n_D^{20}$ 1.5602 |
| 160 | $CH_3$ | $CH_3$ | H | 4-COOC($CH_3$)$_2CH_2Cl$ | 4-OCH$_3$ | O | $n_D^{20}$ 1.5665 |
| 161 | $CH_3$ | $CH_3$ | H | 4-COO—C$_6H_5$ | H | O | $n_D^{20}$ 1.5656 |
| 162 | $CH_3$ | $CH_3$ | H | 4-COOSn($C_4H_9$—n)$_3$ | H | O | $n_D^{20}$ 1.5600 |
| 163 | $CH_3$ | $CH_3$ | H | 4-COOSn(cyclohexyl)$_3$ | H | O | $n_D^{20}$ 1.5603 |
| 164 | $CH_3$ | $CF_3$ | H | 4-COOC($CH_3$)$_2C_2H_5$ | H | O | $n_D^{20}$ 1.5260 |
| 165 | $CH_3$ | $CH_3$ | $CH_3$ | 4-COOH | H | O | Paste |
| 166 | $CH_3$ | $CH_3$ | $CH_3$ | 4-COOC$_4H_9$—t | H | O | m.p. 94.4 |
| 167 | $CH_3$ | $CH_3$ | $C_2H_5$ | 4-COOC$_4H_9$—t | H | O | $n_D^{20}$ 1.5536 |
| 168 | $CH_3$ | $CH_3$ | phenyl | 4-COOC$_4H_9$—t | H | O | $n_D^{20}$ 1.5644 |
| 169 | $CH_3$ | $CH_3$ | $CH_3$ | 4-COOC($CH_3$)$_2C_2H_5$ | H | O | m.p. 60.9 |
| 170 | $CH_3$ | $CH_3$ | $CH_3$ | 4-COO—C(cyclohexyl)($CH_3$) | H | O | $n_D^{20}$ 1.5570 |
| 171 | $CH_3$ | $CH_3$ | $CH_3$ | 4-COOC($CH_3$)$_2CH_2Cl$ | H | O | $n_D^{20}$ 1.5578 |
| 172 | $CH_3$ | $C_3H_7$—i | H | 4-COOC$_3H_7$—i | H | O | $n_D^{20}$ 1.5491 |

TABLE 1(a)-continued

This formula corresponds to the general formula (I) wherein Q is a methylene group, $Z^2$ is a single bond and $R^4$ is

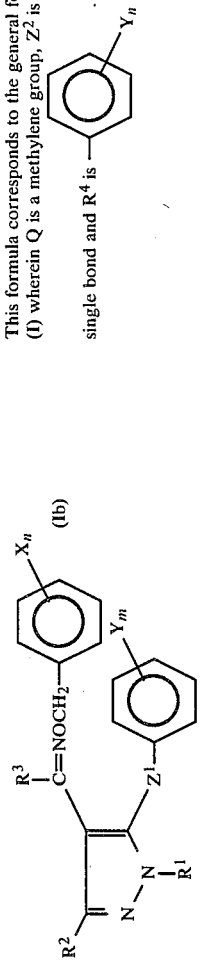

(Ib)

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 173 | $CH_3$ | H | H | 4-COOC$_4$H$_9$—t | H | O | Paste |
| 174 | $CH_3$ | $CH_3$ | H | 4-COOC$_3$H$_7$—i | H | S | $n_D^{20}$ 1.5821 |
| 175 | $CH_3$ | $CH_3$ | H | 4-COOC$_4$H$_9$—t | H | S | m.p. 112.3 |
| 176 | $CH_3$ | $CH_3$ | H | 4-COOC$_4$H$_9$—t | H | S(O) | $n_D^{20}$ 1.5649 |
| 177 | $CH_3$ | $CH_3$ | H | 4-COOC$_4$H$_9$—t | H | S(O)$_2$ | $n_D^{20}$ 1.5689 |
| 178 | $CH_3$ | $CH_3$ | H | 4-COOC$_4$H$_9$—t, 5-CH$_3$ | H | O | Paste |
| 179 | $CH_3$ | $CH_3$ | H | 4-COOC$_4$H$_9$—t, 3-CH$_3$ | H | O | Paste |
| 180 | $CH_3$ | $CH_3$ | H | 4-COOC(CH$_3$)$_2$CH$_2$F | H | O | Paste |
| 181 | $CH_3$ | $CH_3$ | H | H | 2-CH$_3$ | O | $n_D^{20}$ 1.5517 |
| 182 | $CH_3$ | $CH_3$ | H | H | 3-CH$_3$ | O | $n_D^{20}$ 1.5800 |
| 183 | $CH_3$ | $CH_3$ | H | H | 2-Cl | O | $n_D^{20}$ 1.5778 |
| 184 | $CH_3$ | $CH_3$ | H | H | 3-Cl | O | $n_D^{20}$ 1.5895 |
| 185 | $CH_3$ | $CH_3$ | H | H | 4-Cl | O | $n_D^{20}$ 1.5834 |
| 186 | $CH_3$ | $CH_3$ | H | H | 2,4-Cl$_2$ | O | $n_D^{20}$ 1.5766 |
| 187 | $CH_3$ | $CH_3$ | H | H | 4-OCH$_3$ | O | $n_D^{20}$ 1.5498 |
| 188 | $CH_3$ | $CH_3$ | H | H | | O | $n_D^{20}$ 1.5765 |
| 189 | $CH_3$ | $CH_3$ | H | H | 4-O—⟨⟩—CF$_3$ | O | $n_D^{20}$ 1.5823 |
| 190 | $CH_3$ | $CH_3$ | H | 2-CH$_3$ | H | O | $n_D^{20}$ 1.5773 |
| 191 | $CH_3$ | $CH_3$ | H | 3-CH$_3$ | H | O | $n_D^{20}$ 1.5749 |
| 192 | $CH_3$ | $CH_3$ | H | 4-CH$_3$ | H | O | $n_D^{20}$ 1.5783 |
| 193 | $CH_3$ | $CH_3$ | H | 4-CF$_3$ | H | O | $n_D^{20}$ 1.5468 |
| 194 | $CH_3$ | $CH_3$ | H | 4-CF$_3$ | 4-F | O | $n_D^{20}$ 1.5355 |
| 195 | $CH_3$ | $CH_3$ | H | 4-C$_2$H$_5$ | 4-Cl | O | $n_D^{20}$ 1.5539 |
| 196 | $CH_3$ | $CH_3$ | H | 4-C$_3$H$_7$—i | H | O | $n_D^{20}$ 1.5739 |
| 197 | $CH_3$ | $CH_3$ | H | 4-C(CH$_3$)$_2$CN | H | O | $n_D^{20}$ 1.5594 |
| 198 | $CH_3$ | $CH_3$ | H | 4-⟨▷⟩—CN | H | O | m.p. 77.4 |
| 199 | $CH_3$ | $CH_3$ | H | H | H | O | m.p. 109.1 |
| 200 | $CH_3$ | $CH_3$ | H | 4-C(CH$_3$)$_2$CN | 4-F | O | m.p. 94.7 |
| 201 | $CH_3$ | $CH_3$ | H | 4-C$_4$H$_9$—n | H | O | $n_D^{20}$ 1.5567 |
| 202 | $CH_3$ | $CH_3$ | H | 4-C$_4$H$_9$—n | 4-Cl | O | $n_D^{20}$ 1.5665 |

TABLE 1(a)-continued

This formula corresponds to the general formula (I) wherein Q is a methylene group, $Z^2$ is a single bond and $R^4$ is

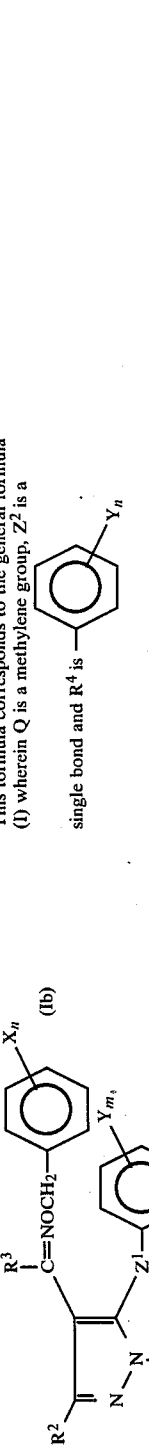

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 203 | $CH_3$ | $CH_3$ | H | $4-C_4H_9-s$ | H | O | $n_D^{20}$ 1.5631 |
| 204 | $CH_3$ | $CH_3$ | H | $4-C_4H_9-i$ | H | O | $n_D^{20}$ 1.5628 |
| 205 | $CH_3$ | $CH_3$ | H | $4-C_4H_9-t$ | H | O | $n_D^{20}$ 1.5402 |
| 206 | $CH_3$ | $CH_3$ | H | $4-C_4H_9-t$ | $3-CH_3$ | O | $n_D^{20}$ 1.5605 |
| 207 | $CH_3$ | $CH_3$ | H | $4-C_4H_9-t$ | $4-CH_3$ | O | m.p. 112.4 |
| 208 | $CH_3$ | $CH_3$ | H | $4-C_4H_9-t$ | $3-C_2H_5$ | O | $n_D^{20}$ 1.5539 |
| 209 | $CH_3$ | $CH_3$ | H | $4-C_4H_9-t$ | $4-C_2H_5$ | O | m.p. 79.0 |
| 210 | $CH_3$ | $CH_3$ | H | $4-C_4H_9-t$ | $4-C_4H_9-t$ | O | $n_D^{20}$ 1.5475 |
| 211 | $CH_3$ | $CH_3$ | H | $4-C_4H_9-t$ | 2-F | O | m.p. 67.7 |
| 212 | $CH_3$ | $CH_3$ | H | $4-C_4H_9-t$ | 3-F | O | m.p. 66.9 |
| 213 | $CH_3$ | $CH_3$ | H | $4-C_4H_9-t$ | 4-F | O | $n_D^{20}$ 1.5507 |
| 214 | $CH_3$ | $CH_3$ | H | $4-C_4H_9-t$ | 2-Cl | O | $n_D^{20}$ 1.5633 |
| 215 | $CH_3$ | $CH_3$ | H | $4-C_4H_9-t$ | 3-Cl | O | $n_D^{20}$ 1.5573 |
| 216 | $CH_3$ | $CH_3$ | H | $4-C_4H_9-t$ | 4-Cl | O | $n_D^{20}$ 1.5653 |
| 217 | $CH_3$ | $CH_3$ | H | $4-C_4H_9-t$ | 4-Br | O | $n_D^{20}$ 1.5636 |
| 218 | $CH_3$ | $CH_3$ | H | $4-C_4H_9-t$ | $3-CF_3$ | O | $n_D^{20}$ 1.5352 |
| 219 | $CH_3$ | $CH_3$ | H | $4-C_4H_9-t$ | $2-OCH_3$ | O | m.p. 76.3 |
| 220 | $CH_3$ | $CH_3$ | H | $4-C_4H_9-t$ | $3-OCH_3$ | O | $n_D^{20}$ 1.6590 |
| 221 | $CH_3$ | $CH_3$ | H | $4-C_4H_9-t$ | $4-OCH_3$ | O | $n_D^{20}$ 1.5584 |
| 222 | $CH_3$ | $CH_3$ | H | $4-C_4H_9-t$ | $3,5-(OCH_3)_2$ | O | $n_D^{20}$ 1.5535 |
| 223 | $CH_3$ | $CH_3$ | H | $4-C_4H_9-t$ | $4-OC_2H_5$ | O | $n_D^{20}$ 1.5555 |
| 224 | $CH_3$ | $CH_3$ | H | $4-C_4H_9-t$ | $4-CO_2C_3H_7-n$ | O | $n_D^{20}$ 1.5532 |
| 225 | $CH_3$ | $CH_3$ | H | $4-C_4H_9-t$ | $3,4(-OCH_2O-)$ | O | m.p. 111.4 |
| 226 | $CH_3$ | $CH_3$ | H | $4-C_4H_9-t$ | $3-N(CH_3)_2$ | O | $n_D^{20}$ 1.5858 |
| 227 | $CH_3$ | $CH_3$ | H | $4-C_4H_9-t$ | $4-N(CH_2-C_4H_9-t)_2$ | O | $n_D^{20}$ 1.5712 |
| 228 | $CH_3$ | $CH_3$ | H | $4-C_5H_{11}-n$ | H | O | $n_D^{20}$ 1.5546 |
| 229 | $CH_3$ | $CH_3$ | H | $4-CH(CH_3)C_3H_7-n$ | H | O | $n_D^{20}$ 1.5640 |
| 230 | $CH_3$ | $CH_3$ | H | $4-CH(CH_3)C_3H_7-n$ | 4-F | O | $n_D^{20}$ 1.5568 |
| 231 | $CH_3$ | $CH_3$ | H | $4-CH(CH_3)C_3H_7-n$ | 4-Cl | O | $n_D^{20}$ 1.5650 |
| 232 | $CH_3$ | $CH_3$ | H | $4-C(CH_3)_2C_2H_5$ | H | O | $n_D^{20}$ 1.5633 |
| 233 | $CH_3$ | $CH_3$ | H | $4-C(CH_3)_2C_2H_5$ | 2-F | O | $n_D^{20}$ 1.5440 |
| 234 | $CH_3$ | $CH_3$ | H | $4-C(CH_3)_2C_2H_5$ | 4-F | O | $n_D^{20}$ 1.5539 |
| 235 | $CH_3$ | $CH_3$ | H | $4-C(CH_3)_2C_2H_5$ | 4-Cl | O | $n_D^{20}$ 1.5678 |
| 236 | $CH_3$ | $CH_3$ | H | $4-C(CH_3)_2C_2H_5$ | $4-OCH_3$ | O | $n_D^{20}$ 1.5584 |

TABLE 1(a)-continued

This formula corresponds to the general formula (I) wherein Q is a methylene group, $Z^2$ is a single bond and $R^4$ is a phenyl group with $Y_n$ substituent.

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 237 | $CH_3$ | $CH_3$ | H | 1-CN-cyclopentyl (4-) | H | O | $n_D^{20}$ 1.5612 |
| 238 | $CH_3$ | $CH_3$ | H | 1-CN-cyclopentyl (4-) | 3-$OCH_3$ | O | $n_D^{20}$ 1.5632 |
| 239 | $CH_3$ | $CH_3$ | H | 4-CH(OH)$C_4H_9$—t | H | O | $n_D^{20}$ 1.5500 |
| 240 | $CH_3$ | $CH_3$ | H | 4-CH(OH)$C_4H_9$—t | 4-F | O | $n_D^{20}$ 1.5445 |
| 241 | $CH_3$ | $CH_3$ | H | 4-CH(OH)$C_4H_9$—t | 4-Cl | O | $n_D^{20}$ 1.5500 |
| 242 | $CH_3$ | $CH_3$ | H | 4-CH(OH)$C_4H_9$—t | H | O | $n_D^{20}$ 1.5545 |
| 243 | $CH_3$ | $CH_3$ | H | 4-$C_6H_{13}$—n | H | O | $n_D^{20}$ 1.5635 |
| 244 | $CH_3$ | $CH_3$ | H | 4-cyclohexyl | 2-F | O | $n_D^{20}$ 1.5591 |
| 245 | $CH_3$ | $CH_3$ | H | 4-cyclohexyl | 4-F | O | $n_D^{20}$ 1.5577 |

TABLE 1(a)-continued

This formula corresponds to the general formula (I) wherein Q is a methylene group, $Z^2$ is a single bond and $R^4$ is a 4-$Y_n$-phenyl group (Ib).

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 246 | $CH_3$ | $CH_3$ | H | 4-cyclohexyl | 4-Cl | O | $n_D^{20}$ 1.5728 |
| 247 | $CH_3$ | $CH_3$ | H | 4-cyclohexyl | 3,5-$(OCH_3)_2$ | O | $n_D^{20}$ 1.5590 |
| 248 | $CH_3$ | $CH_3$ | H | 4-(1-methylcyclohexyl) | H | O | $n_D^{20}$ 1.5656 |
| 249 | $CH_3$ | $CH_3$ | H | 4-(1,1-dimethylcyclohexyl) | 4-$OCH_3$ | O | $n_D^{20}$ 1.5596 |
| 250 | $CH_3$ | $CH_3$ | H | 4-$C_7H_{15}$—n | H | O | $n_D^{20}$ 1.5480 |
| 251 | $CH_3$ | $CH_3$ | H | 4-$C_8H_{17}$—n | H | O | $n_D^{20}$ 1.5532 |
| 252 | $CH_3$ | $CH_3$ | H | 4-phenyl | H | O | m.p. 121.7 |
| 253 | $CH_3$ | $CH_3$ | H | 4-$C(CH_3)_2OCH_3$ | H | O | $n_D^{20}$ 1.5645 |
| 254 | $CH_3$ | $CH_3$ | H | 4-$C(CH_3)_2OCH_3$ | 4-F | O | $n_D^{20}$ 1.5513 |
| 255 | $CH_3$ | $CH_3$ | H | 4-$CH=CHCOC_4H_9$—t | H | O | $n_D^{20}$ 1.5701 |
| 256 | $CH_3$ | $CH_3$ | H | 4-$CH=CHCH(OH)C_4H_9$—t | H | O | $n_D^{20}$ 1.5580 |
| 257 | $CH_3$ | $CH_3$ | H | 4-$CH=CHCOC_4H_9$—t | 4-F | O | $n_D^{20}$ 1.5526 |
| 258 | $CH_3$ | $CH_3$ | H | 4-$CH=CHCOC_4H_9$—t | 4-$OCH_3$ | O | $n_D^{20}$ 1.5576 |

TABLE 1(a)-continued

This formula corresponds to the general formula (I) wherein Q is a methylene group, $Z^2$ is a single bond and $R^4$ is a phenyl group with substituent $Y_n$ Structure (Ib):

$$R^2-C(=NOCH_2-C_6H_4-X_n)-C(R^2)=C(Z^1-C_6H_4-Y_m)-N(R^1)-N$$ (pyrazole-type with $R^3$)

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 259 | $CH_3$ | $CH_3$ | H | 4-CH=CHCO$_2$C$_2$H$_5$ | H | O | $n_D^{20}$ 1.5919 |
| 260 | $CH_3$ | $CH_3$ | H | 4-CH=CHCO$_2$C$_2$H$_5$ | 4-F | O | $n_D^{20}$ 1.5821 |
| 261 | $CH_3$ | $CH_3$ | H | 4-CH=CHCO$_2$C$_2$H$_5$ | 4-OCH$_3$ | O | $n_D^{20}$ 1.5887 |
| 262 | $CH_3$ | $CH_3$ | H | 4-CH=CBr$_2$ | H | O | m.p. 109.3 |
| 263 | $CH_3$ | $CH_3$ | H | 4-C(CH$_3$)$_2$CO$_2$C$_2$H$_5$ | H | O | $n_D^{20}$ 1.5320 |
| 264 | $CH_3$ | $CH_3$ | H | 4-C(CH$_3$)$_2$CO$_2$C$_2$H$_5$ | 4-F | O | $n_D^{20}$ 1.5502 |
| 265 | $CH_3$ | $CH_3$ | H | 4-C(CH$_3$)$_2$CO$_2$C$_3$H$_7$—i | H | O | $n_D^{20}$ 1.5492 |
| 266 | $CH_3$ | $CH_3$ | H | 4-(1-methyl-2,2-dichlorocyclopropyl) | H | O | $n_D^{20}$ 1.5680 |
| 267 | $CH_3$ | $CH_3$ | H | 4-(1-methyl-2,2-dichlorocyclopropyl) | 4-F | O | $n_D^{20}$ 1.5654 |
| 268 | $CH_3$ | $CH_3$ | H | 4-(1-methyl-2,2-dichlorocyclopropyl) | 4-Cl | O | $n_D^{20}$ 1.5660 |
| 269 | $CH_3$ | $CH_3$ | H | 4-(1-methyl-2,2-dichlorocyclopropyl) | 4-OCH$_3$ | O | $n_D^{20}$ 1.5653 |
| 270 | $CH_3$ | $CH_3$ | H | 2,4-(CH$_3$)$_2$ | 4-F | O | $n_D^{20}$ 1.5654 |
| 271 | $CH_3$ | $CH_3$ | H | 2,4-(CH$_3$)$_2$ | 4-Cl | O | $n_D^{20}$ 1.5672 |
| 272 | $CH_3$ | $CH_3$ | H | 3-OCH$_3$, 4-C$_4$H$_9$—t | H | O | $n_D^{20}$ 1.5567 |
| 273 | $CH_3$ | $CH_3$ | H | 3-OCH$_3$, 4-C$_4$H$_9$—t | 4-Cl | O | $n_D^{20}$ 1.5572 |
| 274 | $CH_3$ | $CH_3$ | H | 2,4,6-(CH$_3$)$_3$ | H | O | m.p. 94.5 |
| 275 | $CH_3$ | $CH_3$ | H | 2,6-(CH$_3$)$_2$, 4-C$_4$H$_9$—t | H | O | m.p. 111.0 |
| 276 | $CH_3$ | $CH_3$ | H | 2,6-(CH$_3$)$_2$, 4-C$_4$H$_9$—t | 4-F | O | m.p. 97.9 |
| 277 | $CH_3$ | $CH_3$ | H | 2,6-(CH$_3$)$_2$, 4-C$_4$H$_9$—t | 4-Cl | O | Paste |
| 278 | $CH_3$ | $CH_3$ | H | 2,6-(CH$_3$)$_2$, 4-C$_4$H$_9$—t | 4-OCH$_3$ | O | $n_D^{20}$ 1.5528 |
| 279 | $CH_3$ | H | H | H | 4-Cl | O | $n_D^{20}$ 1.5933 |
| 280 | $CH_3$ | H | H | 4-C$_4$H$_9$—t | H | O | $n_D^{20}$ 1.5689 |

TABLE 1(a)-continued

This formula corresponds to the general formula (Ib) wherein Q is a methylene group, $Z^2$ is a single bond and $R^4$ is —phenyl-$Y_n$ General structure (Ib): $R^2$–C(=N–N(R^1))–C(=NOCH_2–phenyl-$X_n$)(R^3) linked to $Z^1$–phenyl-$Y_m$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 281 | CH₃ | CH₃ | CH₃ | 4-C₄H₉—t | H | O | $n_D^{20}$ 1.5850 |
| 282 | CH₃ | CH₃ | C₂H₅ | 4-C₄H₉—t | H | O | $n_D^{20}$ 1.5536 |
| 283 | CH₃ | CH₃ | CH₃ | cyclohexyl (4-) | H | O | $n_D^{20}$ 1.5775 |
| 284 | CH₃ | C₂H₅ | H | 4-C₄H₉—t | H | O | m.p. 99.2 |
| 285 | CH₃ | C₃H₇—i | H | 4-C₄H₉—t | H | O | m.p. 71.5 |
| 286 | CH₃ | CH₃ | H | H | 4-Cl | O | $n_D^{20}$ 1.5966 |
| 287 | CH₃ | phenyl | H | phenyl (4-) | 4-Cl | O | $n_D^{20}$ 1.6000 |
| 288 | C₂H₅ | CH₃ | H | 4-C₄H₉—t | H | O | $n_D^{20}$ 1.5521 |
| 289 | phenyl | CH₃ | H | 4-C₄H₉—t | H | O | $n_D^{20}$ 1.5905 |
| 290 | CH₃ | CH₃ | H | H | 4-Cl | S | $n_D^{20}$ 1.5562 |
| 291 | CH₃ | CH₃ | H | 4-C(CH₃)(CO₂C₂H₅)₂ | H | S | $n_D^{20}$ 1.5760 |
| 292 | CH₃ | CH₃ | H | 4-C(CH₃)(CO₂C₂H₅)₂ | H | O | $n_D^{20}$ 1.5515 |
| 293 | CH₃ | CH₃ | H | 4-C(CH₃)(CO₂C₂H₅)₂ | 4-F | O | $n_D^{20}$ 1.5462 |
| 294 | CH₃ | CH₃ | H | 4-C(CH₃)(CO₂C₂H₅)₂ | 4-Cl | O | $n_D^{20}$ 1.5567 |
| 295 | CH₃ | CH₃ | H | 4-C(CH₃)(CO₂C₂H₅)₂ | 4-OCH₃ | O | $n_D^{20}$ 1.5553 |
| 296 | CH₃ | CH₃ | H | 4-C₄H₉—t | 4-SCH₃ | O | $n_D^{20}$ 1.5853 |
| 297 | CH₃ | CH₃ | H | 4-C₄H₉—t | 4-S(O)CH₃ | O | $n_D^{20}$ 1.5698 |

TABLE 1(a)-continued

This formula corresponds to the general formula (I) wherein Q is a methylene group, $Z^2$ is a single bond and $R^4$ is a 4-substituted phenyl group (formula Ib).

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 298 | $CH_3$ | $CH_3$ | H | 4-$C_4H_9$—t | 4-$S(O)_2CH_3$ | O | m.p. 133.6 |
| 299 | $CH_3$ | $CH_3$ | H | 4-$C(CH_3)_2CH_2F$ | H | O | Paste |
| 300 | $CH_3$ | H | H | 4-Cl | H | O | $n_D^{20}$ 1.5586 |
| 301 | $CH_3$ | H | H | 4-Cl | 4-Cl | O | $n_D^{20}$ 1.5859 |
| 302 | $CH_3$ | H | H | 4-$SCHF_2$ | H | O | $n_D^{20}$ 1.5558 |
| 303 | $CH_3$ | H | H | 4-$SCHF_2$ | 4-Cl | O | $n_D^{20}$ 1.5896 |
| 304 | $CH_3$ | H | H | 4-$S(O)CHF_2$ | H | O | $n_D^{20}$ 1.5526 |
| 305 | $CH_3$ | $CH_3$ | H | 4-F | H | O | $n_D^{20}$ 1.5681 |
| 306 | $CH_3$ | $CH_3$ | H | 4-F | 4-Cl | O | $n_D^{20}$ 1.5724 |
| 307 | $CH_3$ | $CH_3$ | H | 2,3,4,5,6-$F_5$ | H | O | $n_D^{20}$ 1.5886 |
| 308 | $CH_3$ | $CH_3$ | H | 2-Cl | H | O | $n_D^{20}$ 1.5868 |
| 309 | $CH_3$ | $CH_3$ | H | 2-Cl | 4-Cl | O | $n_D^{20}$ 1.5760 |
| 310 | $CH_3$ | $CH_3$ | H | 3-Cl | H | O | $n_D^{20}$ 1.5490 |
| 311 | $CH_3$ | $CH_3$ | H | 3-Cl | 4-Cl | O | $n_D^{20}$ 1.5820 |
| 312 | $CH_3$ | $CH_3$ | H | 4-Cl | H | O | $n_D^{20}$ 1.5750 |
| 313 | $CH_3$ | $CH_3$ | H | 4-Cl | H | S | $n_D^{20}$ 1.5563 |
| 314 | $CH_3$ | $CH_3$ | H | 4-Cl | 2-Cl | O | $n_D^{20}$ 1.5892 |
| 315 | $CH_3$ | $CH_3$ | H | 4-Cl | 3-Cl | O | $n_D^{20}$ 1.5905 |
| 316 | $CH_3$ | $CH_3$ | H | 4-Cl | 4-Cl | O | $n_D^{20}$ 1.5785 |
| 317 | $CH_3$ | $CH_3$ | H | 4-Cl | 4-Cl | S | m.p. 96.7 |
| 318 | $CH_3$ | $CH_3$ | H | 4-Cl | 4-Cl | SO | $n_D^{20}$ 1.5569 |
| 319 | $CH_3$ | $CH_3$ | H | 4-Cl | 4-Cl | $SO_2$ | $n_D^{20}$ 1.5642 |
| 320 | $CH_3$ | $CH_3$ | H | 4-Cl | 2,4-$Cl_2$ | O | m.p. 117.9 |
| 321 | $CH_3$ | $CH_3$ | H | 4-Cl | 4-$OCH_3$ | O | $n_D^{20}$ 1.5809 |
| 322 | $CH_3$ | $CH_3$ | H | 4-Cl | 4-O–C$_6$H$_4$–CF$_3$ | O | m.p. 97.8 |
| 323 | $CH_3$ | $CH_3$ | H | 2,4-$Cl_2$ | 4-Cl | O | $n_D^{20}$ 1.5811 |
| 324 | $CH_3$ | $CH_3$ | H | 3,4-$Cl_2$ | 4-Cl | O | $n_D^{20}$ 1.5958 |
| 325 | $CH_3$ | $CH_3$ | H | 2,5-$Cl_2$ | 4-Cl | O | $n_D^{20}$ 1.5826 |
| 326 | $CH_3$ | $CH_3$ | H | 3,5-$Cl_2$ | 4-Cl | O | $n_D^{20}$ 1.5778 |
| 327 | $CH_3$ | $CH_3$ | H | 2,6-$Cl_2$ | H | O | $n_D^{20}$ 1.5825 |
| 328 | $CH_3$ | $CH_3$ | H | 4-Br | 4-Cl | O | $n_D^{20}$ 1.5878 |
| 329 | $CH_3$ | $CH_3$ | H | 4-Br | 4-Cl | O | $n_D^{20}$ 1.5972 |
| 330 | $CH_3$ | $CH_3$ | H | 4-I | 4-Cl | O | $n_D^{20}$ 1.6131 |
| 331 | $CH_3$ | $CH_3$ | H | 4-CN | H | O | $n_D^{20}$ 1.5882 |

TABLE 1(a)-continued

This formula corresponds to the general formula (I) wherein Q is a methylene group, $Z^2$ is a single bond and $R^4$ is (Ib)

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 332 | CH$_3$ | CH$_3$ | H | 4-NO$_2$ | H | O | $n_D^{20}$ 1.5942 |
| 333 | CH$_3$ | CH$_3$ | H | 4-Si(CH$_3$)$_3$ | H | O | m.p. 50.8 |
| 334 | CH$_3$ | CH$_3$ | CH$_3$ | 4-Si(CH$_3$)$_3$ | H | O | m.p. 61.2 |
| 335 | CH$_3$ | CH$_3$ | H | 4-OH | H | O | m.p. >300 |
| 336 | CH$_3$ | CH$_3$ | H | 4-OCH$_3$ | H | O | $n_D^{20}$ 1.5739 |
| 337 | CH$_3$ | CH$_3$ | H | 4-OCHF$_2$ | H | O | $n_D^{20}$ 1.5422 |
| 338 | CH$_3$ | CH$_3$ | H | 4-OCHF$_2$ | H | S | $n_D^{20}$ 1.5772 |
| 339 | CH$_3$ | CH$_3$ | H | 4-OCHF$_2$ | H | SO | $n_D^{20}$ 1.5583 |
| 340 | CH$_3$ | CH$_3$ | H | 4-OCHF$_2$ | 4-CH$_3$ | O | $n_D^{20}$ 1.5745 |
| 341 | CH$_3$ | CH$_3$ | H | 4-OCHF$_2$ | 4-C$_4$H$_9$—t | O | $n_D^{20}$ 1.5396 |
| 342 | CH$_3$ | CH$_3$ | H | 4-OCHF$_2$ | 4-F | O | $n_D^{20}$ 1.5455 |
| 343 | CH$_3$ | CH$_3$ | H | 4-OCHF$_2$ | 3-Cl | O | $n_D^{20}$ 1.5630 |
| 344 | CH$_3$ | CH$_3$ | H | 4-OCHF$_2$ | 4-Cl | O | $n_D^{20}$ 1.5584 |
| 345 | CH$_3$ | CH$_3$ | H | 4-OCHF$_2$ | 3,4-Cl$_2$ | O | $n_D^{20}$ 1.5460 |
| 346 | CH$_3$ | CH$_3$ | H | 4-OCHF$_2$ | 4-OCH$_3$ | O | $n_D^{20}$ 1.5462 |
| 347 | CH$_3$ | CH$_3$ | H | 4-OCF$_3$ | H | O | $n_D^{20}$ 1.5386 |
| 348 | CH$_3$ | CH$_3$ | H | 4-OCF$_3$ | H | S | $n_D^{20}$ 1.5510 |
| 349 | CH$_3$ | CH$_3$ | H | 4-OCF$_3$ | 3-Cl | O | $n_D^{20}$ 1.5399 |
| 350 | CH$_3$ | CH$_3$ | H | 4-OCF$_3$ | 4-Cl | O | $n_D^{20}$ 1.5244 |
| 351 | CH$_3$ | CH$_3$ | H | 4-OC$_2$H$_5$ | H | O | $n_D^{20}$ 1.5736 |
| 352 | CH$_3$ | CH$_3$ | H | 4-OC$_2$H$_5$ | 4-Cl | O | $n_D^{20}$ 1.5744 |
| 353 | CH$_3$ | CH$_3$ | C$_2$H$_5$ | 4-OCF$_2$CHF$_2$ | H | O | $n_D^{20}$ 1.5287 |
| 354 | CH$_3$ | CH$_3$ | H | 4-OCF$_2$CHF$_2$ | H | O | $n_D^{20}$ 1.5252 |
| 355 | CH$_3$ | CH$_3$ | H | 4-OCF$_2$CHF$_2$ | 2-F | O | $n_D^{20}$ 1.5130 |
| 356 | CH$_3$ | CH$_3$ | H | 4-OCF$_2$CHF$_2$ | 4-F | O | $n_D^{20}$ 1.5242 |
| 357 | CH$_3$ | CH$_3$ | H | 4-OCF$_2$CHF$_2$ | 4-Cl | O | m.p. 83.8 |
| 358 | CH$_3$ | CH$_3$ | H | 4-OCF$_2$CHF$_2$ | 4-OCH$_3$ | O | $n_D^{20}$ 1.5300 |
| 359 | CH$_3$ | CH$_3$ | H | 4-OC$_3$H$_7$—i | H | O | $n_D^{20}$ 1.5686 |
| 360 | CH$_3$ | CH$_3$ | H | 4-OC$_3$H$_7$—i | 4-F | O | $n_D^{20}$ 1.5665 |
| 361 | CH$_3$ | CH$_3$ | H | 4-OC$_3$H$_7$—i | 4-Cl | O | $n_D^{20}$ 1.5689 |
| 362 | CH$_3$ | CH$_3$ | H | 4-OC$_3$H$_9$—i | 4-OCH$_3$ | O | $n_D^{20}$ 1.5642 |
| 363 | CH$_3$ | CH$_3$ | H | 4-OC$_4$H$_9$—t | H | O | $n_D^{20}$ 1.5562 |
| 364 | CH$_3$ | CH$_3$ | H | 4-OC$_4$H$_9$—t | 4-F | O | $n_D^{20}$ 1.5682 |
| 365 | CH$_3$ | CH$_3$ | H | 4-OC$_4$H$_9$—t | 4-Cl | O | m.p. 89.4 |
| 366 | CH$_3$ | CH$_3$ | H | 4-OC$_4$H$_9$—t | 4-OCH$_3$ | O | $n_D^{20}$ 1.5663 |

TABLE 1(a)-continued

This formula corresponds to the general formula (I) wherein Q is a methylene group, $Z^2$ is a single bond and $R^4$ is a 4-($Y_n$)-phenyl group (Ib):

structure: $R^2$–C(=N–N($R^1$))–C(=NOCH$_2$–C$_6$H$_4$($X_n$))–Z$^1$–C$_6$H$_4$($Y_m$) with $R^3$ on the oxime carbon

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 367 | CH$_3$ | CH$_3$ | H | 3-O-C$_6$H$_5$ | H | O | $n_D^{20}$ 1.5896 |
| 368 | CH$_3$ | CH$_3$ | H | 3-O-C$_6$H$_5$ | 2,4-Cl$_2$ | O | $n_D^{20}$ 1.5586 |
| 369 | CH$_3$ | CH$_3$ | H | 4-O-C$_6$H$_5$ | H | O | $n_D^{20}$ 1.5945 |
| 370 | CH$_3$ | CH$_3$ | H | 4-O-C$_6$H$_5$ | 4-F | O | $n_D^{20}$ 1.5852 |
| 371 | CH$_3$ | CH$_3$ | H | 4-O-C$_6$H$_5$ | 4-Cl | O | $n_D^{20}$ 1.5921 |
| 372 | CH$_3$ | CH$_3$ | H | 4-O-(3-Cl, 5-CF$_3$)-pyridin-2-yl | H | O | $n_D^{20}$ 1.5640 |
| 373 | CH$_3$ | CH$_3$ | H | 3,4(—OCH$_2$O—) | H | O | $n_D^{20}$ 1.5850 |
| 374 | CH$_3$ | CH$_3$ | H | 3,4(—OCH$_2$O—) | 4-F | O | $n_D^{20}$ 1.5750 |
| 375 | CH$_3$ | CH$_3$ | H | 3,4(—OCH$_2$O—) | 4-Cl | O | $n_D^{20}$ 1.5867 |

TABLE 1(a)-continued

This formula corresponds to the general formula (I) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 376 | CH₃ | CH₃ | H | CH₃<br>-CH-<br>4-OCHCOOC₂H₅ | H | O | $n_D^{20}$ 1.5505 |
| 377 | CH₃ | CH₃ | H | CH₃<br>-CH-<br>4-OCHCOOC₃H₇-i | H | O | $n_D^{20}$ 1.5447 |
| 378 | CH₃ | CH₃ | H | CH₃<br>-CH-<br>4-OCHCOOC₂H₅ | 4-F | O | $n_D^{20}$ 1.5560 |
| 379 | CH₃ | CH₃ | H | CH₃<br>-CH-<br>4-OCHCOOC₂H₅ | 4-Cl | O | $n_D^{20}$ 1.5600 |
| 380 | CH₃ | CH₃ | H | CH₃<br>-CH-<br>4-OCHCOOC₂H₅ | 4-OCH₃ | O | $n_D^{20}$ 1.5431 |
| 381 | CH₃ | CH₃ | H | CH₃<br>-CH-<br>4-OCHCOOC₃H₇-i | 4-OCH₃ | O | $n_D^{20}$ 1.5480 |
| 382 | CH₃ | CH₃ | H | CH₃<br>-CH-<br>4-OCHCOOC₄H₉-t | H | O | $n_D^{20}$ 1.5408 |
| 383 | CH₃ | CH₃ | H | CH₃<br>-CH-<br>4-OCHCOOC₄H₉-t | 4-F | O | $n_D^{20}$ 1.5300 |
| 384 | CH₃ | CH₃ | H | CH₃<br>-CH-<br>4-OCHCOOC₄H₉-t | 4-OCH₃ | O | $n_D^{20}$ 1.5380 |
| 385 | CH₃ | CH₃ | H | C₃H₇-i<br>-CH-<br>4-OCHCOOC₂H₅ | H | O | $n_D^{20}$ 1.5448 |

TABLE 1(a)-continued

This formula corresponds to the general formula (Ib) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 386 | $CH_3$ | $CH_3$ | H | 4-OCCOOC$_2$H$_5$ with CH$_3$/CH$_3$ | H | O | $n_D^{20}$ 1.5553 |
| 387 | $CH_3$ | $CH_3$ | H | 4-OCCOOC$_3$H$_7$—i with CH$_3$/CH$_3$ | H | O | $n_D^{20}$ 1.5522 |
| 388 | $CH_3$ | $CH_3$ | H | 4-OCH$_2$—(phenyl) | H | O | $n_D^{20}$ 1.5565 |
| 389 | $CH_3$ | $CH_3$ | H | 4-OSiC$_4$H$_9$—t with CH$_3$/CH$_3$ | H | O | $n_D^{20}$ 1.5423 |
| 390 | $CH_3$ | $CH_3$ | H | 4-SCH$_3$ | H | O | m.p. 81.8 |
| 391 | $CH_3$ | $CH_3$ | H | 4-SCH$_3$ | 4-F | O | $n_D^{20}$ 1.5930 |
| 392 | $CH_3$ | $CH_3$ | H | 4-SCH$_3$ | 4-Cl | O | $n_D^{20}$ 1.5955 |
| 393 | $CH_3$ | $CH_3$ | H | 4-SCH$_3$ | 4-OCH$_3$ | O | $n_D^{20}$ 1.5995 |
| 394 | $CH_3$ | $CH_3$ | H | 4-SOCH$_3$ | H | O | $n_D^{20}$ 1.5865 |
| 395 | $CH_3$ | $CH_3$ | H | 4-SOCH$_3$ | 4-F | O | $n_D^{20}$ 1.5700 |
| 396 | $CH_3$ | $CH_3$ | H | 4-SOCH$_3$ | 4-Cl | O | $n_D^{20}$ 1.5908 |
| 397 | $CH_3$ | $CH_3$ | H | 4-SOCH$_3$ | 4-OCH$_3$ | O | $n_D^{20}$ 1.5864 |
| 398 | $CH_3$ | $CH_3$ | H | 4-SO$_2$CH$_3$ | H | O | $n_D^{20}$ 1.5745 |
| 399 | $CH_3$ | $CH_3$ | H | 4-SO$_2$CH$_3$ | 4-F | O | $n_D^{20}$ 1.5658 |
| 400 | $CH_3$ | $CH_3$ | H | 4-SO$_2$CH$_3$ | 4-Cl | O | $n_D^{20}$ 1.5672 |
| 401 | $CH_3$ | $CH_3$ | H | 4-SO$_2$CH$_3$ | 4-OCH$_3$ | O | $n_D^{20}$ 1.5866 |
| 402 | $CH_3$ | $CH_3$ | H | 4-SC$_2$H$_5$ | H | O | $n_D^{20}$ 1.6026 |
| 403 | $CH_3$ | $CH_3$ | H | 4-SC$_2$H$_5$ | 4-F | O | $n_D^{20}$ 1.5940 |
| 404 | $CH_3$ | $CH_3$ | H | 4-SOC$_2$H$_5$ | H | O | $n_D^{20}$ 1.5899 |
| 405 | $CH_3$ | $CH_3$ | H | 4-SO$_2$C$_2$H$_5$ | 4-F | O | $n_D^{20}$ 1.5740 |
| 406 | $CH_3$ | $CH_3$ | H | 4-SO$_2$C$_2$H$_5$ | H | O | m.p. 118.9 |

TABLE 1(a)-continued

This formula corresponds to the general formula (I) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 407 | $CH_3$ | $CH_3$ | H | $4-SO_2C_2H_5$ | 4-F | O | $n_D^{20}$ 1.5891 |
| 408 | $CH_3$ | $CH_3$ | H | $2-SC_3H_7-i$, $5-CH_3$ | H | O | $n_D^{20}$ 1.5830 |
| 409 | $CH_3$ | $CH_3$ | H | $4-SC_3H_7-i$ | H | O | $n_D^{20}$ 1.5902 |
| 410 | $CH_3$ | $CH_3$ | H | $2-SC_3H_7-i$ | 4-F | O | $n_D^{20}$ 1.5872 |
| 411 | $CH_3$ | $CH_3$ | H | $4-SC_3H_7-i$ | 4-Cl | O | $n_D^{20}$ 1.5752 |
| 412 | $CH_3$ | $CH_3$ | H | $4-SC_3H_7-i$ | $4-OCH_3$ | O | $n_D^{20}$ 1.5928 |
| 413 | $CH_3$ | $CH_3$ | H | $4-SC_3H_7-i$ | H | O | $n_D^{20}$ 1.5862 |
| 414 | $CH_3$ | $CH_3$ | H | $4-SOC_3H_7-i$ | 4-F | O | $n_D^{20}$ 1.5802 |
| 415 | $CH_3$ | $CH_3$ | H | $4-SOC_3H_7-i$ | 4-Cl | O | $n_D^{20}$ 1.5669 |
| 416 | $CH_3$ | $CH_3$ | H | $4-SOC_3H_7-i$ | 4-Cl | O | $n_D^{20}$ 1.5810 |
| 417 | $CH_3$ | $CH_3$ | H | $4-SOC_3H_7-i$ | $4-OCH_3$ | O | $n_D^{20}$ 1.5748 |
| 418 | $CH_3$ | $CH_3$ | H | $4-SO_2C_3H_7-i$ | H | O | $n_D^{20}$ 1.5626 |
| 419 | $CH_3$ | $CH_3$ | H | $4-SO_2C_3H_7-i$ | 4-F | O | $n_D^{20}$ 1.5594 |
| 420 | $CH_3$ | $CH_3$ | H | $4-SO_2C_3H_7-i$ | $4-OCH_3$ | O | $n_D^{20}$ 1.5652 |
| 421 | $CH_3$ | $CH_3$ | H | $4-SC_4H_9-t$ | H | O | $n_D^{20}$ 1.5853 |
| 422 | $CH_3$ | $CH_3$ | H | $4-SCHF_2$ | H | O | $n_D^{20}$ 1.5733 |
| 423 | $CH_3$ | $CH_3$ | $CH_3$ | $4-SCHF_2$ | H | O | $n_D^{20}$ 1.6056 |
| 424 | $CH_3$ | $CH_3$ | H | $4-SCHF_2$ | H | S | $n_D^{20}$ 1.5482 |
| 425 | $C_2H_5$ | $CH_3$ | H | $4-SCHF_2$ | H | O | $n_D^{20}$ 1.5659 |
| 426 | $CH_3$ | $CH_3$ |  | $4-SCHF_2$ | H | O | $n_D^{20}$ 1.5917 |
| 427 | $CH_3$ | $CH_3$ | H | $4-SCHF_2$ | $2-CH_3$ | O | $n_D^{20}$ 1.5715 |
| 428 | $CH_3$ | $CH_3$ | H | $4-SCHF_2$ | $3-CH_3$ | O | $n_D^{20}$ 1.5741 |
| 429 | $CH_3$ | $CH_3$ | H | $4-SCHF_2$ | $4-CH_3$ | O | $n_D^{20}$ 1.5780 |
| 430 | $CH_3$ | $CH_3$ | H | $4-SCHF_2$ | $4-C_4H_9-t$ | O | $n_D^{20}$ 1.5569 |
| 431 | $CH_3$ | $CH_3$ | H | $4-SCHF_2$ | 4-F | O | $n_D^{20}$ 1.5679 |
| 432 | $CH_3$ | $CH_3$ | H | $4-SCHF_2$ | 2-Cl | O | $n_D^{20}$ 1.5750 |
| 433 | $CH_3$ | $CH_3$ | H | $4-SCHF_2$ | 3-Cl | O | $n_D^{20}$ 1.5721 |
| 434 | $CH_3$ | $CH_3$ | H | $4-SCHF_2$ | 4-Cl | O | $n_D^{20}$ 1.5395 |
| 435 | $CH_3$ | $CH_3$ | H | $4-SCHF_2$ | $3,4-Cl_2$ | O | $n_D^{20}$ 1.5852 |
| 436 | $CH_3$ | $CH_3$ | H | $4-SCHF_2$ | 4-Br | O | $n_D^{20}$ 1.5855 |
| 437 | $CH_3$ | $CH_3$ | H | $4-SCHF_2$ | $4-OCH_3$ | O | $n_D^{20}$ 1.5694 |
| 438 | $CH_3$ | $CH_3$ | H | $4-SOCHF_2$ | H | O | $n_D^{20}$ 1.5575 |
| 439 | $CH_3$ | $CH_3$ | H | $4-SOCHF_2$ | 4-F | O | Paste |
| 440 | $CH_3$ | $CH_3$ | H | $4-SOCHF_2$ | 4-Cl | O | $n_D^{20}$ 1.5748 |

TABLE 1(a)-continued

This formula corresponds to the general formula (I) wherein Q is a methylene group, $Z^2$ is a single bond and $R^4$ is a $Y_m$-substituted phenyl group.

$$\text{(Ib)}$$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 441 | CH$_3$ | CH$_3$ | H | 4-SOCHF$_2$ | 4-Br | O | $n_D^{20}$ 1.5768 |
| 442 | CH$_3$ | CH$_3$ | H | 4-SOCHF$_2$ | 4-OCH$_3$ | O | $n_D^{20}$ 1.5704 |
| 443 | CH$_3$ | CH$_3$ | H | 4-SO$_2$CHF$_2$ | H | O | $n_D^{20}$ 1.5765 |
| 444 | CH$_3$ | CH$_3$ | H | 4-SO$_2$CHF$_2$ | 4-F | O | $n_D^{20}$ 1.5500 |
| 445 | CH$_3$ | CH$_3$ | H | 4-SO$_2$CHF$_2$ | 4-Cl | O | $n_D^{20}$ 1.5612 |
| 446 | CH$_3$ | CH$_3$ | H | 4-SO$_2$CHF$_2$ | 4-Br | O | $n_D^{20}$ 1.5643 |
| 447 | CH$_3$ | CH$_3$ | H | 4-SO$_2$CHF$_2$ | 4-OCH$_3$ | O | $n_D^{20}$ 1.5597 |
| 448 | CH$_3$ | CH$_3$ | H | 4-SCF$_2$Br | H | O | $n_D^{20}$ 1.5801 |
| 449 | CH$_3$ | CH$_3$ | H | 4-SCF$_2$Br | 4-F | O | m.p. 82.3 |
| 450 | CH$_3$ | CH$_3$ | H | 4-SCF$_2$CFCl$_2$ | H | O | $n_D^{20}$ 1.5557 |
| 451 | CH$_3$ | CH$_3$ | H | 4-SCF$_2$CFCl$_2$ | 4-F | O | $n_D^{20}$ 1.5557 |
| 452 | CH$_3$ | CH$_3$ | H | 4-SCF$_2$CFCl$_2$ | 4-Cl | O | $n_D^{20}$ 1.5676 |
| 453 | CH$_3$ | CH$_3$ | H | 4-SCF$_2$CFCl$_2$ | 4-OCH$_3$ | O | $n_D^{20}$ 1.5640 |
| 454 | CH$_3$ | CH$_3$ | H | 4-SOCF$_2$CFCl$_2$ | H | O | $n_D^{20}$ 1.5889 |
| 455 | CH$_3$ | CH$_3$ | H | 4-SO$_2$CF$_2$CFCl$_2$ | H | O | $n_D^{20}$ 1.5958 |
| 456 | CH$_3$ | CH$_3$ | H | 4-SCH$_2$CF$_3$ | H | O | $n_D^{20}$ 1.5722 |
| 457 | CH$_3$ | CH$_3$ | CH$_3$ | 4-SCH$_2$CF$_3$ | 4-F | O | $n_D^{20}$ 1.5569 |
| 458 | CH$_3$ | CH$_3$ | H | 4-SCH$_2$CF$_3$ | 4-Cl | O | $n_D^{20}$ 1.5732 |
| 459 | CH$_3$ | CH$_3$ | H | 4-SCH$_2$CF$_3$ | 4-OCH$_3$ | O | $n_D^{20}$ 1.5568 |
| 460 | CH$_3$ | CH$_3$ | H | 4-SOCH$_2$CF$_3$ | 4-F | O | $n_D^{20}$ 1.5501 |
| 461 | CH$_3$ | CH$_3$ | H | 4-SOCH$_2$CF$_3$ | 4-Cl | O | $n_D^{20}$ 1.5620 |
| 462 | CH$_3$ | CH$_3$ | H | 4-SOCH$_2$CF$_3$ | 4-OCH$_3$ | O | $n_D^{20}$ 1.5518 |
| 463 | CH$_3$ | CH$_3$ | H | 4-SO$_2$CH$_2$CF$_3$ | 4-F | O | $n_D^{20}$ 1.5449 |
| 464 | CH$_3$ | CH$_3$ | H | 4-SO$_2$CH$_2$CF$_3$ | 4-Cl | O | $n_D^{20}$ 1.5497 |
| 465 | CH$_3$ | CH$_3$ | H | 4-SCF$_2$CHF$_2$ | H | O | $n_D^{20}$ 1.5527 |
| 466 | CH$_3$ | CH$_3$ | CH$_3$ | 4-SCF$_2$CHF$_2$ | H | O | $n_D^{20}$ 1.5514 |
| 467 | CH$_3$ | CH$_3$ | H | 4-SCF$_2$CHF$_2$ | 2-F | O | $n_D^{20}$ 1.5462 |
| 468 | CH$_3$ | CH$_3$ | H | 4-SCF$_2$CHF$_2$ | 3-F | O | $n_D^{20}$ 1.5450 |
| 469 | CH$_3$ | CH$_3$ | H | 4-SCF$_2$CHF$_2$ | 4-F | O | $n_D^{20}$ 1.5536 |
| 470 | CH$_3$ | CH$_3$ | H | 4-SCF$_2$CHF$_2$ | 2-Cl | O | $n_D^{20}$ 1.5540 |
| 471 | CH$_3$ | CH$_3$ | H | 4-SCF$_2$CHF$_2$ | 4-Cl | O | $n_D^{20}$ 1.5636 |
| 472 | CH$_3$ | CH$_3$ | H | 4-SCF$_2$CHF$_2$ | 2-OCH$_3$ | O | $n_D^{20}$ 1.5547 |
| 473 | CH$_3$ | CH$_3$ | H | 4-SCF$_2$CHF$_2$ | 3-OCH$_3$ | O | $n_D^{20}$ 1.5541 |
| 474 | CH$_3$ | CH$_3$ | H | 4-SCF$_2$CHF$_2$ | 4-OCH$_3$ | O | $n_D^{20}$ 1.5645 |
| 475 | CH$_3$ | CH$_3$ | H | 4-SCF$_2$CHF$_2$ | 3,5-(OCH$_3$)$_2$ | O | $n_D^{20}$ 1.5477 |
| 476 | CH$_3$ | CH$_3$ | H | 4-SOCF$_2$CHF$_2$ | H | O | $n_D^{20}$ 1.5865 |
| 477 | CH$_3$ | CH$_3$ | H | 4-SOCF$_2$CHF$_2$ | 4-F | O | $n_D^{20}$ 1.5684 |
| 478 | CH$_3$ | CH$_3$ | H | 4-SOCF$_2$CHF$_2$ | 4-Cl | O | $n_D^{20}$ 1.5498 |
| 479 | CH$_3$ | CH$_3$ | H | 4-SOCF$_2$CHF$_2$ | 4-OCH$_3$ | O | $n_D^{20}$ 1.5786 |
| 480 | CH$_3$ | CH$_3$ | H | 4-SO$_2$CF$_2$CHF$_2$ | 4-F | O | Paste |

TABLE 1(a)-continued

This formula corresponds to the general formula (Ib) wherein Q is a methylene group, $Z^2$ is a single bond and $R^4$ is a phenyl group with $Y_n$ substituent.

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 481 | $CH_3$ | $CH_3$ | H | $4\text{-}SO_2CF_2CHF_2$ | H | O | Paste |
| 482 | $CH_3$ | $CH_3$ | H | $4\text{-}SO_2CF_2CHF_2$ | 4-Cl | O | $n_D^{20}$ 1.5420 |
| 483 | $CH_3$ | $CH_3$ | H | $4\text{-}SO_2CF_2CHF_2$ | 4-OCH$_3$ | O | $n_D^{20}$ 1.5890 |
| 484 | $CH_3$ | $CH_3$ | H | $4\text{-}SCF_2CF_2Br$ | H | O | $n_D^{20}$ 1.5632 |
| 485 | $CH_3$ | $CH_3$ | H | $4\text{-}SCF_2CF_2Br$ | 4-F | O | $n_D^{20}$ 1.5585 |
| 486 | $CH_3$ | $CH_3$ | H | $4\text{-}SCF_2CF_2Br$ | 4-Cl | O | $n_D^{20}$ 1.5655 |
| 487 | $CH_3$ | $CH_3$ | H | $4\text{-}SCF_2CF_2Br$ | 4-OCH$_3$ | O | $n_D^{20}$ 1.5622 |
| 488 | $CH_3$ | $CH_3$ | H | $4\text{-}SOCF_2CF_2Br$ | H | O | $n_D^{20}$ 1.5680 |
| 489 | $CH_3$ | $CH_3$ | H | $4\text{-}SOCF_2CF_2Br$ | 4-F | O | $n_D^{20}$ 1.5503 |
| 490 | $CH_3$ | $CH_3$ | H | $4\text{-}SO_2CF_2CF_2Br$ | 4-F | O | $n_D^{20}$ 1.5686 |
| 491 | $CH_3$ | $CH_3$ | H | $4\text{-}SOCF_2CF_2Br$ | 4-Cl | O | $n_D^{20}$ 1.5611 |
| 492 | $CH_3$ | $CH_3$ | H | $4\text{-}SOCF_2CF_2Br$ | 4-OCH$_3$ | O | $n_D^{20}$ 1.5588 |
| 493 | $CH_3$ | $CH_3$ | $CH_3$ | $4\text{-}SC_3F_7$ | H | O | $n_D^{20}$ 1.5250 |
| 494 | $CH_3$ | $CH_3$ | H | $4\text{-}SC_3F_7$ | H | O | $n_D^{20}$ 1.5217 |
| 495 | $CH_3$ | $CH_3$ | H | $4\text{-}SC_3F_7$ | 4-CH$_3$ | O | $n_D^{20}$ 1.5228 |
| 496 | $CH_3$ | $CH_3$ | H | $4\text{-}SC_3F_7$ | 3-F | O | $n_D^{20}$ 1.5172 |
| 497 | $CH_3$ | $CH_3$ | H | $4\text{-}SC_3F_7$ | 4-F | O | $n_D^{20}$ 1.5175 |
| 498 | $CH_3$ | $CH_3$ | H | $4\text{-}SC_3F_7$ | 3-Cl | O | $n_D^{20}$ 1.5298 |
| 499 | $CH_3$ | $CH_3$ | H | $4\text{-}SC_3F_7$ | 4-Cl | O | Paste |
| 500 | $CH_3$ | $CH_3$ | H | $4\text{-}SC_3F_7$ | 3-CF$_3$ | O | $n_D^{20}$ 1.5020 |
| 501 | $CH_3$ | $CH_3$ | H | $4\text{-}SC_3F_7$ | 3-OCH$_3$ | O | $n_D^{20}$ 1.5263 |
| 502 | $CH_3$ | $CH_3$ | H | $4\text{-}SC_3F_7$ | 4-OCH$_3$ | O | $n_D^{20}$ 1.5137 |
| 503 | $CH_3$ | $CH_3$ | H | $4\text{-}SOC_3F_7$ | H | O | $n_D^{20}$ 1.5289 |
| 504 | $CH_3$ | $CH_3$ | H | $4\text{-}SOC_3F_7$ | 4-F | O | Paste |
| 505 | $CH_3$ | $CH_3$ | H | $4\text{-}SOC_3F_7$ | 4-F | O | Paste |
| 506 | $CH_3$ | $CH_3$ | H | 4-S-phenyl | H | O | $n_D^{20}$ 1.6134 |
| 507 | $CH_3$ | $CH_3$ | H | 4-SO-phenyl | H | O | $n_D^{20}$ 1.5980 |

TABLE 1(a)-continued

This formula corresponds to the general formula (I) wherein Q is a methylene group, $Z^2$ is a single bond and $R^4$ is

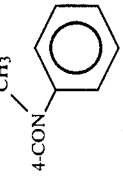

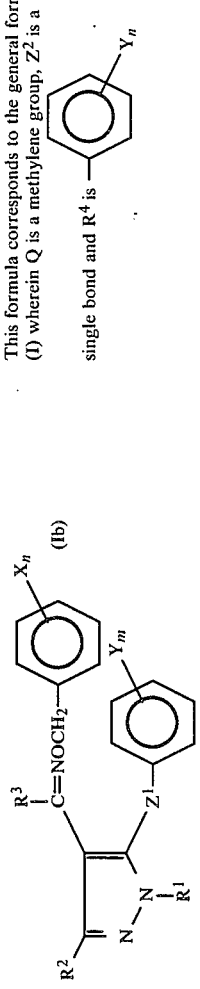

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 508 | $CH_3$ | $CH_3$ | H | $4\text{-}SO_2\text{-}$ | H | O | $n_D^{20}$ 1.5940 |
| 509 | $CH_3$ | $CH_3$ | H | 4-Cl | 4-Cl | O | $n_D^{20}$ 1.6052 |
| 510 | $CH_3$ | $CH_3$ | H | 4-SOCHF$_2$ | 4-Cl | O | $n_D^{20}$ 1.5643 |
| 511 | $CH_3$ | $CH_3$ | H | 4-SCF$_3$ | H | O | $n_D^{20}$ 1.5320 |
| 512 | $CH_3$ | $CH_3$ | H | 4-SOCF$_3$ | H | O | $n_D^{20}$ 1.5324 |
| 513 | $CH_3$ | $CH_3$ | H | 4-SO$_2$CF$_3$ | H | O | $n_D^{20}$ 1.5876 |
| 514 | $CH_3$ | $CH_3$ | H | 4-SC$_3$F$_7$ | 4-OCHF$_2$ | O | $n_D^{20}$ 1.5235 |
| 515 | $CH_3$ | $CH_3$ | H | 4-SC$_3$F$_7$ | 4-OCF$_3$ | O | $n_D^{20}$ 1.5201 |
| 516 | $CH_3$ | $CH_3$ | H | 4-COSC$_2$H$_5$ | H | O | $n_D^{20}$ 1.5889 |
| 517 | $CH_3$ | $CH_3$ | H | 4-COSC$_3$H$_7$—i | H | O | $n_D^{20}$ 1.5812 |
| 518 | $CH_3$ | $CH_3$ | H | 4-COSC$_3$H$_7$—t | H | O | $n_D^{20}$ 1.5896 |
| 519 | $CH_3$ | $CH_3$ | H | 4-COSC$_4$H$_9$—t | H | O | Crystal |
| 520 | $CH_3$ | $CH_3$ | H | 4-CONHCH$_3$ | 4-F | O | $n_D^{20}$ 1.5576 |
| 521 | $CH_3$ | $CH_3$ | H | 4-CONHC$_3$H$_7$—i | H | O | m.p. 94.4 |
| 522 | $CH_3$ | $CH_3$ | H | 4-CONHC$_3$H$_7$—i | 4-F | O | m.p. 136.4 |
| 523 | $CH_3$ | $CH_3$ | H | 4-CONHC$_4$H$_9$—t | H | O | m.p. 106.7 |
| 524 | $CH_3$ | $CH_3$ | H | 4-CONHC$_4$H$_9$—t | 4-F | O | $n_D^{20}$ 1.5582 |
| 525 | $CH_3$ | $CH_3$ | H | 4-CONHC$_4$H$_9$—t | 4-OCH$_3$ | O | $n_D^{20}$ 1.5662 |
| 526 | $CH_3$ | $CH_3$ | H | 4-CON(CH$_3$)$_2$ | H | O | $n_D^{20}$ 1.5808 |
| 527 | $CH_3$ | $CH_3$ | H | 4-CON(C$_3$H$_7$—i)$_2$ | H | O | $n_D^{20}$ 1.5263 |
| 528 | $CH_3$ | $CH_3$ | H | 4-CON(C$_3$H$_7$—i)$_2$ | 4-F | O | $n_D^{20}$ 1.5245 |
| 529 | $CH_3$ | $CH_3$ | H | 4-CON(C$_3$H$_7$—i)$_2$ | 4-Cl | O | $n_D^{20}$ 1.5326 |
| 530 | $CH_3$ | $CH_3$ | H | 4-CON(C$_3$H$_7$—i)$_2$ | 4-OCH$_3$ | O | $n_D^{20}$ 1.5328 |
| 531 | $CH_3$ | $CH_3$ | H | 4-CON(CH$_3$)(CH$_2$C$_6$H$_5$) | H | O | $n_D^{20}$ 1.5803 |

TABLE 1(a)-continued

This formula corresponds to the general formula (I) wherein Q is a methylene group, $Z^2$ is a single bond and $R^4$ is

[structure: phenyl with $Y_n$ substituent]

[general structure shown: $R^2-C(=N-N-R^1)-C(R^3)=NOCH_2$ connected to phenyl($X_n$) and phenyl($Y_m$)-$Z^1$]

(Ib)

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 532 | CH$_3$ | CH$_3$ | H | 4-CON(piperidine) | H | O | $n_D^{20}$ 1.5689 |
| 533 | CH$_3$ | CH$_3$ | H | 4-CON(piperidine) | 4-F | O | $n_D^{20}$ 1.5755 |
| 534 | CH$_3$ | CH$_3$ | H | 4-CON(piperidine) | 4-Cl | O | $n_D^{20}$ 1.5657 |
| 535 | CH$_3$ | CH$_3$ | H | 4-CON(piperidine) | 4-OCH$_3$ | O | Paste |
| 536 | CH$_3$ | CH$_3$ | H | 4-CON(morpholine) | H | O | $n_D^{20}$ 1.5632 |
| 537 | CH$_3$ | CH$_3$ | H | 4-CON(morpholine) | 4-F | O | $n_D^{20}$ 1.5600 |

TABLE 1(a)-continued

This formula corresponds to the general formula (Ib) wherein Q is a methylene group, $Z^2$ is a single bond and $R^4$ is a phenyl group with $Y_n$ substituent.

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 538 | CH$_3$ | CH$_3$ | H | 4-CON(morpholino) | 4-OCH$_3$ | O | $n_D^{20}$ 1.5498 |
| 539 | CH$_3$ | CH$_3$ | H | 4-CON(2,6-dimethylmorpholino) | H | O | $n_D^{20}$ 1.5617 |
| 540 | CH$_3$ | CH$_3$ | H | 4-CON(2,6-dimethylmorpholino) | 4-F | O | n 1.5643 |
| 541 | CH$_3$ | CH$_3$ | H | 4-COCH$_3$ | H | O | m.p. 88.0 |
| 542 | CH$_3$ | CH$_3$ | H | 4-COCOOC$_2$H$_5$ | H | O | $n_D^{20}$ 1.5709 |
| 543 | CH$_3$ | CH$_3$ | H | 4-COCOOC$_3$H$_7$—i | H | O | $n_D^{20}$ 1.5756 |
| 544 | CH$_3$ | CH$_3$ | H | 4-COC$_2$H$_5$ | 4-F | O | m.p. 59.0 |
| 545 | CH$_3$ | CH$_3$ | H | 4-COC$_2$H$_5$ | H | O | $n_D^{20}$ 1.5664 |
| 546 | CH$_3$ | CH$_3$ | H | 4-COC$_3$H$_7$—i | H | O | $n_D^{20}$ 1.5705 |
| 547 | CH$_3$ | CH$_3$ | H | 4-COC$_4$H$_9$—t | H | O | $n_D^{20}$ 1.5853 |
| 548 | CH$_3$ | CH$_3$ | H | 4-COC$_4$H$_9$—t | 4-F | O | $n_D^{20}$ 1.5567 |
| 549 | CH$_3$ | CH$_3$ | H | 4-COC$_4$H$_9$—t | 4-Cl | O | $n_D^{20}$ 1.5896 |
| 550 | CH$_3$ | CH$_3$ | H | 4-CO—C(CH$_3$)$_2$—CN | H | O | $n_D^{20}$ 1.5865 |

TABLE 1(a)-continued

This formula corresponds to the general formula (I) wherein Q is a methylene group, $Z^2$ is a single bond and $R^4$ is —

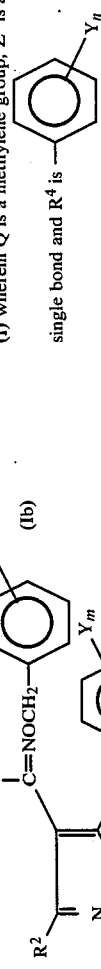

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 551 | CH$_3$ | CH$_3$ | H | 4-COC(CH$_3$)$_2$—COOCH$_3$ | H | O | $n_D^{20}$ 1.5630 |
| 552 | CH$_3$ | CH$_3$ | H | 4-CO-C$_6$H$_5$ | H | O | $n_D^{20}$ 1.5941 |
| 553 | CH$_3$ | CH$_3$ | H | 4-CO-C$_6$H$_5$ | 4-Cl | O | $n_D^{20}$ 1.5850 |
| 554 | CH$_3$ | CH$_3$ | H | 4-CO-C$_6$H$_4$-4-Cl | H | O | $n_D^{20}$ 1.5952 |
| 555 | CH$_3$ | CH$_3$ | H | 4-CO-C$_6$H$_4$-4-Cl | 4-F | O | $n_D^{20}$ 1.5935 |
| 556 | CH$_3$ | CH$_3$ | H | 4-CO-C$_6$H$_4$-4-Cl | 4-Cl | O | $n_D^{20}$ 1.5967 |
| 557 | CH$_3$ | CH$_3$ | H | 4-CO-C$_6$H$_4$-4-Cl | 4-OCH$_3$ | O | $n_D^{20}$ 1.5937 |

TABLE 1(a)-continued

This formula corresponds to the general formula (I) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C) or refractive index |
|---|---|---|---|---|---|---|---|
| 558 | $CH_3$ | $CH_3$ | H | 4-CO-C6H4-C4H9-t | H | O | $n_D^{20}$ 1.5764 |
| 559 | $CH_3$ | $CH_3$ | H | 4-CO-C6H4-C4H9-t | 4-F | O | $n_D^{20}$ 1.5643 |
| 560 | $CH_3$ | $CH_3$ | H | 4-CO-C6H4-C4H9-t | 4-Cl | O | $n_D^{20}$ 1.5830 |
| 561 | $CH_3$ | $CH_3$ | H | 4-CO-C6H4-C4H9-t | 4-OCH3 | O | $n_D^{20}$ 1.5782 |
| 562 | $CH_3$ | $CH_3$ | H | 4-(2-methyl-1,3-dioxolan-2-yl) | H | O | $n_D^{20}$ 1.5698 |
| 563 | $CH_3$ | $CH_3$ | H | 4-(2-methyl-1,3-dioxolan-2-yl) | 4-F | O | $n_D^{20}$ 1.5555 |

TABLE 1(a)-continued

This formula corresponds to the general formula (Ib) wherein Q is a methylene group, $Z^2$ is a single bond and $R^4$ is —

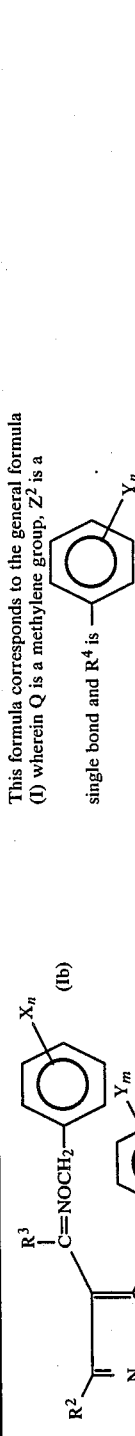

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 564 | $CH_3$ | $CH_3$ | H | ![O-C(CH3)2-CH2-CH2-O] | 4-Cl | O | $n_D^{20}$ 1.5569 |
| 565 | $CH_3$ | $CH_3$ | H | ![O-C(CH3)2-CH2-CH(CH3)-O] | H | O | $n_D^{20}$ 1.5619 |
| 566 | $CH_3$ | $CH_3$ | H | ![O-C(CH3)2-CH2-CH(CH3)-O] | 4-F | O | Paste |
| 567 | $CH_3$ | $CH_3$ | H | ![O-C(CH3)2-CH2-CH(CH3)-O] | 4-Cl | O | $n_D^{20}$ 1.5689 |
| 568 | $CH_3$ | $CH_3$ | H | ![O-C(CH3)2-CH2-CH(CH3)-O] | 4-OCH$_3$ | O | $n_D^{20}$ 1.5593 |
| 569 | $CH_3$ | $CH_3$ | H | ![O-C(C2H5)-CH2-CH2-O] | H | O | $n_D^{20}$ 1.5630 |

TABLE 1(a)-continued

This formula corresponds to the general formula (I) wherein Q is a methylene group, $Z^2$ is a single bond and $R^4$ is:

(Ib) structure: pyrazole with $R^1$ on N, $R^2$ at C, =C(R^3)NOCH_2-phenyl(X_n), linked via $Z^1$ to phenyl(Y_m)

$R^4$ = phenyl-$Y_n$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 570 | $CH_3$ | $CH_3$ | H | 4-(2-ethyl-1,3-dioxolan-2-yl) ($C_2H_5$) | 4-F | O | $n_D^{20}$ 1.5472 |
| 571 | $CH_3$ | $CH_3$ | H | 4-(2-ethyl-1,3-dioxolan-2-yl) ($C_2H_5$) | 4-OCH$_3$ | O | $n_D^{20}$ 1.5623 |
| 572 | $CH_3$ | $CH_3$ | H | 4-(2-ethyl-1,3-dioxolan-2-yl) ($C_2H_5$) | H | O | $n_D^{20}$ 1.5560 |
| 573 | $CH_3$ | $CH_3$ | H | 4-(5,5-dimethyl-2-methyl-1,3-dioxan-2-yl) | H | O | $n_D^{20}$ 1.5526 |
| 574 | $CH_3$ | $CH_3$ | H | 4-(5,5-dimethyl-2-methyl-1,3-dioxan-2-yl) | 4-F | O | $n_D^{20}$ 1.5656 |
| 575 | $CH_3$ | $CH_3$ | H | 4-(5,5-dimethyl-2-methyl-1,3-dioxan-2-yl) | 4-OCH$_3$ | O | $n_D^{20}$ 1.5123 |

TABLE 1(a)-continued

This formula corresponds to the general formula (I) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 576 | $CH_3$ | $CH_3$ | H | 4-C(S-)(S-)$CH_3$ (1,3-dithiolane) | H | O | $n_D^{20}$ 1.6188 |
| 577 | $CH_3$ | $CH_3$ | H | 4-C(S-)(S-)$C_2H_5$ (1,3-dithiane) | H | O | $n_D^{20}$ 1.6089 |
| 578 | $CH_3$ | $CH_3$ | H | 4-C(S-)(S-)$C_2H_5$ (1,3-dithiane) | 4-F | O | $n_D^{20}$ 1.5978 |
| 579 | $CH_3$ | $CH_3$ | H | 4-C(SC$_2$H$_5$)$_2$-C$_2$H$_5$ | H | O | $n_D^{20}$ 1.5831 |
| 580 | $CH_3$ | $CH_3$ | H | 4-C(S-)(S-)$C_3H_7$ (1,3-dithiane) | H | O | $n_D^{20}$ 1.5952 |
| 581 | $CH_3$ | $CH_3$ | H | 4-C(S-)(S-)CN (1,3-dithiolane) | H | O | Paste |

TABLE 1(a)-continued

This formula corresponds to the general formula (Ib) wherein Q is a methylene group, $Z^2$ is a single bond and $R^4$ is —⟨phenyl-$Y_n$⟩

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 582 | $CH_3$ | $CH_3$ | H | 4-C(S-CH₂CH₂-S)(COOCH₃) | H | O | $n_D^{20}$ 1.5665 |
| 583 | $CH_3$ | $CH_3$ | H | 4-C(S-CH₂CH₂-S)(COOC₃H₇-i) | H | O | $n_D^{20}$ 1.5685 |
| 584 | $CH_3$ | $CH_3$ | H | 4-CHCH₃<br>—OH | H | O | $n_D^{20}$ 1.5748 |
| 585 | $CH_3$ | $CH_3$ | H | 4-CHCH₃<br>—OCOCH₃ | H | O | $n_D^{20}$ 1.5623 |
| 586 | $CH_3$ | $CH_3$ | H | 4-C(CH₃)₂<br>—OH | H | O | $n_D^{20}$ 1.5682 |
| 587 | $CH_3$ | $CH_3$ | H | 4-CHC₂H₅<br>—OH | H | O | $n_D^{20}$ 1.5768 |
| 588 | $CH_3$ | $CH_3$ | H | 4-C(C₂H₅)(C₄H₉-n)<br>—OH | H | O | $n_D^{20}$ 1.5620 |

TABLE 1(a)-continued

This formula corresponds to the general formula (I) wherein Q is a methylene group, $Z^2$ is a single bond and $R^4$ is -[phenyl with $Y_n$]

(Ib) structure shown with $R^3$, $R^2$, $R^1$, N-N, C=NOCH$_2$, $Z^1$, $X_n$, $Y_m$ substituents on pyrazole/phenyl system.

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 589 | CH$_3$ | CH$_3$ | H | 4-N(H)(CHO) | H | O | m.p. 105.3 |
| 590 | CH$_3$ | CH$_3$ | H | 4-N(H)(COOCH$_3$) | H | O | $n_D^{20}$ 1.5808 |
| 591 | CH$_3$ | CH$_3$ | H | 4-N(H)(COOCH$_2$CH$_2$OCH$_3$) | H | O | $n_D^{20}$ 1.5705 |
| 592 | CH$_3$ | CH$_3$ | H | 4-N(H)(COOCH$_2$CH$_2$OCH$_3$) | 4-F | O | $n_D^{20}$ 1.5621 |
| 593 | CH$_3$ | CH$_3$ | H | 4-N(H)(COOCH$_2$CH$_2$OCH$_3$) | 4-OCH$_3$ | O | $n_D^{20}$ 1.5659 |
| 594 | CH$_3$ | CH$_3$ | H | 4-N(H)(COOC$_3$H$_7$-i) | H | O | m.p. 115.2 |
| 595 | CH$_3$ | CH$_3$ | H | 4-N(H)(COOC$_3$H$_7$-i) | 4-F | O | $n_D^{20}$ 1.5645 |

TABLE 1(a)-continued

This formula corresponds to the general formula (I) wherein Q is a methylene group, $Z^2$ is a single bond and $R^4$ is a phenyl group with $Y_n$ substituents.

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 596 | $CH_3$ | $CH_3$ | H | 4-N(CH$_3$)COOCH$_3$ | H | O | Paste |
| 597 | $CH_3$ | $CH_3$ | H | 2-N(CH$_3$)COOCH$_3$ | 4-F | O | $n_D^{20}$ 1.5561 |
| 598 | $CH_3$ | $CH_3$ | H | 2-N(CH$_3$)COOCH$_3$ | 4-OCH$_3$ | O | $n_D^{20}$ 1.5599 |
| 599 | $CH_3$ | $CH_3$ | H | 3-N(CH$_3$)COOCH$_3$ | H | O | $n_D^{20}$ 1.5764 |
| 600 | $CH_3$ | $CH_3$ | H | 3-N(CH$_3$)COOCH$_3$ | 4-F | O | $n_D^{20}$ 1.5685 |
| 601 | $CH_3$ | $CH_3$ | H | 3-N(CH$_3$)COOCH$_3$ | 4-OCH$_3$ | O | $n_D^{20}$ 1.5723 |
| 602 | $CH_3$ | $CH_3$ | H | 4-N(CH$_3$)COOCH$_3$ | H | O | Paste |

TABLE 1(a)-continued

This formula corresponds to the general formula (I) wherein Q is a methylene group, $Z^2$ is a single bond and $R^4$ is —[phenyl]—$Y_n$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 603 | CH$_3$ | CH$_3$ | H | 4-N(CH$_3$)COOCH$_3$ | 4-F | O | Paste |
| 604 | CH$_3$ | CH$_3$ | H | 4-N(CH$_3$)COOCH$_2$CH$_2$OCH$_3$ | H | O | $n_D^{20}$ 1.5683 |
| 605 | CH$_3$ | CH$_3$ | H | 3-N(CH$_3$)COOC$_3$H$_7$-n | H | O | $n_D^{20}$ 1.5662 |
| 606 | CH$_3$ | CH$_3$ | H | 3-N(CH$_3$)COOC$_3$H$_7$-n | 4-F | O | $n_D^{20}$ 1.5582 |
| 607 | CH$_3$ | CH$_3$ | H | 3-N(CH$_3$)COOC$_3$H$_7$-n | 4-OCH$_3$ | O | $n_D^{20}$ 1.5625 |
| 608 | CH$_3$ | CH$_3$ | H | 4-N(CH$_3$)COOC$_3$H$_7$-n | H | O | $n_D^{20}$ 1.5564 |
| 609 | CH$_3$ | CH$_3$ | H | 4-N(CH$_3$)COOC$_3$H$_7$-n | 4-F | O | $n_D^{20}$ 1.5559 |

TABLE 1(a)-continued

This formula corresponds to the general formula (I) wherein Q is a methylene group, $Z^2$ is a single bond and $R^4$ is —

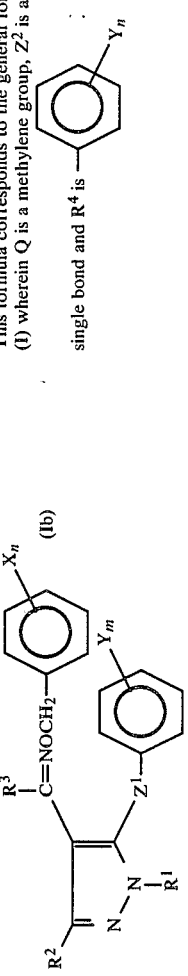

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 610 | $CH_3$ | $CH_3$ | H | 4-N(CH$_3$)COOC$_3$H$_7$—n | 4-Cl | O | $n_D^{20}$ 1.5595 |
| 611 | $CH_3$ | $CH_3$ | H | 4-N(CH$_3$)COOC$_3$H$_7$—n | 4-OCH$_3$ | O | $n_D^{20}$ 1.5557 |
| 612 | $CH_3$ | $CH_3$ | H | 4-N(CH$_3$)COOC$_3$H$_7$—i | H | O | $n_D^{20}$ 1.5648 |
| 613 | $CH_3$ | $CH_3$ | H | 4-N(CH$_3$)COOC$_3$H$_7$—i | 4-F | O | $n_D^{20}$ 1.5529 |
| 614 | $CH_3$ | $CH_3$ | H | 4-N(CH$_3$)COOC$_4$H$_9$—i | H | O | $n_D^{20}$ 1.5582 |
| 615 | $CH_3$ | $CH_3$ | H | 4-N(CH$_3$)COOC$_4$H$_9$—i | 4-F | O | $n_D^{20}$ 1.5421 |
| 616 | $CH_3$ | $CH_3$ | H | 4-N(CH$_3$)COOC$_4$H$_9$—i | 4-Cl | O | $n_D^{20}$ 1.5573 |

TABLE 1(a)-continued

This formula corresponds to the general formula (I) wherein Q is a methylene group, $Z^2$ is a single bond and $R^4$ is

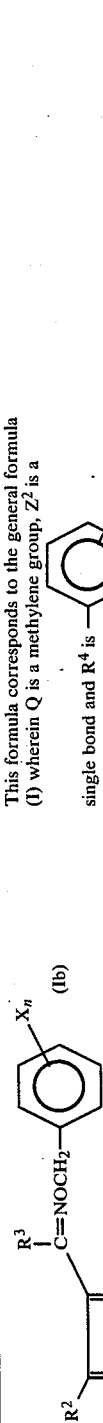

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 617 | $CH_3$ | $CH_3$ | H | 4-N(CH$_3$)(COOC$_4$H$_9$-i) | 4-OCH$_3$ | O | $n_D^{20}$ 1.5538 |
| 618 | $CH_3$ | $CH_3$ | H | 4-N(CH$_3$)(COOC$_4$H$_9$-i) | 3,4(—OCH$_2$O—) | O | $n_D^{20}$ 1.5621 |
| 619 | $CH_3$ | $CH_3$ | H | 4-N(C$_2$H$_5$)(COOCH$_3$) | H | O | $n_D^{20}$ 1.5638 |
| 620 | $CH_3$ | $CH_3$ | H | 4-N(C$_2$H$_5$)(COOCH$_3$) | 4-F | O | Paste |
| 621 | $CH_3$ | $CH_3$ | H | 4-N(C$_2$H$_5$)(COOCH$_3$) | 4-OCH$_3$ | O | $n_D^{20}$ 1.5656 |
| 622 | $CH_3$ | $CH_3$ | $CH_3$ | 4-N(C$_2$H$_5$)(COOCH$_3$) | H | O | m.p. 83.4 |
| 623 | $CH_3$ | $CH_3$ | H | 4-N(C$_2$H$_5$)(COOCH$_2$CH$_2$Cl) | H | O | $n_D^{20}$ 1.5706 |

TABLE 1(a)-continued

This formula corresponds to the general formula (I) wherein Q is a methylene group, $Z^2$ is a single bond and $R^4$ is —⌬—$Y_n$ (Ib) structure shown with $R^3$, $C=NOCH_2$—⌬—$X_n$, $R^2$, $Y_m$, $Z^1$—⌬, N—N—$R^1$, $R^2$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 624 | CH₃ | CH₃ | H | 4-N(C₂H₅)(COOCH₂CH₂Cl) | 4-F | O | Paste |
| 625 | CH₃ | CH₃ | H | 4-N(C₂H₅)(COOCH₂CH₂Cl) | 4-OCH₃ | O | $n_D^{20}$ 1.5695 |
| 626 | CH₃ | CH₃ | H | 4-N(C₂H₅)(COOC₃H₇-n) | H | O | $n_D^{20}$ 1.5605 |
| 627 | CH₃ | CH₃ | H | 4-N(C₂H₅)(COOC₃H₇-n) | 4-F | O | $n_D^{20}$ 1.5532 |
| 628 | CH₃ | CH₃ | H | 4-N(C₂H₅)(COOC₃H₇-n) | 4-OCH₃ | O | $n_D^{20}$ 1.5602 |
| 629 | CH₃ | CH₃ | H | 4-N(C₂H₅)(COOC₃H₇-i) | H | O | $n_D^{20}$ 1.5549 |
| 630 | CH₃ | CH₃ | H | 4-N(C₂H₅)(COOC₃H₇-i) | 4-F | O | $n_D^{20}$ 1.5448 |

TABLE 1(a)-continued

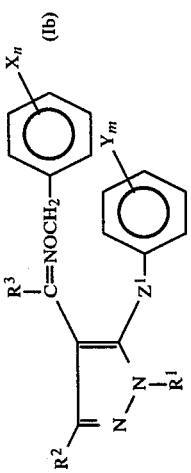

This formula corresponds to the general formula (I) wherein Q is a methylene group, $Z^2$ is a single bond and $R^4$ is

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 631 | $CH_3$ | $CH_3$ | H | 4-N(C₂H₅)(COOC₃H₇—i) | 4-OCH₃ | O | $n_D^{20}$ 1.5513 |
| 632 | $CH_3$ | $CH_3$ | H | 4-N(C₂H₅)(COOC₄H₉—t) | H | O | $n_D^{20}$ 1.5689 |
| 633 | $CH_3$ | $CH_3$ | H | 4-N(C₂H₅)(COOC₄H₉—t) | 4-F | O | $n_D^{20}$ 1.5701 |
| 634 | $CH_3$ | $CH_3$ | H | 4-N(C₂H₅)(COOCH₂CHC₄H₉—n / C₂H₅) | H | O | $n_D^{20}$ 1.5481 |
| 635 | $CH_3$ | $CH_3$ | H | 4-N(C₂H₅)(COOCH₂CHC₄H₉—n / C₂H₅) | 4-F | O | $n_D^{20}$ 1.5415 |
| 636 | $CH_3$ | $CH_3$ | H | 4-N(C₃H₇—i)(CHO) | H | O | m.p. 73.3 |

TABLE 1(a)-continued

This formula corresponds to the general formula (I) wherein Q is a methylene group, $Z^2$ is a single bond and $R^4$ is

| Compound No. | $R^1$ | $R^2$ | $R^3$ | $X_n$ | $Y_n$ | $Z^1$ | Physical property m.p. (°C.) or refractive index |
|---|---|---|---|---|---|---|---|
| 637 | $CH_3$ | $CH_3$ | H | 4-N(C$_3$H$_7$-i)(CHO) | 4-F | O | $n_D^{20}$ 1.5685 |
| 638 | $CH_3$ | $CH_3$ | H | 4-N(C$_3$H$_7$-i)(CHO) | 4-OCH$_3$ | O | $n_D^{20}$ 1.5710 |
| 639 | $CH_3$ | $CH_3$ | H | 4-N(C$_3$H$_7$-i)(CHO) | H | O | $n_D^{20}$ 1.5520 |
| 640 | $CH_3$ | $CH_3$ | H | 4-N(C$_3$H$_7$-i)(COOCH$_3$) | 4-F | O | Paste |
| 641 | $CH_3$ | $CH_3$ | H | 4-N(C$_3$H$_7$-i)(COOCH$_3$) | 4-OCH$_3$ | O | $n_D^{20}$ 1.5610 |
| 642 | $CH_3$ | $CH_3$ | H | 4-N(C$_3$H$_7$-i)(COOCH$_3$) | H | O | $n_D^{20}$ 1.5516 |
| 643 | $CH_3$ | $CH_3$ | H | 4-N(C$_3$H$_7$-i)(COOC$_3$H$_7$-n) | 4-F | O | $n_D^{20}$ 1.5489 |

TABLE 1(a)-continued

This formula corresponds to the general formula (I) wherein Q is a methylene group, $Z^2$ is a single bond and $R^4$ is a 4-Y_n-phenyl group.

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 644 | $CH_3$ | $CH_3$ | H | 4-N(C$_3$H$_7$-i)(COOC$_3$H$_7$-n) | 4-OCH$_3$ | O | $n_D^{20}$ 1.5542 |
| 645 | $CH_3$ | $CH_3$ | H | 4-N(C$_3$H$_7$-i)(COOC$_3$H$_7$-i) | H | O | $n_D^{20}$ 1.5545 |
| 646 | $CH_3$ | $CH_3$ | H | 4-N(C$_3$H$_7$-i)(COOC$_3$H$_7$-i) | 4-F | O | $n_D^{20}$ 1.5448 |
| 647 | $CH_3$ | $CH_3$ | H | 4-N(C$_2$H$_5$)(COOC$_4$H$_9$-t) | H | O | Paste |
| 648 | $CH_3$ | $CH_3$ | H | 4-N(oxazolidinone) | H | O | m.p. 85.0 |
| 649 | $CH_3$ | $CH_3$ | H | 4-N(oxazolidinone) | 4-F | O | Paste |

TABLE 1(a)-continued

This formula corresponds to the general formula (I) wherein Q is a methylene group, $Z^2$ is a single bond and $R^4$ is

[structure: phenyl with $Y_n$]

[structure (Ib): pyrazole with R¹, R², R³, C=NOCH₂, phenyl-Xₙ/Yₘ, Z¹, phenyl-Yₘ]

| Compound No. | R¹ | R² | R³ | Xₙ | Yₘ | Z¹ | Physical property m.p. (°C.) or refractive index |
|---|---|---|---|---|---|---|---|
| 650 | CH₃ | CH₃ | H | 4-N(oxazolidinone) | 4-OCH₃ | O | $n_D^{20}$ 1.5861 |
| 651 | CH₃ | CH₃ | H | 4-N(5-methyl-oxazolidinone) | H | O | m.p. 115.1 |
| 652 | CH₃ | CH₃ | H | 4-N(5-methyl-oxazolidinone) | 4-F | O | $n_D^{20}$ 1.5718 |
| 653 | CH₃ | CH₃ | H | 4-N(5-CH₂OCH₃-oxazolidinone) | H | O | $n_D^{20}$ 1.5730 |
| 654 | CH₃ | CH₃ | H | 4-N(5-CH₂OCH₃-oxazolidinone) | 4-F | O | $n_D^{20}$ 1.5551 |

TABLE 1(a)-continued

This formula corresponds to the general formula (Ib) (I) wherein Q is a methylene group, $Z^2$ is a single bond and $R^4$ is —⟨phenyl⟩—$Y_n$

| Compound No. | $R^1$ | $R^2$ | $R^3$ | $X_n$ | $Y_m$ | $Z^1$ | Physical property m.p. (°C.) or refractive index |
|---|---|---|---|---|---|---|---|
| 655 | $CH_3$ | $CH_3$ | H | 4-N(oxazolidinone-$CH_2OCH_3$) | 4-$OCH_3$ | O | $n_D^{20}$ 1.5660 |
| 656 | $CH_3$ | $CH_3$ | H | 4-N(oxazolidinone-$C_2H_5$) | H | O | $n_D^{20}$ 1.5718 |
| 657 | $CH_3$ | $CH_3$ | H | 4-N(oxazolidinone-$C_2H_5$) | 4-F | O | $n_D^{20}$ 1.5601 |

TABLE I(b)

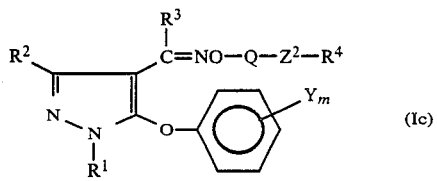

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 658 | $CH_3$ | $CH_3$ | H | $-CH_2CH_2-$ | O | phenyl | H | $n_D^{20}$ 1.5657 |
| 659 | $CH_3$ | $CH_3$ | H | $-CH_2CH_2-$ | O | 2-$CH_3$-phenyl | H | $n_D^{20}$ 1.5760 |
| 660 | $CH_3$ | $CH_3$ | H | $-CH_2CH_2-$ | O | 3-$CH_3$-phenyl | H | $n_D^{20}$ 1.5683 |
| 661 | $CH_3$ | $CH_3$ | H | $-CH_2CH_2-$ | O | 4-$CH_3$-phenyl | H | $n_D^{20}$ 1.5704 |
| 662 | $CH_3$ | $CH_3$ | H | $-CH_2CH_2-$ | O | 4-$CH_3$-phenyl | 4-F | $n_D^{20}$ 1.5524 |
| 663 | $CH_3$ | $CH_3$ | H | $-CH_2CH_2-$ | O | 3-$CF_3$-phenyl | H | m.p. 63.4 |
| 664 | $CH_3$ | $CH_3$ | H | $-CH_2CH_2-$ | O | 3-$C_4H_9$-t-phenyl | H | $n_D^{20}$ 1.5592 |
| 665 | $CH_3$ | $CH_3$ | H | $-CH_2CH_2-$ | O | 3-$C_4H_9$-t-phenyl | 4-Cl | $n_D^{20}$ 1.5641 |
| 666 | $CH_3$ | $CH_3$ | H | $-CH_2CH_2-$ | O | 3-$C_4H_9$-t-phenyl | 3-Cl | $n_D^{20}$ 1.5669 |

TABLE I(b)-continued

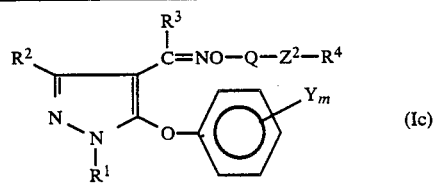

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 667 | CH₃ | CH₃ | H | —CH₂CH₂— | O | 4-t-C₄H₉-phenyl | 4-OCH₃ | $n_D^{20}$ 1.5606 |
| 668 | CH₃ | CH₃ | H | —CH₂CH₂— | O | 4-t-C₄H₉-phenyl | H | $n_D^{20}$ 1.5509 |
| 669 | CH₃ | CH₃ | H | —CH₂CH₂— | O | 4-t-C₄H₉-phenyl | 3-OCH₃ | $n_D^{20}$ 1.5459 |
| 670 | CH₃ | CH₃ | H | —CH₂CH₂— | O | 4-t-C₄H₉-phenyl | 4—OCH₃ | m.p. 59.6 |
| 671 | CH₃ | CH₃ | H | —CH₂CH₂— | O | 4-t-C₄H₉-phenyl | 3-CF₃ | $n_D^{20}$ 1.5287 |
| 672 | CH₃ | CH₃ | H | —CH₂CH₂— | O | 4-(2-phenylpropan-2-yl)phenyl | H | $n_D^{20}$ 1.5612 |
| 673 | CH₃ | CH₃ | H | —CH₂CH₂— | O | 4-(2-phenylpropan-2-yl)phenyl | 4-Cl | $n_D^{20}$ 1.5741 |
| 674 | CH₃ | CH₃ | H | —CH₂CH₂— | O | 2-F-phenyl | H | $n_D^{20}$ 1.5618 |
| 675 | CH₃ | CH₃ | H | —CH₂CH₂— | O | 3-F-phenyl | H | $n_D^{20}$ 1.5657 |
| 676 | CH₃ | CH₃ | H | —CH₂CH₂— | O | 3-F-phenyl | 4-Cl | m.p. 100.2 |

TABLE I(b)-continued

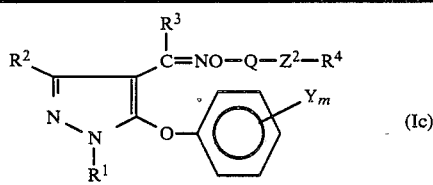

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 677 | $CH_3$ | $CH_3$ | H | $-CH_2CH_2-$ | O | 4-F-C$_6$H$_4$ | H | $n_D^{20}$ 1.5552 |
| 678 | $CH_3$ | $CH_3$ | H | $-CH_2CH_2-$ | O | 4-F-C$_6$H$_4$ | 4-Cl | $n_D^{20}$ 1.5738 |
| 679 | $CH_3$ | $CH_3$ | H | $-CH_2CH_2-$ | O | 4-F-C$_6$H$_4$ | 3-Cl | $n_D^{20}$ 1.5730 |
| 680 | $CH_3$ | $CH_3$ | H | $-CH_2CH_2-$ | O | 4-F-C$_6$H$_4$ | 4-OCH$_3$ | $n_D^{20}$ 1.5681 |
| 681 | $CH_3$ | $CH_3$ | H | $-CH_2CH_2-$ | O | 2-Cl-C$_6$H$_4$ | H | m.p. 51.2 |
| 682 | $CH_3$ | $CH_3$ | H | $-CH_2CH_2-$ | O | 3-Cl-C$_6$H$_4$ | H | $n_D^{20}$ 1.5722 |
| 683 | $CH_3$ | $CH_3$ | H | $-CH_2CH_2-$ | O | 4-Cl-C$_6$H$_4$ | H | $n_D^{20}$ 1.5936 |
| 684 | $CH_3$ | $CH_3$ | H | $-CH_2CH_2-$ | O | 4-Br-C$_6$H$_4$ | 4-Cl | $n_D^{20}$ 1.5936 |
| 685 | $CH_3$ | $CH_3$ | H | $-CH_2CH_2-$ | O | 4-Br-C$_6$H$_4$ | 4-Cl | m.p. 101.5 |
| 686 | $CH_3$ | $CH_3$ | H | $-CH_2CH_2-$ | O | 4-CN-C$_6$H$_4$ | H | m.p. 86.1 |
| 687 | $CH_3$ | $CH_3$ | H | $-CH_2CH_2-$ | O | 4-CHO-C$_6$H$_4$ | H | $n_D^{20}$ 1.5833 |

TABLE I(b)-continued

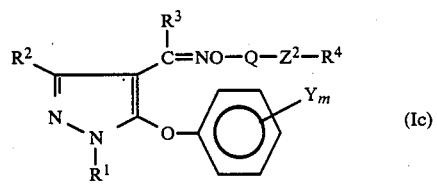

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 688 | CH₃ | CH₃ | H | —CH₂CH₂— | O | 4-CHO-phenyl | 4-F | m.p. 87.7 |
| 689 | CH₃ | CH₃ | H | —CH₂CH₂— | O | 4-CHO-phenyl | 4-OCH₃ | $n_D^{20}$ 1.5777 |
| 690 | CH₃ | CH₃ | H | —CH₂CH₂— | O | 2-OCH₃-phenyl | H | m.p. 58.6 |
| 691 | CH₃ | CH₃ | H | —CH₂CH₂— | O | 3-OCH₃-phenyl | H | $n_D^{20}$ 1.5769 |
| 692 | CH₃ | CH₃ | H | —CH₂CH₂— | O | 4-OCH₃-phenyl | 4-Cl | $n_D^{20}$ 1.5583 |
| 693 | CH₃ | CH₃ | H | —CH₂CH₂— | O | 4-OCH₃-phenyl | 4-Cl | m.p. 90.3 |
| 694 | CH₃ | CH₃ | H | —CH₂CH₂— | O | 4-OCH₃-phenyl | 4-F | $n_D^{20}$ 1.5565 |
| 695 | CH₃ | CH₃ | H | —CH₂CH₂— | O | 4-OCH₃-phenyl | 4-OCH₃ | m.p. 81.5 |
| 696 | CH₃ | CH₃ | H | —CH₂CH₂— | O | 4-OC₂H₅-phenyl | H | $n_D^{20}$ 1.5682 |
| 697 | CH₃ | CH₃ | H | —CH₂CH₂— | O | 4-OC₂H₅-phenyl | 4-F | m.p. 53.0 |

TABLE I(b)-continued

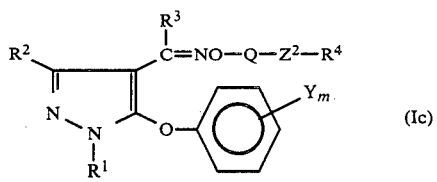

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 698 | CH₃ | CH₃ | H | —CH₂CH₂— | O | ⌬—OC₂H₅ | 4-OCH₃ | m.p. 103.6 |
| 699 | CH₃ | CH₃ | H | —CH₂CH₂— | O | ⌬—O—⌬ | H | $n_D^{20}$ 1.5800 |
| 700 | CH₃ | CH₃ | H | —CH₂CH₂— | O | ⌬-SCH₃ (ortho) | H | $n_D^{20}$ 1.5901 |
| 701 | CH₃ | CH₃ | H | —CH₂CH₂— | O | ⌬—SCH₃ | H | $n_D^{20}$ 1.5835 |
| 702 | CH₃ | CH₃ | H | —CH₂CH₂— | O | ⌬—COCH₃ | H | $n_D^{20}$ 1.5742 |
| 703 | CH₃ | CH₃ | H | —CH₂CH₂— | O | ⌬—CH(OCH₃)₂ | H | $n_D^{20}$ 1.5851 |
| 704 | CH₃ | CH₃ | H | —CH₂CH₂— | O | ⌬-COOCH₃ (meta) | H | m.p. 60.6 |
| 705 | CH₃ | CH₃ | H | —CH₂CH₂— | O | ⌬—COOCH₃ | H | m.p. 60.5 |
| 706 | CH₃ | CH₃ | H | —CH₂CH₂— | O | ⌬—COOC₂H₅ | H | $n_D^{20}$ 1.5577 |
| 707 | CH₃ | CH₃ | H | —CH₂CH₂— | O | ⌬-COOC₃H₇—i (ortho) | H | $n_D^{20}$ 1.5579 |

TABLE I(b)-continued

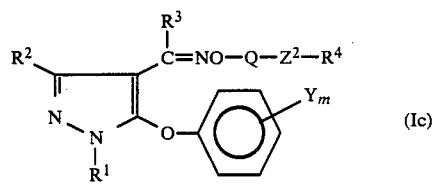

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 708 | $CH_3$ | $CH_3$ | H | $-CH_2CH_2-$ | O | phenyl with CH₃ and COOC₃H₇—i | 4-Cl | $n_D^{20}$ 1.5581 |
| 709 | $CH_3$ | $CH_3$ | H | $-CH_2CH_2-$ | O | phenyl-COOC₃H₇—i | H | $n_D^{20}$ 1.5632 |
| 710 | $CH_3$ | $CH_3$ | H | $-CH_2CH_2-$ | O | phenyl-COOC₄H₉—s | H | $n_D^{20}$ 1.5577 |
| 711 | $CH_3$ | $CH_3$ | H | $-CH_2CH_2-$ | O | phenyl-COOC₄H₉—n | H | $n_D^{20}$ 1.5555 |
| 712 | $CH_3$ | $CH_3$ | H | $-CH_2CH_2-$ | O | phenyl-COOC₄H₉—t | H | $n_D^{20}$ 1.5490 |
| 713 | $CH_3$ | $CH_3$ | H | $-CH_2CH_2-$ | O | phenyl with CH₃ and CH₃ | H | $n_D^{20}$ 1.5616 |
| 714 | $CH_3$ | $CH_3$ | H | $-CH_2CH_2-$ | O | phenyl with CH₃ and CH₃ | 4-Cl | m.p. 92.5 |
| 715 | $CH_3$ | $CH_3$ | H | $-CH_2CH_2-$ | O | phenyl with CH₃ and CH₃ | 3-Cl | $n_D^{20}$ 1.5701 |
| 716 | $CH_3$ | $CH_3$ | H | $-CH_2CH_2-$ | O | phenyl with CH₃ and CH₃ | 4-OCH₃ | $n_D^{20}$ 1.5598 |

TABLE I(b)-continued

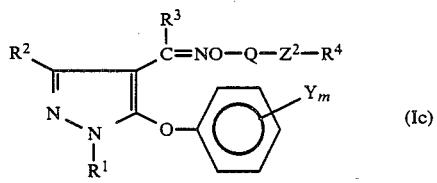

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 717 | $CH_3$ | $CH_3$ | H | —$CH_2CH_2$— | O | 2,4-dichlorophenyl | H | $n_D^{20}$ 1.5813 |
| 718 | $CH_3$ | $CH_3$ | H | —$CH_2CH_2$— | O | 2,3-dichlorophenyl | H | $n_D^{20}$ 1.5813 |
| 719 | $CH_3$ | $CH_3$ | H | —$CH_2CH_2$— | O | 3,4-dichlorophenyl | H | $n_D^{20}$ 1.5846 |
| 720 | $CH_3$ | $CH_3$ | H | —$CH_2CH_2$— | O | 2,5-dichlorophenyl | H | m.p. 80.3 |
| 721 | $CH_3$ | $CH_3$ | H | —$CH_2CH_2$— | O | 3,5-dichlorophenyl | H | $n_D^{20}$ 1.5862 |
| 722 | $CH_3$ | $CH_3$ | H | —$CH_2CH_2$— | O | 2,6-dichlorophenyl | H | $n_D^{20}$ 1.5816 |
| 723 | $CH_3$ | $CH_3$ | H | —$CH_2CH_2$— | O | 3,4-dichlorophenyl | 4-Cl | $n_D^{20}$ 1.5756 |
| 724 | $CH_3$ | $CH_3$ | H | —$CH_2CH_2$— | O | 3,4-dichlorophenyl | 4-$OCH_3$ | $n_D^{20}$ 1.5798 |

TABLE I(b)-continued

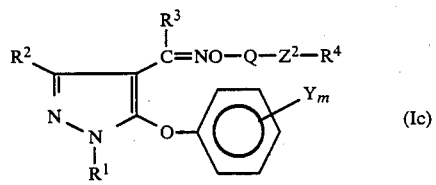

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 725 | $CH_3$ | $CH_3$ | H | $-CH_2CH_2-$ | O | 3,4-di-Cl-phenyl | 4-F | m.p. 72.2 |
| 726 | $CH_3$ | $CH_3$ | H | $-CH_2CH_2-$ | O | 4-Cl-3-CH$_3$-phenyl | H | m.p. 73.8 |
| 727 | $CH_3$ | $CH_3$ | H | $-CH_2CH_2-$ | O | 4-Cl-3-CH$_3$-phenyl | 4-Cl | $n_D^{20}$ 1.5694 |
| 728 | $CH_3$ | $CH_3$ | H | $-CH_2CH_2-$ | O | 4-Cl-3-CH$_3$-phenyl | 4-OCH$_3$ | $n_D^{20}$ 1.5665 |
| 729 | $CH_3$ | $CH_3$ | H | $-CH_2CH_2-$ | O | 4-Cl-3-CH$_3$-phenyl | 4-F | $n_D^{20}$ 1.5588 |
| 730 | $CH_3$ | $CH_3$ | H | $-CH_2CH_2-$ | O | 3-Cl-4-t-C$_4$H$_9$-phenyl | H | $n_D^{20}$ 1.5677 |
| 731 | $CH_3$ | $CH_3$ | H | $-CH_2CH_2-$ | O | 3-Cl-4-t-C$_4$H$_9$-phenyl | 4-Cl | $n_D^{20}$ 1.5650 |
| 732 | $CH_3$ | $CH_3$ | H | $-CH_2CH_2-$ | O | 3-Cl-4-t-C$_4$H$_9$-phenyl | 4-F | $n_D^{20}$ 1.5552 |

TABLE I(b)-continued

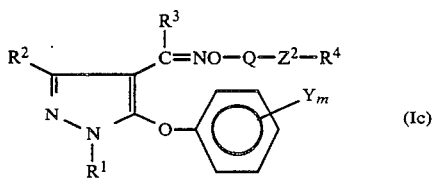

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 733 | $CH_3$ | $CH_3$ | H | $-CH_2CH_2-$ | O | 3-Cl, 4-$C_4H_9$-t phenyl | 4-$OCH_3$ | $n_D^{20}$ 1.5657 |
| 734 | $CH_3$ | $CH_3$ | H | $-CH_2CH_2-$ | O | 3,4-methylenedioxyphenyl | 4-$OCH_3$ | $n_D^{20}$ 1.5682 |
| 735 | $CH_3$ | $CH_3$ | H | $-CH_2CH_2-$ | O | 3,4-methylenedioxyphenyl | 4-F | $n_D^{20}$ 1.5612 |
| 736 | $CH_3$ | $CH_3$ | H | $-CH_2CH_2-$ | O | 2,4,5-trichlorophenyl | H | $n_D^{20}$ 1.5737 |
| 737 | $CH_3$ | $C_2H_5$ | H | $-CH_2CH_2-$ | O | 3-$CH_3$ phenyl | H | $n_D^{20}$ 1.5626 |
| 738 | $CH_3$ | $C_3H_7$-i | H | $-CH_2CH_2-$ | O | 3-$CH_3$ phenyl | H | $n_D^{20}$ 1.5571 |
| 739 | $CH_3$ | $CH_3$ | $CH_3$ | $-CH_2CH_2-$ | O | 4-$C_4H_9$-t phenyl | H | $n_D^{20}$ 1.5530 |
| 740 | $CH_3$ | $CH_3$ | H | $-CH_2CH(CH_3)-$ | O | phenyl | H | $n_D^{20}$ 1.5530 |
| 741 | $CH_3$ | $CH_3$ | H | $-CH_2CH(CH_3)-$ | O | phenyl | 4-F | $n_D^{20}$ 1.5484 |

TABLE I(b)-continued

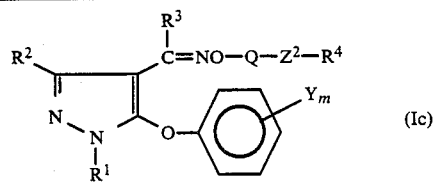

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 742 | $CH_3$ | $CH_3$ | H | $-CH_2CH-$<br>$\quad\quad\mid$<br>$\quad\quad CH_3$ | O | ⌬—$CH_3$ | H | $n_D^{20}$ 1.5520 |
| 743 | $CH_3$ | $CH_3$ | H | $-CH_2CH-$<br>$\quad\quad\mid$<br>$\quad\quad CH_3$ | O | ⌬—$C_4H_9-t$ | H | $n_D^{20}$ 1.5405 |
| 744 | $CH_3$ | $CH_3$ | H | $-CH_2CH-$<br>$\quad\quad\mid$<br>$\quad\quad CH_3$ | O | ⌬—$C_4H_9-t$ | 4-F | $n_D^{20}$ 1.5368 |
| 745 | $CH_3$ | $CH_3$ | H | $-CH_2CH-$<br>$\quad\quad\mid$<br>$\quad\quad CH_3$ | O | ⌬—$OCH_3$ | H | $n_D^{20}$ 1.5482 |
| 746 | $CH_3$ | $CH_3$ | H | $-CH_2CH-$<br>$\quad\quad\mid$<br>$\quad\quad CH_3$ | O | benzodioxole | H | $n_D^{20}$ 1.5693 |
| 747 | $CH_3$ | $CH_3$ | H | $-CH_2CH-$<br>$\quad\quad\mid$<br>$\quad\quad C_3H_7-i$ | O | ⌬—$CH_3$ | H | $n_D^{20}$ 1.5453 |
| 748 | $CH_3$ | $CH_3$ | H | $-CH_2CH-$<br>$\quad\quad\mid$<br>$\quad\quad C_3H_7-i$ | O | ⌬—$CH_3$ | 4-F | $n_D^{20}$ 1.5418 |
| 749 | $CH_3$ | $CH_3$ | H | $-CH_2CH-$<br>$\quad\quad\mid$<br>$\quad\quad C_3H_7-i$ | O | ⌬—$CH_3$ | 4-Cl | $n_D^{20}$ 1.5613 |
| 750 | $CH_3$ | $CH_3$ | H | $-CH_2CH-$<br>$\quad\quad\mid$<br>$\quad\quad C_3H_7-i$ | O | ⌬—$CH_3$ | 4-$OCH_3$ | $n_D^{20}$ 1.5440 |
| 751 | $CH_3$ | $CH_3$ | H | $-CH_2CH_2-$ | S | ⌬ | H | $n_D^{20}$ 1.5594 |
| 752 | $CH_3$ | $CH_3$ | H | $-CH_2CH_2-$ | S | ⌬—$CH_3$ | H | $n_D^{20}$ 1.5902 |

TABLE I(b)-continued

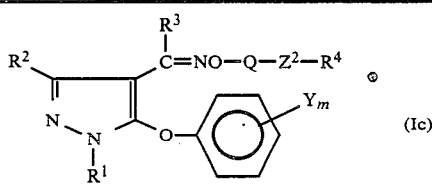

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 753 | CH$_3$ | CH$_3$ | H | —CH$_2$CH$_2$— | S | 4-t-C$_4$H$_9$-phenyl | H | $n_D^{20}$ 1.5775 |
| 754 | CH$_3$ | CH$_3$ | H | —CH$_2$CH$_2$— | S | 4-Cl-phenyl | H | m.p. 87.4 |
| 755 | CH$_3$ | CH$_3$ | H | —CH$_2$CH$_2$— | S | 3,4-Cl$_2$-phenyl | H | m.p. 96.4 |
| 756 | CH$_3$ | CH$_3$ | H | —CH$_2$CH$_2$CH$_2$— | O | phenyl | H | $n_D^{20}$ 1.5647 |
| 757 | CH$_3$ | CH$_3$ | H | —CH$_2$CH$_2$CH$_2$— | O | phenyl | 4-F | $n_D^{20}$ 1.5593 |
| 758 | CH$_3$ | CH$_3$ | H | —CH$_2$CH$_2$— | O | phenyl | 4-Cl | $n_D^{20}$ 1.5766 |
| 759 | CH$_3$ | CH$_3$ | H | —CH$_2$CH$_2$CH$_2$— | O | phenyl | 4-OCH$_3$ | $n_D^{20}$ 1.5700 |
| 760 | CH$_3$ | CH$_3$ | H | —CH$_2$CH$_2$CH$_2$— | O | 4-t-C$_4$H$_9$-phenyl | H | $n_D^{20}$ 1.5520 |
| 761 | CH$_3$ | CH$_3$ | H | —CH$_2$CH$_2$— | O | 4-Cl-phenyl | H | $n_D^{20}$ 1.5746 |
| 762 | CH$_3$ | CH$_3$ | H | —CH$_2$CH$_2$CH$_2$— | O | 4-Cl-phenyl | H | $n_D^{20}$ 1.5647 |
| 763 | CH$_3$ | CH$_3$ | H | —CH$_2$CH$_2$— | O | 4-Cl-phenyl | 4-F | $n_D^{20}$ 1.5648 |

TABLE I(b)-continued

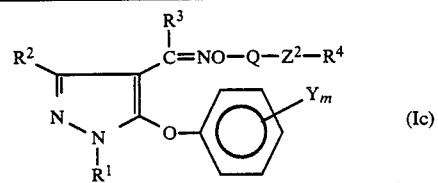

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 764 | $CH_3$ | $CH_3$ | H | —$CH_2CH_2CH_2$— | O | 4-Cl-phenyl | 4-$OCH_3$ | $n_D^{20}$ 1.5748 |
| 765 | $CH_3$ | $CH_3$ | H | —$CH_2CH_2CH_2$— | O | 4-$COOCH_3$-phenyl | H | $n_D^{20}$ 1.5689 |
| 766 | $CH_3$ | $CH_3$ | H | —$CH_2CH_2CH_2$— | O | phenyl | H | $n_D^{20}$ 1.5670 |
| 767 | $CH_3$ | $CH_3$ | H | —$CH_2CH_2CH_2CH_2$— | O | phenyl | 4-F | $n_D^{20}$ 1.5553 |
| 768 | $CH_3$ | $CH_3$ | H | —$CH_2CH_2CH_2CH_2$— | O | phenyl | 4-Cl | $n_D^{20}$ 1.5678 |
| 769 | $CH_3$ | $CH_3$ | H | —$CH_2CH_2CH_2CH_2$— | O | phenyl | 4-$OCH_3$ | $n_D^{20}$ 1.5605 |
| 770 | $CH_3$ | $CH_3$ | H | —$CH_2CH_2CH_2CH_2$— | O | 4-$CH_3$-phenyl | H | $n_D^{20}$ 1.5620 |
| 771 | $CH_3$ | $CH_3$ | H | —$CH_2CH_2CH_2CH_2$— | O | 4-$C_4H_9$-t-phenyl | H | $n_D^{20}$ 1.5511 |
| 772 | $CH_3$ | $CH_3$ | H | —$CH_2CH_2CH_2CH_2$— | O | 4-Cl-phenyl | H | $n_D^{20}$ 1.5672 |
| 773 | $CH_3$ | $CH_3$ | H | —$CH_2CH_2CH_2CH_2$— | O | 4-$OCH_3$-phenyl | H | $n_D^{20}$ 1.5653 |
| 774 | $CH_3$ | $CH_3$ | H | —$CH_2CH_2CH_2CH_2$— | O | 3,4-methylenedioxyphenyl | H | $n_D^{20}$ 1.5638 |

TABLE I(b)-continued

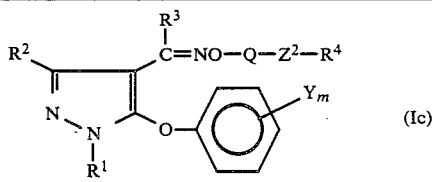

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 775 | $CH_3$ | $CH_3$ | H | $-CH_2CH_2CH_2CH_2-$ | O | phenyl | H | $n_D^{20}$ 1.5763 |
| 776 | $CH_3$ | $CH_3$ | H | $-CH_2CH=CHCH_2-$ | O | 4-Cl-phenyl | H | $n_D^{20}$ 1.5712 |
| 777 | $CH_3$ | $CH_3$ | H | $-CH_2CH_2CH_2CH_2CH_2-$ | O | phenyl | 4-$OCH_3$ | $n_D^{20}$ 1.5635 |
| 778 | $CH_3$ | $CH_3$ | H | $-CH_2CH_2CH_2CH_2CH_2-$ | O | 4-$C_4H_9$-t-phenyl | H | $n_D^{10}$ 1.5511 |
| 779 | $CH_3$ | $CH_3$ | H | $-CH_2CH_2CH_2CH_2CH_2-$ | O | 4-Cl-phenyl | H | $n_D^{10}$ 1.5671 |
| 780 | $CH_3$ | $CH_3$ | H | $-CH_2CH_2CH_2CH_2CH_2CH_2-$ | O | phenyl | H | $n_D^{20}$ 1.5583 |
| 781 | $CH_3$ | $CH_3$ | H | $-CH_2CH_2CH_2CH_2CH_2CH_2-{1ab,4}$ | O | 4-$C_4H_9$-t-phenyl | H | $n_D^{10}$ 1.5478 |
| 782 | $CH_3$ | $CH_3$ | H | $-CH_2CH_2CH_2CH_2CH_2CH_2-$ | O | 4-Cl-phenyl | H | $n_D^{10}$ 1.5631 |
| 783 | $CH_3$ | $CH_3$ | H | $-CH_2CH_2-$ | O | naphthyl | 4-Cl | m.p. 110.1 |
| 784 | $CH_3$ | $CH_3$ | H | $-CH_2CH_2-$ | O | naphthyl | H | m.p. 107.4 |
| 785 | $CH_3$ | $CH_3$ | H | $-CH_2CH_2-$ | O | naphthyl | H | $n_D^{20}$ 1.6107 |
| 786 | $CH_3$ | $CH_3$ | H | $-CH_2CH_2-$ | O | $-COCH_3$ | H | $n_D^{20}$ 1.5411 |

TABLE I(b)-continued

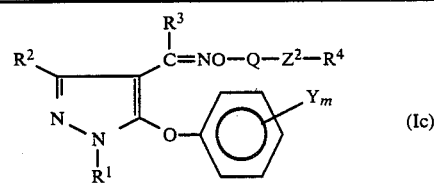

(Ic)

This formula corresponds to the general formula (I) wherein $Z^1$ is an oxygen atom.

| Compound No. | $R^1$ | $R^2$ | $R^3$ | Q | $Z^2$ | $R^4$ | $Y_m$ | Physical property m.p. (°C.) or refractive index |
|---|---|---|---|---|---|---|---|---|
| 787 | $CH_3$ | $CH_3$ | H | $-CH_2CH_2-$ | O | $-CO-\phantom{xxx}\bigcirc$ | H | $n_D^{20}$ 1.5632 |
| 788 | $CH_3$ | $CH_3$ | H | $-CH_2CH_2-$ | O | $-C_4H_9-t$ | H | $n_D^{20}$ 1.5273 |
| 789 | $CH_3$ | $CH_3$ | H | $-CH_2CH_2-$ | O | $-C_2H_5$ | H | $n_D^{20}$ 1.5407 |

TABLE I(c)

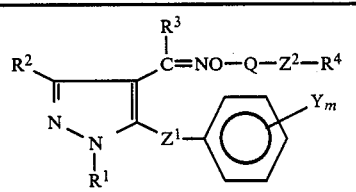

(I)

| Compound No. | $R^1$ | $R^2$ | $R^3$ | $-Q-Z^2-R^4$ | $Y_m$ | Physical property m.p. (°C.) or refractive index |
|---|---|---|---|---|---|---|
| 790 | $CH_3$ | $CH_3$ | H | $-CH_3$ | H | m.p. 70.2 |
| 791 | $CH_3$ | $CH_3$ | H | $-C_2H_5$ | H | $n_D^{20}$ 1.5504 |
| 792 | $CH_3$ | $CH_3$ | H | $-CH_2CH_2Br$ | H | $n_D^{20}$ 1.5721 |
| 793 | $CH_3$ | $CH_3$ | H | $-C_3H_7-i$ | H | $n_D^{20}$ 1.5432 |
| 794 | $CH_3$ | $CH_3$ | H | $-CH_2CH=CH_2$ | H | $n_D^{20}$ 1.5560 |
| 795 | $CH_3$ | $CH_3$ | H | $-CH_2C\equiv CH$ | 4-Cl | $n_D^{20}$ 1.5670 |
| 796 | $CH_3$ | $CH_3$ | H | $-CH_2CH_2CH_2CH_2Br$ | H | $n_D^{20}$ 1.5618 |
| 797 | $CH_3$ | $CH_3$ | H | $-CH_2CH=C(CH_3)_2$ | H | $n_D^{20}$ 1.5494 |
| 798 | $CH_3$ | $CH_3$ | H | $-CH_2CH_2CH_2CH_2CH_2Br$ | H | $n_D^{20}$ 1.5571 |
| 799 | $CH_3$ | $CH_3$ | H | $-CH_2CH_2CH_2CH_2CH_2CH_2Br$ | H | $n_D^{20}$ 1.5522 |
| 800 | $CH_3$ | $CH_3$ | H | $-CH_2CH=\overset{\underset{\mid}{CH_3}}{C}CH_2CH_2CH=C(CH_3)_2$ | H | $n_D^{20}$ 1.5267 |
| 801 | $CH_3$ | $CH_3$ | H | $-CH_2CH=\overset{\underset{\mid}{CH_3}}{C}CH_2CH_2CH=C(CH_3)_2$ | 4-F | $n_D^{20}$ 1.5294 |
| 802 | $CH_3$ | $CH_3$ | H | $-CH_2CH=\overset{\underset{\mid}{CH_3}}{C}CH_2CH_2CH=C(CH_3)_2$ | 4-Cl | $n_D^{20}$ 1.5290 |
| 803 | $CH_3$ | $CH_3$ | H | $-CH_2CH_2N\diagdown O$ (morpholine) | H | $n_D^{20}$ 1.5408 |
| 804 | $CH_3$ | $CH_3$ | H | $-CH_2CCl=CHCl$ | H | $n_D^{20}$ 1.5578 |
| 805 | $CH_3$ | $CH_3$ | H | $-\underset{\underset{CH_3}{\mid}}{CH}-\bigcirc-Cl$ | 4-Cl | $n_D^{20}$ 1.5653 |
| 806 | $CH_3$ | $CH_3$ | H | $-\underset{\underset{CH_3}{\mid}}{CH}-\bigcirc-C_4H_9-t$ | H | $n_D^{20}$ 1.5470 |

TABLE I(c)-continued (I)

| Compound No. | R¹ | R² | R³ | —Q—Z²—R⁴ | $Y_m$ | Physical property m.p. (°C.) or refractive index |
|---|---|---|---|---|---|---|
| 807 | CH₃ | CH₃ | H | —CH(i-C₃H₇)—C₆H₅ | H | $n_D^{20}$ 1.5662 |
| 808 | CH₃ | CH₃ | H | —CH(i-C₃H₇)—C₆H₄—Cl | H | $n_D^{20}$ 1.5675 |
| 809 | CH₃ | CH₃ | H | —CH(i-C₃H₇)—C₆H₄—t-C₄H₉ | H | m.p. 86.9 |
| 810 | CH₃ | CH₃ | H | —CH(C₆H₅)—C₆H₄—t-C₄H₉ | H | $n_D^{20}$ 1.5716 |
| 811 | CH₃ | CH₃ | H | —CH₂CH₂—C₆H₅ | H | $n_D^{20}$ 1.5674 |
| 812 | CH₃ | CH₃ | H | —CH₂CH₂—C₆H₄—F | H | $n_D^{20}$ 1.5602 |
| 813 | CH₃ | CH₃ | H | —CH₂CH₂—C₆H₄—F | 4-F | $n_D^{20}$ 1.5524 |
| 814 | CH₃ | CH₃ | H | —CH₂CH₂—C₆H₄—F | 4-Cl | $n_D^{20}$ 1.5621 |
| 815 | CH₃ | CH₃ | H | —CH₂CH₂—C₆H₄—F | 4-OCH₃ | $n_D^{20}$ 1.5588 |

TABLE I(c)-continued (I)

| Compound No. | R¹ | R² | R³ | —Q—Z²—R⁴ | $Y_m$ | Physical property m.p. (°C.) or refractive index |
|---|---|---|---|---|---|---|
| 816 | CH₃ | CH₃ | H | —CH₂CH₂—⟨phenyl⟩—C₄H₉—t | H | $n_D^{20}$ 1.5653 |
| 817 | CH₃ | CH₃ | H | —CH₂CH₂—⟨phenyl⟩—C₄H₉—t | 4-F | $n_D^{20}$ 1.5547 |
| 818 | CH₃ | CH₃ | H | —CH₂CH₂—⟨phenyl⟩—C₄H₉—t | 4-Cl | $n_D^{20}$ 1.5688 |
| 819 | CH₃ | CH₃ | H | —CH₂CH₂—⟨phenyl⟩—C₄H₉—t | 4-OCH₃ | $n_D^{20}$ 1.5643 |
| 820 | CH₃ | CH₃ | H | —CH₂CH₂—⟨phenyl⟩—OCH₃ | H | $n_D^{20}$ 1.5755 |
| 821 | CH₃ | CH₃ | H | —CH₂CH₂CH₂—⟨phenyl⟩ | H | $n_D^{20}$ 1.5747 |
| 822 | CH₃ | CH₃ | H | —CH₂CH₂CH₂—⟨phenyl⟩—C₂H₅ | H | $n_D^{20}$ 1.5654 |
| 823 | CH₃ | CH₃ | H | —CH₂CH₂CH₂—⟨phenyl⟩—Cl | H | $n_D^{20}$ 1.5757 |
| 824 | CH₃ | CH₃ | H | —CH₂CH₂CH₂—⟨phenyl⟩—Cl | 4-Cl | $n_D^{20}$ 1.5751 |
| 825 | CH₃ | CH₃ | H | —CH₂CH₂CH₂—⟨phenyl⟩—Cl | 4-OCH₃ | $n_D^{20}$ 1.5733 |
| 826 | CH₃ | CH₃ | H | —CH₂CH₂CH₂—⟨phenyl⟩—C₄H₉—t | H | $n_D^{20}$ 1.5543 |

TABLE I(c)-continued

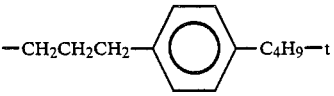

(I)

| Compound No. | R[1] | R[2] | R[3] | —Q—Z[2]—R[4] | $Y_m$ | Physical property m.p. (°C.) or refractive index |
|---|---|---|---|---|---|---|
| 827 | CH$_3$ | CH$_3$ | H | —CH$_2$CH$_2$CH$_2$—⌬—C$_4$H$_9$—t | 4-F | $n_D^{20}$ 1.5450 |
| 828 | CH$_3$ | CH$_3$ | H | —CH$_2$CH$_2$CH$_2$—⌬—C$_4$H$_9$—t | 4-Cl | $n_D^{20}$ 1.5578 |
| 829 | CH$_3$ | CH$_3$ | H | —CH$_2$CH$_2$CH$_2$—⌬—C$_4$H$_9$—t | 4-OCH$_3$ | $n_D^{20}$ 1.5539 |
| 830 | CH$_3$ | CH$_3$ | H | —CH$_2$CH$_2$CH$_2$—⌬—C$_5$H$_{11}$—n | H | $n_D^{20}$ 1.5463 |
| 831 | CH$_3$ | CH$_3$ | H | —CH$_2$CH$_2$CH$_2$—⌬—OCH$_3$ | H | $n_D^{20}$ 1.5695 |
| 832 | CH$_3$ | CH$_3$ | H | —CH$_2$CH$_2$CH$_2$—⌬—C$_5$H$_{11}$—n | 4-F | $n_D^{20}$ 1.5332 |
| 833 | CH$_3$ | CH$_3$ | H | —CH$_2$CH$_2$CH$_2$—⌬—OCH$_3$ | 4-F | $n_D^{20}$ 1.5613 |
| 834 | CH$_3$ | CH$_3$ | H | —CH$_2$CH$_2$CH$_2$—⌬—OCH$_3$ | 4-Cl | $n_D^{20}$ 1.5760 |
| 835 | CH$_3$ | CH$_3$ | H | —CH$_2$CH$_2$CH$_2$—⌬—OCH$_3$ | 4-OCH$_3$ | $n_D^{20}$ 1.5690 |
| 836 | CH$_3$ | CH$_3$ | H | —CH$_2$CH$_2$CH$_2$—⌬—SCF$_2$CF$_2$H | H | $n_D^{20}$ 1.5545 |
| 837 | CH$_3$ | CH$_3$ | H | —CH$_2$CH$_2$CH$_2$—⌬—COOCH$_3$ | H | $n_D^{20}$ 1.5722 |

TABLE 1(c)-continued (I)

| Compound No. | R¹ | R² | R³ | —Q—Z²—R⁴ | $Y_m$ | Physical property m.p. (°C.) or refractive index |
|---|---|---|---|---|---|---|
| 838 | CH₃ | CH₃ | H | —CH₂CH₂CH₂—⟨⟩—COOC₄H₉—t | H | $n_D^{20}$ 1.5577 |
| 839 | CH₃ | CH₃ | H | —CH₂CH₂CH₂—⟨⟩—C₆H₁₁ | H | $n_D^{20}$ 1.5660 |
| 840 | CH₃ | CH₃ | H | —CH₂CH₂CH₂—⟨⟩—C₆H₁₁ | 4-F | $n_D^{20}$ 1.5576 |
| 841 | CH₃ | CH₃ | H | —CH₂CH=CH—⟨⟩ | 4-Cl | $n_D^{20}$ 1.5960 |
| 842 | CH₃ | CH₃ | H | —CH₂CH=CH—⟨⟩—F | H | $n_D^{20}$ 1.5647 |
| 843 | CH₃ | CH₃ | H | —CH₂CH=CH—⟨⟩—F | 4-Cl | $n_D^{20}$ 1.5829 |
| 844 | CH₃ | CH₃ | H | —CH₂CH=CH—⟨⟩—F | 4-OCH₃ | $n_D^{20}$ 1.5732 |
| 845 | CH₃ | CH₃ | H | —CH₂CH=CH—⟨⟩—Cl | H | $n_D^{20}$ 1.5972 |
| 846 | CH₃ | ⟨C₆H₅⟩ | H | —CH₂CH=CH—⟨⟩—Cl | 4-Cl | $n_D^{20}$ 1.5980 |
| 847 | CH₃ | CH₃ | H | —CH₂CH=CH—⟨⟩—Cl | H | m.p. 119.9 |
| 848 | CH₃ | CH₃ | H | —CH₂C≡C—⟨⟩ | H | $n_D^{20}$ 1.6045 |

TABLE I(c)-continued $$\begin{array}{c} R^3 \\ | \\ R^2 \diagdown C=NO-Q-Z^2-R^4 \\ \| \\ C \\ N \diagup \diagdown Z^1 - \text{(Ph)} - Y_m \\ | \\ N \\ | \\ R^1 \end{array}$$ (I)

| Compound No. | $R^1$ | $R^2$ | $R^3$ | $-Q-Z^2-R^4$ | $Y_m$ | Physical property m.p. (°C.) or refractive index |
|---|---|---|---|---|---|---|
| 849 | CH$_3$ | CH$_3$ | H | $-CH_2C\equiv C-\text{Ph}$ | 4-Cl | $n_D^{20}$ 1.5886 |
| 850 | CH$_3$ | CH$_3$ | H | $-CH_2C\equiv C-\text{Ph}-F$ | H | Paste |
| 851 | CH$_3$ | CH$_3$ | H | $-CH_2C\equiv C-\text{Ph}-F$ | 4-F | $n_D^{20}$ 1.5828 |
| 852 | CH$_3$ | CH$_3$ | H | $-CH_2C\equiv C-\text{Ph}-Cl$ | H | Paste |
| 853 | CH$_3$ | CH$_3$ | H | $-CH_2C\equiv C-\text{Ph}-Cl$ | 4-F | Paste |
| 854 | CH$_3$ | CH$_3$ | H | $-CH_2C\equiv C-\text{Ph}-Cl$ | 4-Cl | Paste |
| 855 | CH$_3$ | CH$_3$ | H | $-CH_2C\equiv C-\text{Ph}-Cl$ | 4-OCH$_3$ | $n_D^{20}$ 1.5815 |
| 856 | CH$_3$ | CH$_3$ | Ph | $-CH_3$ | H | $n_D^{20}$ 1.5822 |
| 857 | CH$_3$ | CH$_3$ | Ph | $-CH_2CH=CH_2$ | H | $n_D^{20}$ 1.5800 |

Note 1. $^1$HNMR value (CDCl$_3$, TMS) of Compound No. 180: 1.62 (6H, s), 2.33 (3H, s), 3.53 (3H, s), 4.83 (2H, d, J=48Hz), 4.95 (2H, s), 6.7–7.9 (9H, m), 7.75 (1H, s)
Note 2. $^1$HNMR value (CDCl$_3$, TMS) of compound No. 299: 1.37 (6H, s), 2.34 (3H, s), 3.55 (3H, s), 4.53 (2H, d, J=47.5Hz), 4.95 (2H, s), 6.7–7.4 (9H, m), 7.76 (1H, s)

Production of the compounds of the present invention will be illustrated with reference to the following examples, but it is not limited to these examples.

EXAMPLE 1

Methyl 4-[(1,3-dimethyl-5-phenoxyprazol-4-yl)methyleneaminooxymethyl]benzoate (compound No. 16)

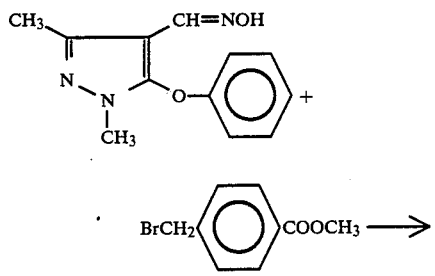

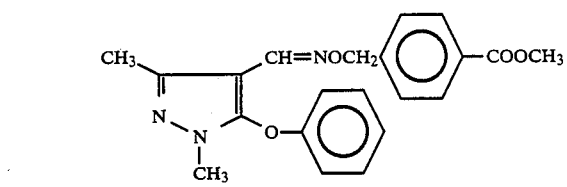

2.0 Grams (0.00865 mole) of 1,3-dimethyl-5-phenoxypyrazole-4-carbaldehyde oxime, 1.98 g (0.00865 mole) of methyl 4-bromomethylbenzoate and 1.19 g (0.009 mole) of potassium carbonate were added to 50 ml of acetone, and the resulting mixture was heated under reflux for 8 hours. After completion of the reaction, acetone was removed by evaporation under reduced pressure, after which water was added to the residue and extraction was carried out with ethyl acetate. The ethyl acetate extract was washed with water and dried, and ethyl acetate was removed by evaporation to obtain an oily product. This oily product was column-chromatographed on silica gel to obtain 2.0 g of the desired product.

Yield 61%. $n_D^{20}$ 1.5612.

EXAMPLE 2

Tert-butyl 4-[(1,3-dimethyl-5-phenoxypyrazol-4-yl)methyleneaminooxymethyl]benzoate (compound No. 60)

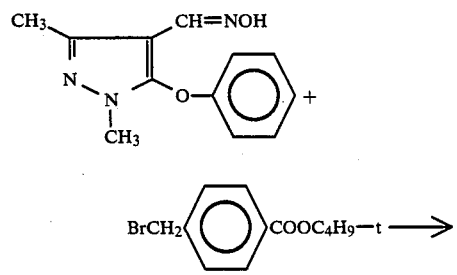

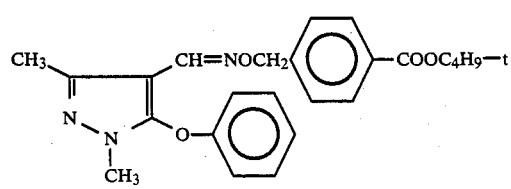

2.0 Grams (0.00855 mole) of 1,3-dimethyl-5-phenoxypyrazole-4-carbaldehyde oxime was dissolved in 20 ml of dimethyl sulfoxide, and after adding 0.65 g (0.0116 mole) of powdery potassium hydroxide, the resulting mixture was stirred at 30° C. for 30 minutes. To this solution was added 2.32 g (0.00855 mole) of tert-butyl 4-bromomethylbenzoate, and reaction was carried out at from 50° to 60° C. for 1 hour. After completion of the reaction, water was added to the reaction solution which was then extracted with ethyl acetate. The ethyl acetate extract was washed with water and dried, and ethyl acetate was removed by evaporation to obtain crude crystals. The crystals were recrystallized from methanol to obtain 2.4 g of the desired compound.

Yield 67.0%. m.p. 101.7° C.

EXAMPLE 3

Methyl 2-[{5-(4-chlorophenoxy)-1,3-dimethylpyrazol-4-yl}methyleneaminoxymethyl]benzoate (compound No. 3)

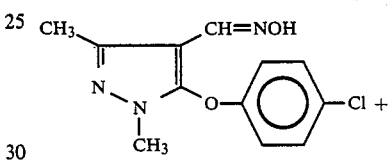

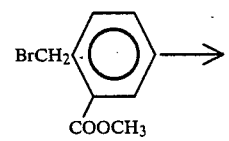

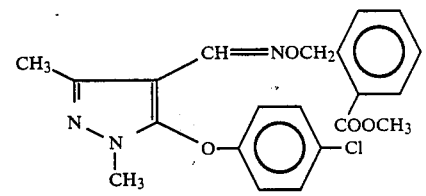

2.0 Grams (0.00755 mole) of 5-(4-chlorophenoxy)-1,3-dimethyl-pyrazole-4-carbaldehyde oxime was dissolved in 20 ml of dimethylformamide, and after adding 0.5 g (0.0125 mole) of powdery sodium hydroxide, the resulting mixture was thoroughly stirred. To this solution was added 1.73 g (0.00755 mole) of methyl 2-bromomethylbenzoate, and reaction was carried out at from 70° to 80° C. for 5 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 2.0 g cf the desired compound.

Yield 64.0%. $n_D^{20}$ 1.5788.

EXAMPLE 4

Isopropyl 4-[(1,3-dimethyl-5-phenylthiopyrazol-4-yl)methyleneaminooxymethyl]benzoate (compound No. 174)

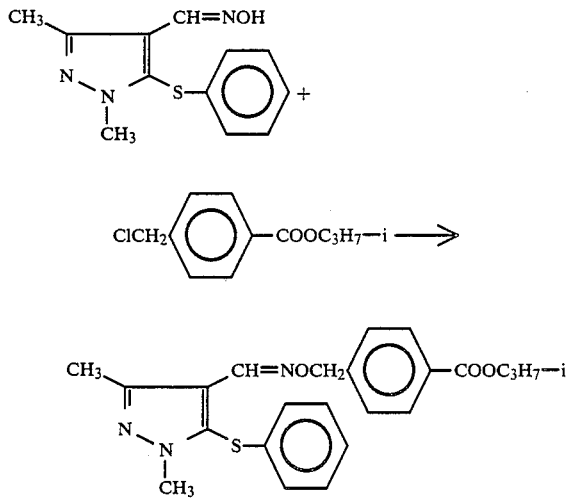

3.0 Grams (0.0121 mole) of 1,3-dimethyl-5-phenylthiopyrazole-4-carbaldehyde oxime, 2.57 g (0.0121 mole) of isopropyl 4-chloromethylbenzoate and 2.8 g (0.026 mole) of sodium carbonate were added to 50 ml of methyl ethyl ketone, and the resulting mixture was heated under reflux for 5 hours. After completion of the reaction, methyl ethyl ketone was removed by evaporation under reduced pressure, after which water was added to the residue and extraction was carried out with ethyl acetate. The ethyl acetate extract was washed with water and dried, and ethyl acetate was removed by evaporation to obtain an oily product. This oily product was column-chromatographed on silica gel to obtain 3.0 g of the desired compound.

Yield 59.0%. $n_D^{20}$ 1.5821.

EXAMPLE 5

Tert-butyl 4-[1-(1,3-dimethyl-5-phenoxypyrazol-4-yl)-ethylideneaminooxymethyl]benzoate (compound No. 1669

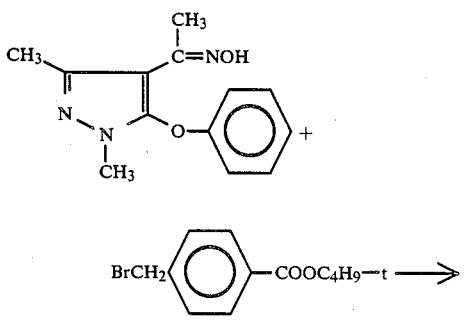

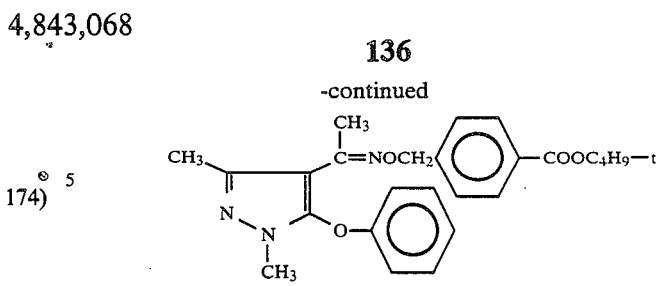

2.0 Grams (0.00816 mole) of methyl 1,3-dimethyl-5-phenoxy-pyraxol-4-yl ketone oxime, 2.2 g (0.00816 mole) of tert-butyl 4-bromomethylbenzoate and 4.0 g (0.028 mole) of potassium carbonate were added to 50 ml of acetonitrile, and the resulting mixture was heated under reflux for 5 hours. After completion of the reaction, acetonitrile was removed by evaporation under reduced pressure, after which water was added to the residue and extraction was carried out with ethyl acetate. The ethyl acetate extract was washed with water and dried, and ethyl acetate was removed by evaporation to obtain crude crystals. The crystals were recrystallized from methanol to obtain 2.8 g of the desired compound.

Yield 79.0%. m.p. 94.4° C.

EXAMPLE 6

Cyclohexyl 4-[{5-(4-fluorophenoxy)-1,3-dimethylpyrazol-4-yl}methyleneaminooxymethyl]benzoate (compound No. 119)

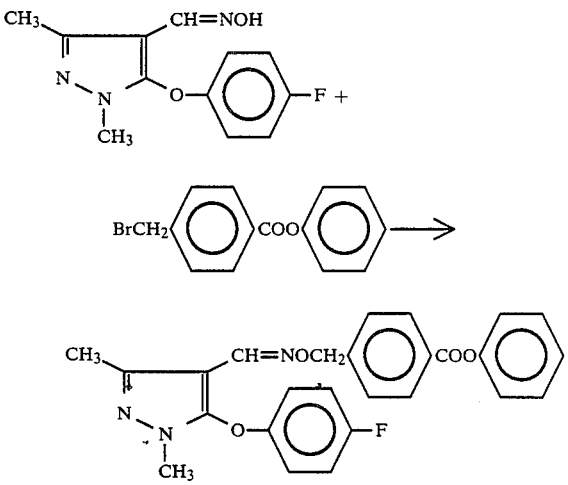

2.0 Grams (0.008 mole) of 5-(4-fluorophenoxy)-1,3-dimethylpyrazole-4-carbaldehyde oxime and 0.5 g (0.0125 mole) of powdery sodium hydroxide were added to 50 ml of dimethyl sulfoxide, and the resulting mixture was stirred for 30 minutes. To this solution was added 2.38 g (0.008 mole) of cyclohexyl 4-bromomethylbenzoate, and reaction was carried out at from 70° to 80° C. for 6 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 3.0 g of the desired compound.

Yield 80.0%. $n_D^{20}$ 1.5863.

EXAMPLE 7

Tert-butyl 4-[(1-methyl-5-phenoxypyrazol-4-yl)methyleneaminooxymethyl]benzoate (compound No. 174)

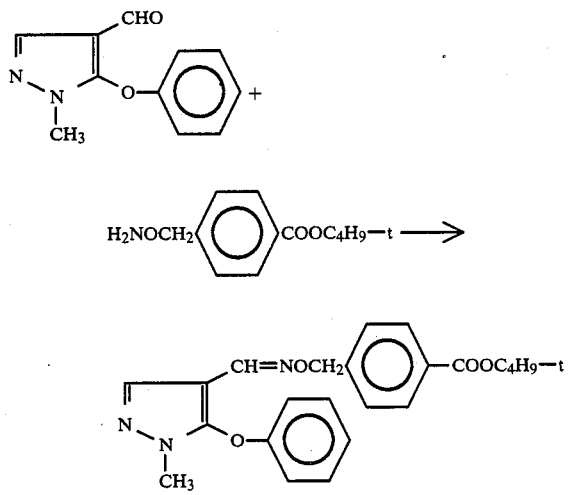

1.0 Gram (0.0049 mole) of 1-methyl-5-phenoxypyrazole-4-carbaldehyde and 1.1 g (0.0049 mole) of tert-butyl 4-aminooxymethylbenzoate were added to 20 ml of ethanol, and the resulting mixture was heated under reflux to carry out reaction. After completion of the reaction, ethanol was removed by evaporation, after which water was added to the residue and extraction was carried out with ethyl acetate. The ethyl acetate extract was washed with water and dried, and ethyl acetate was removed by evaporation to obtain an oily product. This oily product was column-chromatographed on silica gel to obtain 1.6 g of the desired compound.

Yield 80%. Form of product: paste.

NMR (CDCl$_3$, TMS): δ (ppm) 1.56 (s, 9H), 3.60 (s, 3H), 4.96 (s, 2H), 6.60–7.40 (m, 7H), 7.63 (s, 1H), 7.66 (s, 1H), 7.75–8.00 (m, 2H).

EXAMPLE 8

2-phenoxyethyl 4-[{5-(4-fluorophenoxy)-1,3-dimethylpyrazol-4-yl}methyleneaminooxymethyl]benzoate (compound No. 142)

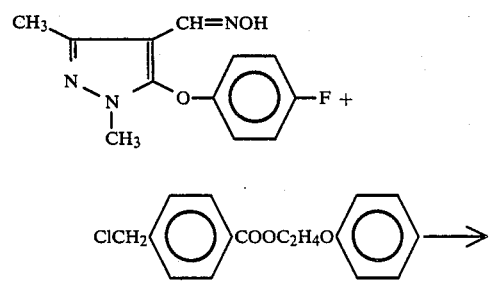

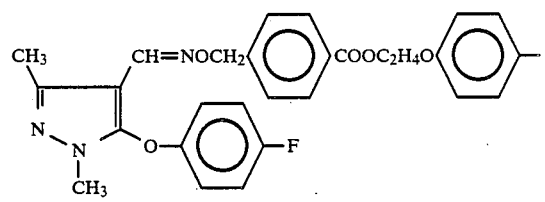

2.0 Grams (0.008 mole) of 5-(4-fluorophenoxy)-1,3-dimethylpyrazole-4-carbaldehyde oxime was dissolved in 20 ml of dimethyl sulfoxide, and after adding 0.65 g (0.0116 mole) of powdery potassium hydroxide, the resulting solution was stirred at 30° C. for 30 minutes. To this solution was added 2.5 g (0.00865 mole) of 2-phenoxyethyl 4-chloromethylbenzoate, and reaction was carried out at from 50° to 60° C. for 1 hour. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 3.0 g of the desired compound.

Yield 75.0%. n$_D^{20}$ 1.5655.

EXAMPLE 9

Phenyl 4-[(1,3-dimethyl-5-phenoxypyrazol-4-yl)methyleneaminooxy]benzoate (compound No. 161)

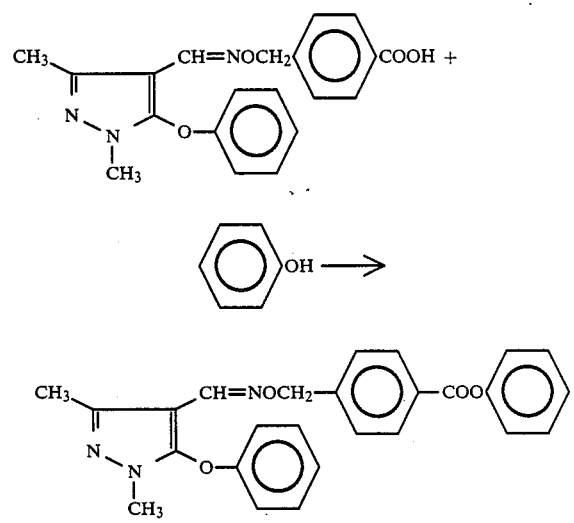

1.0 Gram (0.0027 mole) of 4-[(1,3-dimethyl-5-phenoxypyrazol-4-yl)methyleneaminooxymethyl]benzoic acid, 0.25 g (0.0027 mole) of phenol and 0.7 g (0.0027 mole) of triphenylphosphine were added to 50 ml of ether, and the resulting mixture was stirred. To this solution was added 0.47 g (0.0027 mole) of diethyl azodicarboxylate, and the resulting solution was heated under reflux for 3 hours. After completion of the reaction, the ether layer was filtered, and ether was removed by evaporation to obtain an oily product. This oily product was column-chromatographed on silica gel to obtain 0.9 g of the desired compound.

Yield 76.0%. n$_D^{20}$ 1.5656.

EXAMPLE 10

4-[(1,3-Dimethyl-5-phenoxypyrazol-4-yl)-methyleneaminooxymethyl]benzoic acid (compound No. 14)

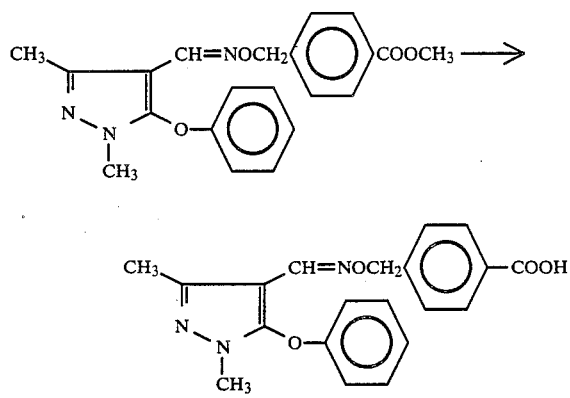

Three grams (0.0079 mole) of methyl 4-[(1,3-dimethyl-5-phenoxypyrazol-4-yl)methyleneaminooxymethyl]-benzoate was dissolved in 20 ml of methanol and a solution of 0.24 g of lithium hydroxide in 5 ml of water was added. Reaction was then carried out at room temperature for 2 hours. After completion of the reaction, methanol was removed by evaporation, and after adding water, the solution was acidified with hydrochloric acid to precipitate crystals. The crystals were collected by filtration to obtain 2 g of the desired compound.

Yield 70%. m.p. 183.3° C.

EXAMPLE 11

Sodium 4-[(1,3-dimethyl-5-phenoxypyrazol-4-yl)methyleneaminooxymethyl]benzoate (compound No. 15)

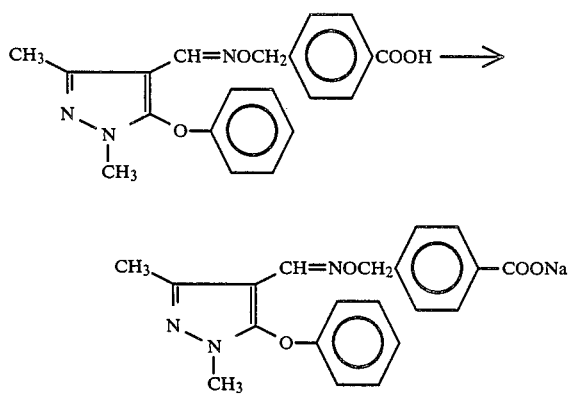

1.0 Gram (0.0027 mole) of 4-[(1,3-dimethyl-5-phenoxypyrazol-4-yl)methyleneaminooxymethyl]benzoic acid and 0.07 g (0.0028 mole) of sodium hydroxide were added to 10 ml of water, and the resulting mixture was stirred for 2 hours. After completion of the reaction, water was removed by evaporation under reduced pressure to obtain the desired compound in a quantitative yield.

m.p. >300° C.

EXAMPLE 12

1,3-Dimethyl-5-phenoxypyrazole-4-carbaldehyde oxime O-benzyl ether (compound No. 181)

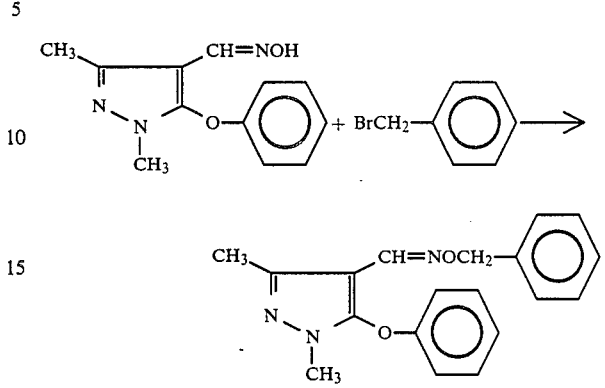

2.0 Grams (0.00866 mole) of 1,3-dimethyl-5-phenoxypyrazole-4-carbaldehyde oxime, 1.5 g (0.0087 mole) of benzyl bromide and 2.0 g (0.0145 mole) of potassium carbonate were dissolved in 50 ml of acetone, and the resulting solution was heated under reflux for 7 hours. After completion of the reaction, acetone was removed by evaporation under reduced pressure, after which water was added and extraction was carried out with ethyl acetate. The ethyl acetate extract was washed with water and dried, and ethyl acetate was removed by evaporation to obtain an oily product. This oily product was column-chromatographed on silica gel to obtain 2.6 g of the desired compound.

Yield 93.0%. $n_D^{20}$ 1.5517.

EXAMPLE 13

5-(4-Chlorophenoxy)-1,3-dimethylpyrazole-4-carbaldehyde oxime O-4-trifluoromethylbenzyl ether (compound No. 195)

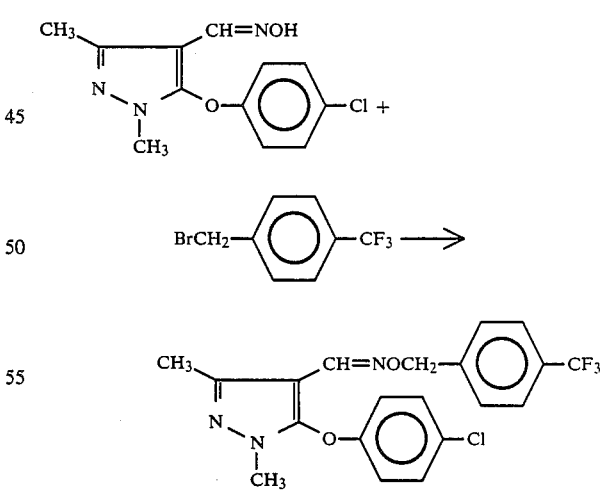

2.0 Grams (0.0075 mole) of 5-(chlorophenoxy)-1,3-dimethylpyrazole-4-carbaldehyde oxime was dissolved in 40 ml of tetrahydrofuran, and after adding 0.19 g (0.0079 mole) of sodium hydride at room temperature, the resulting solution was stirred. Thereafter, 1.7 g (0.0071 mole) of 4-trifluoromethylbenzyl bromide was added, followed by heating under reflux for 3 hours. After completion of the reaction, 100 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 2.7 g of the desired compound.

Yield 85.0%. $n_D^{20}$ 1.5539.

EXAMPLE 14

1,3-Dimethyl-5-phenoxypyrazole-4-carbaldehyde oxime 0-4-(1-cyanocyclopropyl)benzyl ether (compound No. 199)

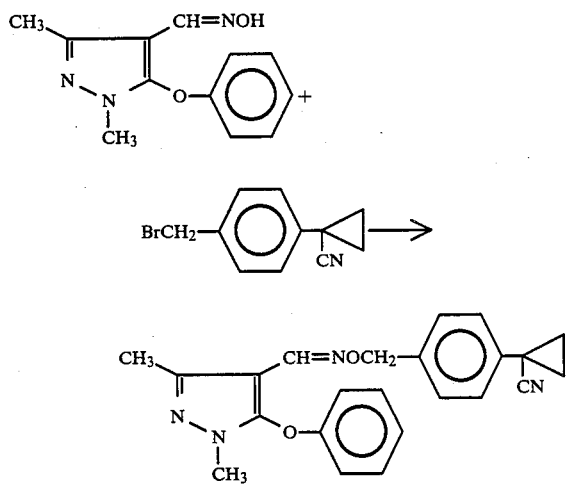

2.0 Grams (0.0086 mole) of 1,3-dimethyl-5-phenoxypyrazole-4-carbaldehyde oxime was dissolved in 30 ml of dimethylformamide, and a solution of 0.5 g (0.0125 mole) of sodium hydroxide in 5 ml of water was added. After stirring was continued for 30 minutes, 2.0 g (0.0086 mole) of 1-(4-bromomethylphenyl)cyclopropane-1-carbonitrile was added to the solution, and reaction was carried out at from 60° to 70° C. for 3 hours. After completion of the reaction, 100 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 2.8 g of the desired compound.

Yield 84.0%. m.p. 109.1° C.

EXAMPLE 15

1,3-Dimethyl-5-phenoxypyrazole-4-carbaldehyde oxime 4-tert-butylbenzyl ether (compound No. 205)

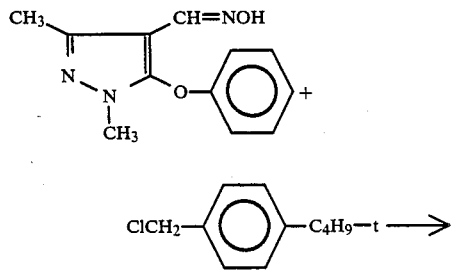

-continued

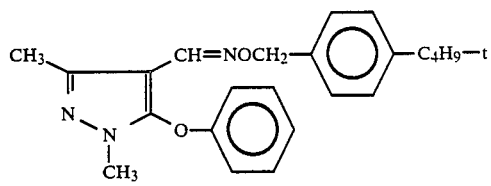

2.0 Grams (0.0086 mole) of 1,3-dimethyl-5-phenoxypyrazole-4-carbaldehyde oxime was dissolved in 20 ml of dimethyl sulfoxide, and after adding 1.0 g (0.0178 mole) of potassium hydroxide, the resulting solution was stirred at room temperature for 30 minutes. To this solution was added 1.5 g (0.0086 mole) of 4-tert-butylbenzyl chloride, and reaction was carried out at from 50° to 60° C. for 3 hours. After completion of the reaction, 100 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 2.4 g of the desired compound.

Yield 74.0%. $n_D^{20}$ 1.5402.

EXAMPLE 16

5-(4-Chlorophenoxy)-1-methylpyrazole-4-carbaldehyde oxime O-benzyl ether (compound No. 279)

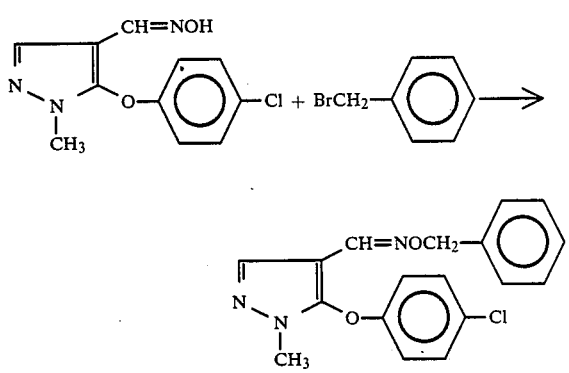

2.0 Grams (0.0092 mole) of 5-(4-chlorophenoxy)-1-methylpyrazole-4-carbaldehyde oxime, 1.5 g (0.0092 mole) of benzyl bromide and 2.0 g (0.0145 mole) of potassium carbonate were dissolved in 50 ml of acetonitrile, and the resulting solution was heated under reflux for 9 hours. After completion of the reaction, 100 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 2.2 g of the desired compound.

Yield 78.0%. $n_D^{20}$ 1.5933.

EXAMPLE 17

1,3-Dimethyl-5-phenoxypyrazol-4-yl methyl ketone oxime O-4-cyclohexylbenzyl ether (compound No. 283)

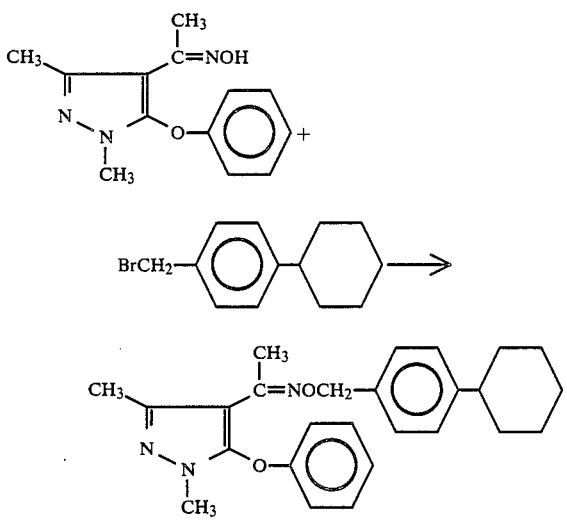

2.0 Grams (0.0040 mole) of 1,3-dimethyl-5-phenoxypyrazol-4-yl methyl ketone oxime was dissolved in 30 ml of dioxane, and 0.1 g (0.0042 mole) of sodium borohydride was added to the solution with thorough stirring. After 30 minutes, 1.6 g (0.0038 mole) of 4-cyclohexylbenzyl bromide was added to the reaction solution which was then heated under reflux for 5 hours. After completion of the reaction, 100 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.2 g of the desired compound.

Yield 72.0%. $n_D^{20}$ 1.5775

EXAMPLE 18

5-(4-Chlorophenylthio)-1,3-dimethylpyrazole-4-carbaldehyde oxime O-benzyl ether (compound No. 290)

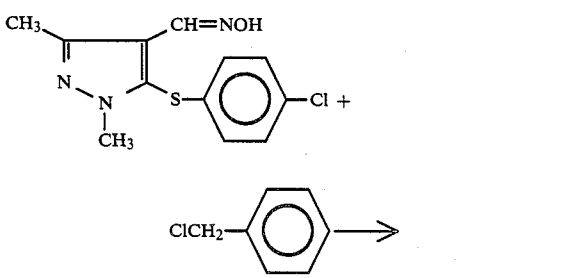

2.0 Grams (0.0071 mole) of 5-(4-chlorophenylthio)-1,3-dimethylpyrazole-4-carbaldehyde oxime was dissolved in 20 ml of dimethyl sulfoxide, and to this solution was added a solution of 0.5 g (0.009 mole) of potassium hydroxide in 5 ml of water. After thorough stirring, 0.9 g (0.0071 mole) of benzyl choride was added, and reaction was carried out at from 60° to 70° C. for 2 hours. After completion of the reaction, 100 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 2.3 g of the desired compound.

Yield 87.0%. $n_D^2$ 1.5562.

EXAMPLE 19

5-(4-Methoxyphenoxy)-1,3-dimethylpyrazole-4-carbaldehyde oxime O-4-(1-cyanocyclopentyl)benzyl ether (compound No. 238)

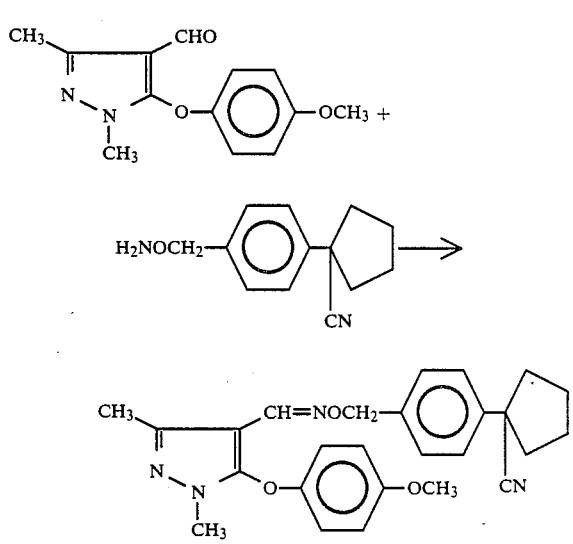

2.0 Grams (0.0081 mole) of 1,3-dimethyl-5-(4-methoxyphenoxy)pyrazole-4-carbaldehyde was dissolved in 50 ml of ethanol, and 1.7 g (0.0081 mole) of O-4-(1-cyanocyclopentyl)benzylhydroxylamine was added, after which reaction was carried out at from 50° to 60° C. for 3 hours. After completion of the reaction, ethanol was removed by evaporation under reduced pressure, after which water was added and extraction was carried out with ethyl acetate. The ethyl acetate extract was washed with water and dried, and ethyl acetate was removed by evaporation to obtain an oily product. This oily product was column-chromatographed on silica gel to obtain 3.0 g of the desired compound.

Yield 83.0%. $n_D^{20}$ 1.5632.

EXAMPLE 20

1,3-Dimethyl-5-phenoxypyrazole-4-carbaldehyde oxime O-4-(2,2-dibromovinyl)benzyl ether (compound No. 262)

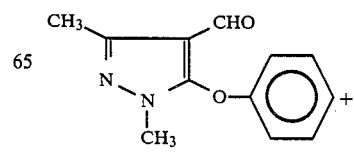

-continued

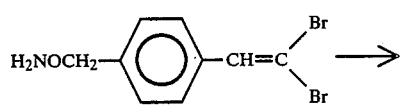

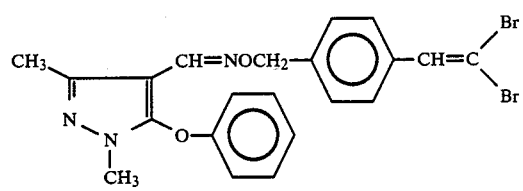

2.0 Grams (0.0093 mole) of 1,3-dimethyl-5-phenoxypyrazole-4-carbaldehyde was dissolved in 50 ml of methanol, and 2.8 g (0.0091 mole) of O-4-(2,2-dibromovinyl)benzylhydroxylamine was added to the solution which was then heated under reflux for 3 hours. After completion of the reaction, methanol was removed by evaporation under reduced pressure, after which water was added and extraction was carried out with ethyl acetate. The ethyl acetate extract was washed with water and dried, and ethyl acetate was removed by evaporation to obtain an oily product. This oily product was column-chromatpgraphed on silica gel to obtain 3.5 g of the desired compound.

Yield 76.0%. m.p. 109.3° C.

EXAMPLE 21

1,3-dimethyl-5-phenoxypyrazole-4-carbaldehyde oxime O-4-fluorobenzyl ether (compound No. 305)

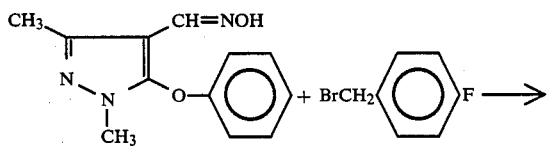

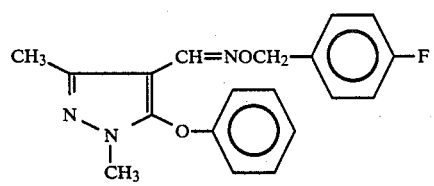

1.0 Gram (0.0043 mole) of 1,3-dimethyl-5-phenoxypyrazole-4-carbaldehyde oxime was dissolved in 20 ml of dimethyl sulfoxide, and after adding 0.3 g (0.0053 mole) of powdery potassium hydroxide, the resulting solution was stirred. To this reaction solution was added 0.81 g (0.0043 mole) of 4-fluorobenzyl bromide, and reaction was carried out at room temperature for 3 hours. After completion of the reaction, 200 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.3 g of the desired compound.

Yield 89%. $n_D^{20}$ 1.5681.

EXAMPLE 22

5-(4-Chlorophenoxy)-1,3-dimethyopyrazole-4-carbaldehyde oxime Ⓞ-2-chlorobenzyl ether (compound No. 309)

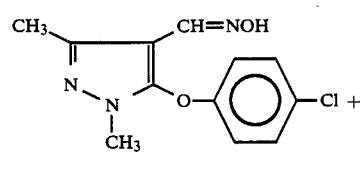

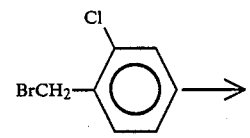

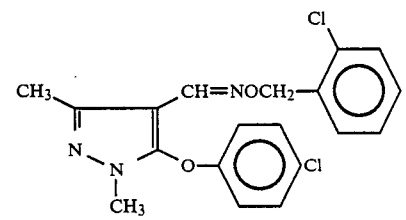

1.0 Gram (0.0038 mole) of 5-(4-chlorophenoxy)-1,3-dimethylpyrazole-4-carbaldehyde oxime, 0.78 g (0.0038 mole) of 2-chlorobenzyl bromide and 1.0g (0.0072 mole) of potassium carbonate were added to 20 ml of acetonitrile, and the resulting mixture was heated under reflux for 6 hours. After completion of the reaction, acetonitrile was removed by evaporation under reduced pressure, after which water was added and extraction was carried out with ethyl acetate. The ethyl acetate extract was washed with water and dried, and ethyl acetate was removed by evaporation to obtain an oily product. This oily product was column-chromatographed on silica gel to obtain 1.2 g of the desired compound.

Yield 81%. $n_D^{20}$ 1.5760.

EXAMPLE 23

5-(4-Chlorophenoxy)-1,3-dimethylpyrazole-4-carbaldehyde oxime O-4-(4-trifluoromethylphenoxy)benzyl ether (compound No. 322)

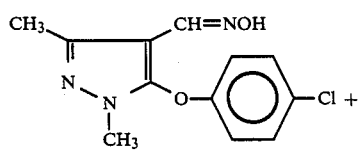

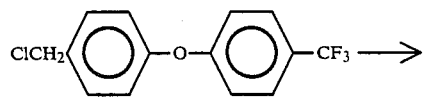

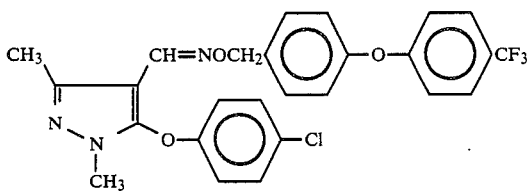

1.0 Gram (0.0038 mole) of 5-(4-chlorophenoxy)-1,3-dimethylpyrazole-4-carbaldehyde oxime, 1.1 g (0.0038 mole) of 4-(4-trifluoromethylphenoxy)benzyl chloride and 0.8 g (0.076 mole) of sodium carbonate were added to 40 ml of acetone, and the resulting mixture was heated under reflux for 8 hours. After completion of the reaction, acetone was removed by evaporation under reduced pressure, after which water was added and extraction was carried out with ethyl acetate. The ethyl acetate extract was washed with water and dried, and ethyl acetate was removed by evaporation to obtain an oily product. This oily product was column-chromatographed on silica gel to obtain 1.4 g of the desired compound.

Yield 72%. m.p. 97.8° C.

EXAMPLE 24

1,3-Dimethyl-5-phenoxypyrazol-4-yl methyl ketone oxime O-4-trimethylsilylbenzyl ether (compound No. 334)

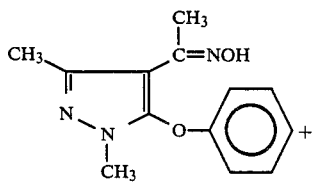

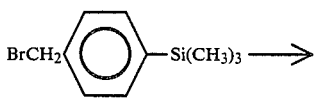

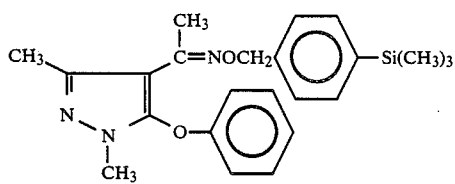

1.0 Gram (0.0041 mole) of 1,3-dimethyl-5-phenoxypyrazol-4-yl methyl ketone oxime was dissolved in 20 ml of dimethyl sulfoxide, and after adding 0.3 g (0.0053 mole) of potassium hydroxide, the resulting solution was stirred. To this reaction solution was added 1.0 g (0.0041 mole) of 4-trimethylsilylbenzyl bromide, and reaction was carried out at room temperarture for 4 hours. After completion of the reaction, 200 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.5 g of the desired compound.

Yield 92%. m.p. 61.2° C.

EXAMPLE 25

1,3-Dimethyl-5-phenoxypyrazol-4-yl ethyl ketone oxime O-4-(1,1,2,2-tetrafluoroethoxy)benzyl ether (compound No. 354)

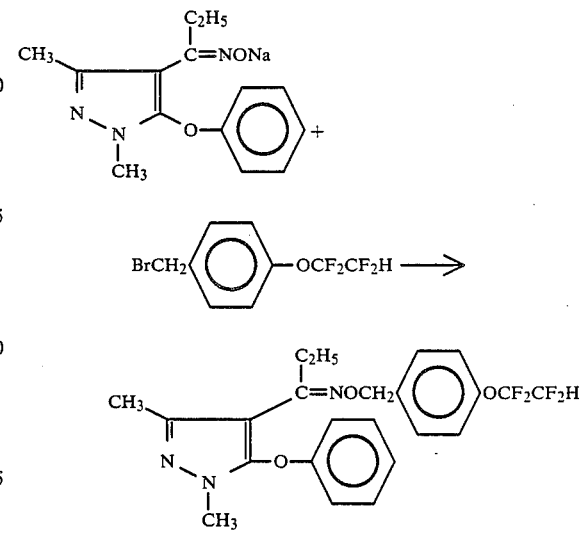

1.0 Gram (0.0035 mole) of sodium salt of 1,3-dimethyl-5-phenoxypyrazol-4-yl ethyl ketone sodium and 1.0 g (0.0035 mole) of 4-(1,1,2,2-tetrafluoroethoxy)benzyl bromide were added to 50 ml of acetone, and the resulting mixture was heated for 5 hours to carry out reaction. After completion of the reaction, acetone was removed by evaporation under reduced presure, after which water was added and extraction was carried out with ethyl acetate. The ethyl acetate extract was washed with water and dried, and ethyl acetate was removed by evaporation to obtain an oily product. This oily product was column-chromatographed on silica gel to obtain 1.3 g of the desired compound.

Yield 76%. $n_D^{20}$ 1.5252.

EXAMPLE 26

5-(4-Methoxyphenoxy)-1,3-dimethylpyrazole-4-carbaldehyde oxime O-4-tert-butoxybenzyl ether (compound No. 366)

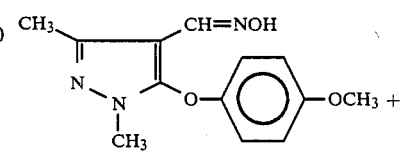

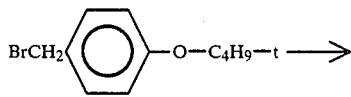

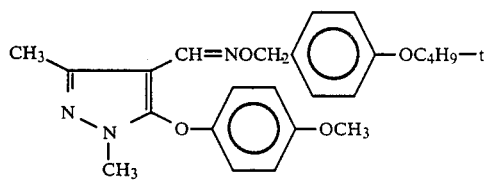

1.0 Gram (0.0038 mole) of 5-(4-methoxyphenoxy)-1,3-dimethyl-pyrazole-4-carbaldehyde oxime was dissolved in 30 ml of tetrahydrofuran, and 0.092 g of sodium hydride was added to synthesize the sodium salt of said oxime. To this solution was added 0.92 g (0.0038 mole) of 4-tert-butoxybenzyl bromide, and reaction was carried out at from 50° to 60° C. for 5 hours. After completion of the reaction, 200 ml of water was added to the reaction solution which was then extracted with ethyl acetate. The ethyl acetate extract was washed with water and dried, and ethyl acetate was removed by evaporation to obtain an oily product. THis oily product was column-chromatographed on silica gel to obtain 1.3 g of the desired compound.

Yield 80%. $n_D^{20}$ 1.5653

EXAMPLE 27

5-(4-Fluorophenoxy)-1,3-dimethylpyrazole-4-carbaldehyde oxime O-3,4-methylenedioxybenzyl ether (compound No. 374)

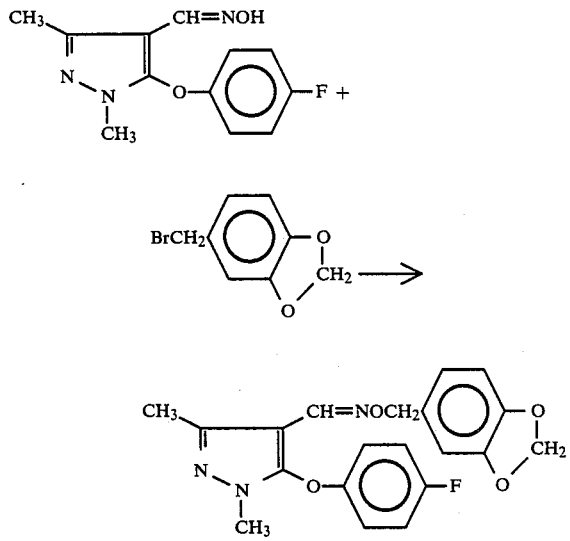

1.0 Gram (0.0040 mole) of 5-(4-fluorophenoxy)-1,3-dimethylpyrazole-4-carbaldehyde oxime was dissolved in 20 ml of dimethylformamide, and after adding 0.2 g (0.005 mole) of sodium hydroxide, the resulting solution was stirred for 30 minutes. To this reaction solution was added 0.86 g (0.004 mole) of 3,4-methylenedioxybenzyl bromide, and reaction was carried out at from 40° to 50° C. for 3 hours. After completion of the reaction, 200 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.1 g of the desired compound.

Yield 72%. $n_D^{20}$ 1.5750.

EXAMPLE 28

5-(4-(Methoxyphenoxy)-1,3-dimethylpyrazole-4-carbaldehyde oxime O-4-methylsulfonylbenzyl ether (compound No. 401)

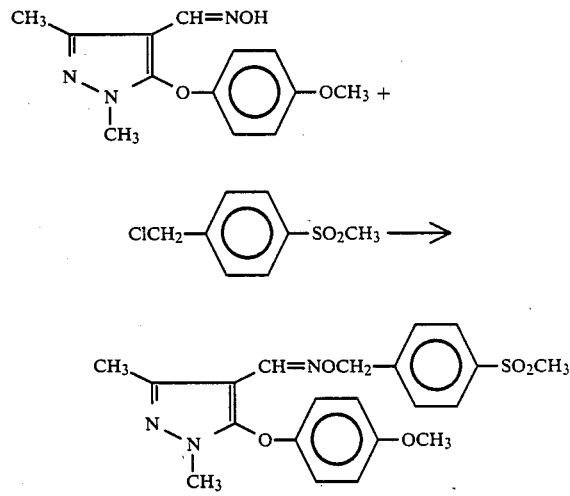

1.0 Gram (0.0038 mole) of 5-(4-methoxyphenoxy)-1,3-dimethylpyrazole-B 4-carbaldehyde oxime and 0.79 g (0.0038 mole) of 4-methylsulfonylbenzyl chloride were dissolved in 30 ml of tetrahydrofuran. To this solution was added 0.6 g (0.0039 mole) of 1,8-diazabicyclo[5.4.0]-7-undecene, and reaction was carried out at from 40° to 50° C. for 5 hours. After completion of the reaction, 200 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.2 g of the desired compound.

Yield 74%. $n_D^{20}$ 1.5866.

EXAMPLE 29

1,3-Dimethyl-5-phenoxypyrazol-4-yl phenyl ketone oxime O-4-difluoromethylthiobenzyl ether (compound No. 426)

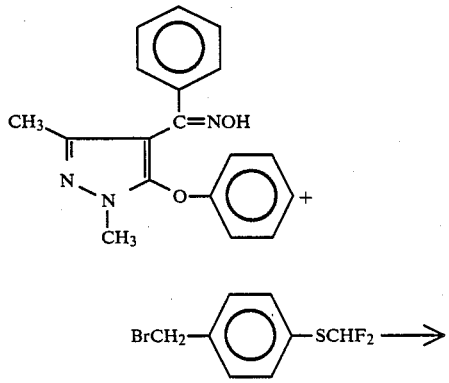

-continued

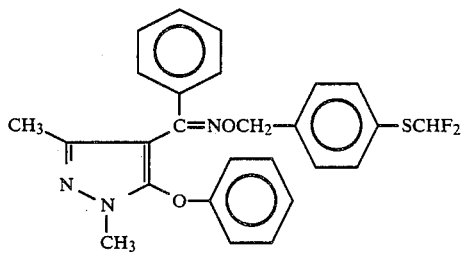

1.0 Gram (0.0033 mole) of 1,3-dimethyl-5-phenoxypyrazol-4-yl phenyl ketone oxime, 0.82 g (0.0033 mole) of 4-difluoromethylthiobenzyl bromide and 1.0 g (0.0072 mole) of potassium carbonate were added to 50 ml of acetone, and the resulting mixture was heated for 6 hours to carry out reaction. After completion of the reaction, acetone was removed by evaporation under reduced pressure, after which water was added and extraction was carried out with ethyl acetate. The ethyl acetate was washed with water and dried, and ethyl acetate was removed by evaporation to obtain an oily product. This oily product was column-chromatographed on silica gel to obtain 1.4 g of the desired compound.

Yield 86%. $n_D^{20}$ 1.5917.

EXAMPLE 30

5-(2-Fluorophenoxy)-1,3-dimethylpyrazole-4-carbaldehyde oxime O-4-(1,1,2,2-tetrafluoroethylthio)benzyl ether (compound No. 467)

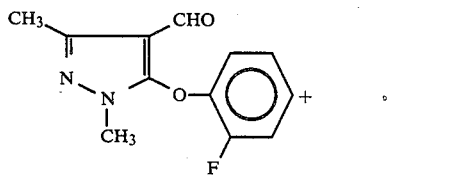

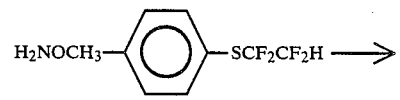

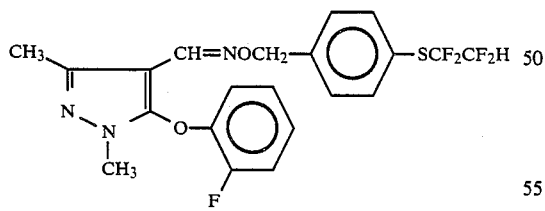

1.1 Gram (0.0043 mole) of 5-(2-fluorophenoxy)-1,3-dimethylpyrazole-4-carbaldehyde was dissolved in 30 ml of ethanol, and 1,1g (0.0043 mole) of O-[4-(1,1,2,2-tetrafluoroethylthio)benzyl]hydroxylaine was added. Reaction was then carried out at from 50° to 60° C. for 2 hours. After completion of the reaction, ethanol was removed by evaporation under reduced pressure, after which water was added and extraction was carried out with chloroform. The chloroform extract was dried, chloroform was removed by evaporation to obtain an oily product. This oily product was column-chromatographed on silica gel to obtain 1.3 g of the desired compound.

Yield 64%. $n_D^{20}$ 1.5462.

EXAMPLE 31

1,3-Dimethyl-5-phenoxypyrazol-4-yl methyl ketone oxime O-4-heptafluoropropylthiobenzyl ether (compound No. 494)

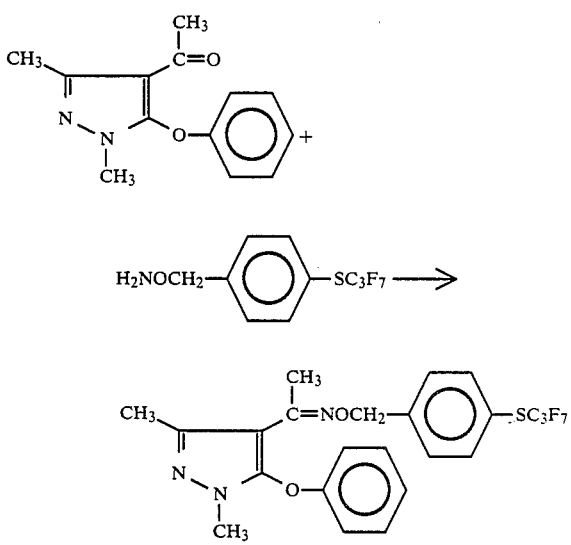

1.0 Gram (0.0043 mole) of 4-acetyl-1,3-dimethyl-5-phenoxypyrazole and 1.4 g (0.0043 mole) of O-(4-heptafluoropropylthiobenzyl)hydroxylamine were added to 30 ml of methanol, and the resulting mixture was heated for 5 hours to carry out reaction. After completion of the reaction, methanol was removed by evaporation under reduced pressure, after which water was added and extraction was carried out with chloroform. The chloroform extract was dried, and chloroform was removed by evaporation to obtain an oily product. This oily product was column-chromatographed on silica gel to 1.4 g of the desired compound.

Yield 60%. $n_D^{20}$ 1.5217.

EXAMPLE 32

S-Ethyl 4-[(1,3-dimethyl-5-phenoxypyrazol-4-yl)methyleneaminoxymethyl]benzothioate (compound No. 516)

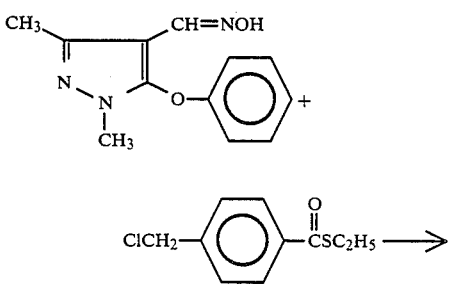

-continued

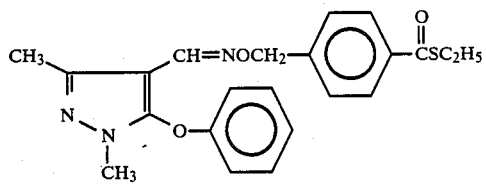

1.0 Gram (0.0043 mole) of 1,3-dimethyl-5-phenoxypyrazole-4-carbaldehyde oxime was dissolved in 20 ml of dimethyl sulfoxide, and after adding 0.3 g (0.0053 mole) of powdery potassium hydroxide, the resulting solution was stirred. To this solution was added 0.92 g (0.0043 mole) of S-ethyl 4-cloromethylbenzothiate, and reaction was carried out at room temperature for 3 hours. After completion of the reaction, 200 ml of water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.4 g of the desired compound.

Yield 80%. $n_D^{20}$ 1.5889.

EXAMPLE 33

N-Tert-butyl 4-[{-(4-methoxyphenoxy)-1,3-dimethylpyrazol-4-yl}methyleneaminomethyl]benzamide (compound No. 525)

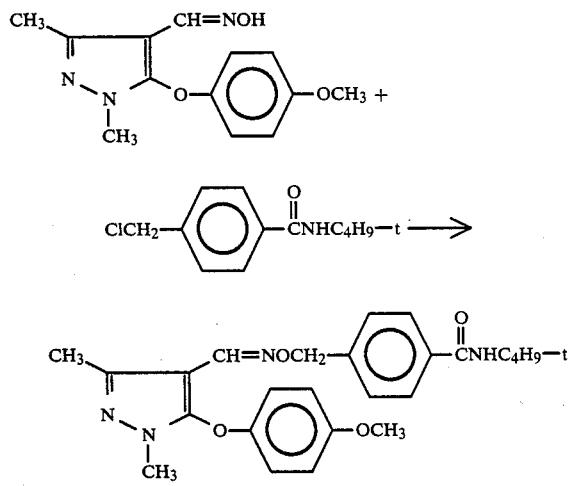

1.0 Gram (0.0038 mole) of 5-(4-methoxyphenoxy)-1,3-dimethylpyrazole-4-carbaldehyde oxime, 0.86 g (0.0038 mole) of N-tert-butyl-4-chloromethylbenzamide and 1.0 g (0.0072 mole) of potassium carbonate were added to 20 ml of acetonitrile, and the resulting mixture was heated under reflux for 6 hours. After completion of the reaction, acetonitrile was removed by evaporation under reduced pressure, after which water was added to the residue and extraction was carried out with ethyl acetate. The ethyl acetate extract was washed with water and dried, and ethyl acetate was removed by evaporation to obtain an oily product. This oily product was column-chromatographed on silica gel to obtain 1.4 g of the desired compound.

Yield 82%. $n_D^{20}$ 1.5662.

EXAMPLE 34

5-(4-Fluorophenoxy)-1,3-dimethyopyrazole-4-carbaldehyde oxime O-4-pivaloylbenzyl ether (compound No. 548)

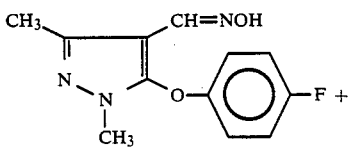

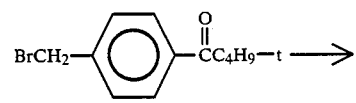

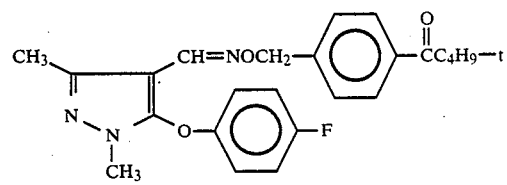

1.0 Gram (0.0040 mole) of 5-(4-fluoropheoxy)-1,3-dimethylpyrazole-4-carbaldehyde oxime, 1.0 g (0.0039 mole) of tert-butyl 4-bromomethylphenyl ketone and 1.0 g (0.0094 mole) of sodium carbonate were added to 40 ml of acetone, and the resulting mixture was heated to carry out reaction. After completion of the reaction, acetone was removed by evaporation under reduced pressure, after which water was added to the residue and extraction was carried out with ethyl acetate. The ethyl acetate extract was washed with water and dried, and ethyl acetate was removed by evaporation to obtain an oily product. This oily product was column-chromatographed on silica gel to obtain 1.5 g of the desired compound.

Yield 89%. $n_D^{20}$ 1.5567.

EXAMPLE 35

2-Methyl-2-[4-{(1,3-dimethyl-5-phenoxypyrazol-4-yl)methyleneaminoxymethyl}phenyl]-1,3-dioxolane (compound No. 562)

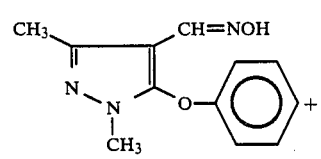

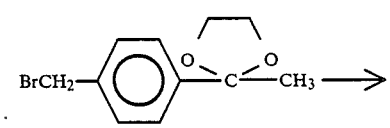

-continued

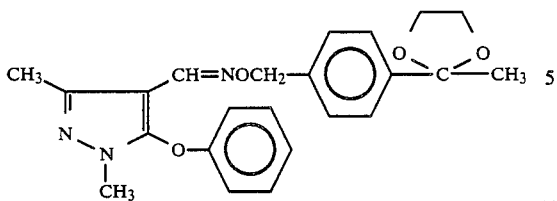

1.0 Gram (0.0043 mole) of 1,3-dimethyl-5-phenoxypyrazole-4-carbaldehyde oxime was dissolved in 20 ml of dioxane, and 0.14 g (0.0058 mole) of sodium hydride was added. Thereafter, 1.1 g (0.0043 mole) of 2-(4-bromomethylphenyl)-2-methyl-1,3-dioxolane was added to this solution which was then heated under reflux for 3 hours. After completion of the reaction, the reaction solution was poured into 200 ml of cold water and extracted with ethyl acetate. The ethyl acetate extract was washed with water and dried, and ethyl acetate was removed by evaporation to obtain an oily product. This oily product was column-chromatographed on silica gel to obtain 1.3 g of the desired compound.

Yield 74%. $n_D^{20}$ 1.5698.

EXAMPLE 36

2-[4-[{-(4-Fluorophenoxy)-1,3-dimethylpyrazol-4-yl}methyleneaminoxymethyl]phenyl]-2-methyl-1,3-dioxolane (compound No. 563)

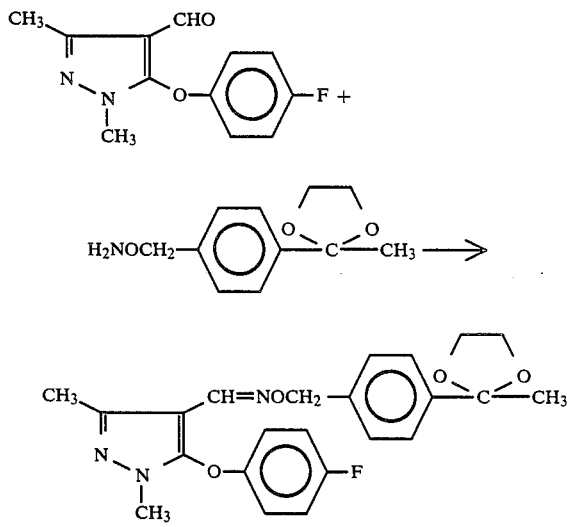

1.1 Gram (0.0043 mole) of 5-(4-fluorophenoxy)-1,3-dimethylpyrazol-4-carbaldehyde and 0.9 g (0.0043 mole) of 2-[4-(aminooxymethyl)phenyl]-2-methyl-1,3-dioxolane were added to 20 ml of ethanol, and the resulting mixture was heated for 3 hours to carry out reaction. After completion of the reaction, ethanol was removed by evaporation under reduced pressure, after which water was added to the residue and extraction was carried out with ethyl acetate. The ethyl acetate extract was washed with water and dried, and ethyl acetate was removed by evaporation to obtain an oily product. This oily product was column-chromatographed on silca gel to obtain 1.3 g of the desired compound.

Yield 72%. $n_D^{20}$ 1.5555.

EXAMPLE 37

1,3-Dimethyl-5-phenoxypyrazole-4-carbaldehyde oxime O-4-(1-hydroxyethyl)benzyl ether (compound No. 584)

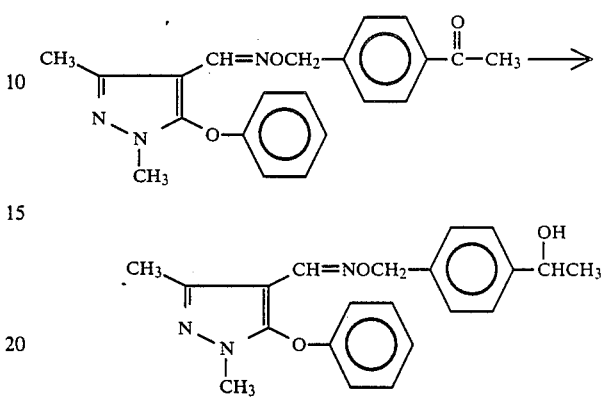

1.0 Gram (0.0028 mole) of 1,3-dimethyl-5-phenoxypyrazole-4-carbaldehyde oxime-0-4-acetylbenzyl ether, 1.0 g (0.0026 mole) of sodium borohydride and 1 g (0.025 mole) of sodium hydroxide were added to 100 ml of methanol, and the resulting mixture was heated under reflux for 3 hours. After completion of the reaction, methanol was removed by evaporation under reduced pressure, after which water added to the residue and extraction was carried out with ethyl acetate. The ethyl acetate extract was washed with water and dried, and ethyl acetate was removed by evaporation to obtain an oily product. This oily product was column-chromatographed on silica gel to obtain 0.8 g of the desired compound.

Yield 78%. $n_D^{20}$ 1.5748.

EXAMPLE 38

N-4-[(1,3-dimethyl-5-phenoxypyrazol-4-yl)methyleneaminooxymethyl]phenylfomamide (compound No. 589)

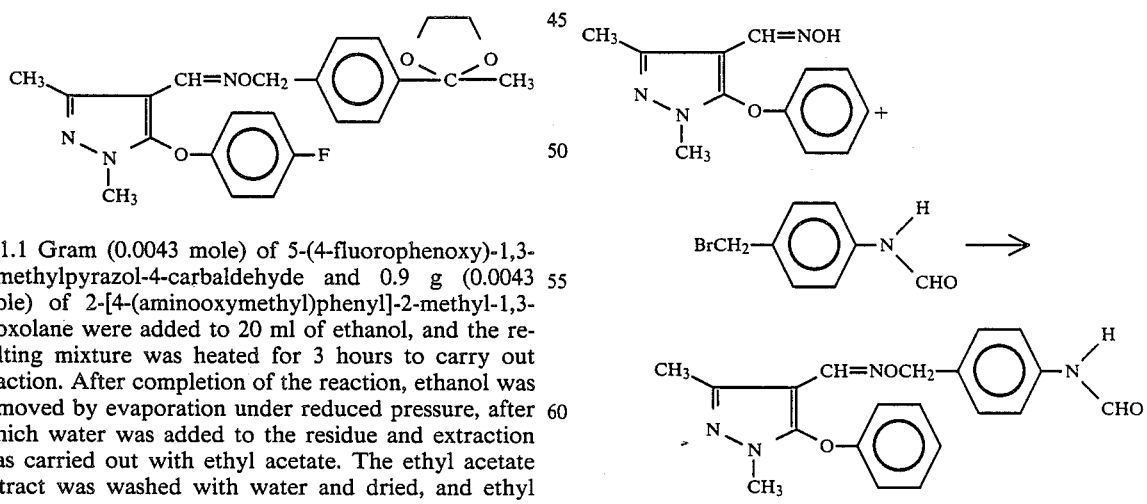

1.0 Gram (0.0043 mole) of 1,3-dimethyl-5-phenoxypyrazole-4-carbaldehyde oxime was dissolved in 20 ml of dimethyl sulfoxide, and after adding 0.3 g (0.0053 mole) of powdery potassium hydroxide, the resulting solution was stirred. To this reaction solution was added 0.92 g (0.0043 mole) of N-(4-bromomethyphenyl)formamide, and reaction was carried out at room temperature for 3 hours. After completion of the reaction, the reaction solution was poured into 200 ml of water and extracted with ethyl acetate. The ethyl acetate extract was washed with water and dried, and ethyl acetate was removed by evaporation to obtain an oily product. This oily product was column-chromatographed on silica gel to obtain 1.2 g of the desired compound.

Yield 76%. m.p. 105.3° C.

EXAMPLE 39

Isopropyl N-4-[{5-(4-fluorophenoxy)-1,3-dimenthylpyrazol-4-yl}methyleneaminooxymethyl]phenylcarbamate (compound No. 595)

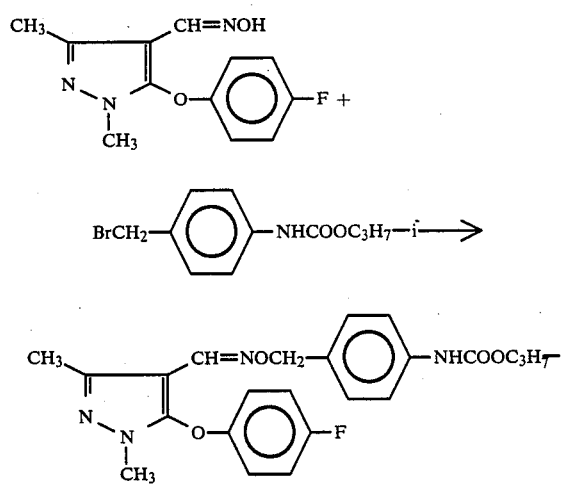

1.0 Gram (0.0040 mole) of 5-(4-fluorophenoxy)-1,3-dimethylpyrazole-4-carbaldehyde oxime, 1.1 g (0.0040 mole) of isopropyl N-4-bromomethylphenylcarbamate and 1.0 g (0.0072 mole) of potassium carbonate were added to 20 ml of acetonitrile, and the resulting mixture was heated under reflux for 6 hours. After completion of the reaction, acetonitrile was removed by evaporation under reduced pressure, after which water was added and extraction was carried out with ethyl acetate. The ethyl acetate extract was washed with water and dried, and ethyl acetate was removed by evaporation to obtain an oily product. This oily product was column-chromatographed on silica gel to obtain 1.5 g of the desired compound.

Yield 85%. $n_D^{20}$ 1.5645.

EXAMPLE 40

Isobutyl N-4-[{5-(4-methoxyphenoxy)-1,3-dimethylpyrazol-4-yl}methyleneaminooxymethyl]phenylcarbamate (compound No. 617)

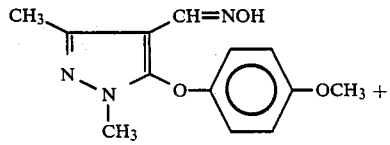

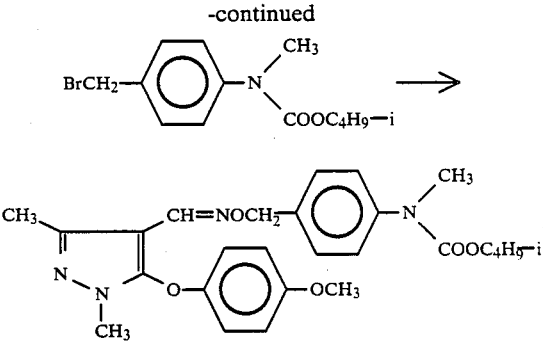

1.0 Gram (0.0038 mole) of 5-(4-methoxyphenoxy)-1,3-dimethylpyrazole-4-carbaldehyde oxime, 1.1 g (0.0038 mole) of isobutyl N-4-bromomethylphenyl-N-methylcarbamate and 1.0 g (0.0094 mole) of sodium carbonate were added to 40 ml of acetone, and the resulting mixture was heated to carry out reaction. After completion of the reaction, acetone was removed by evaporation under reduced pressure, after which water was added and extraction was carried out with ethyl acetate. The ethyl acetate extract was washed with water and dried, and ethyl acetate was removed by evaporation to obtain an oily product. This oily product was column-chromatographed on silica gel to obtain 1.5 g of the described compound.

Yield 83%. $n_D^{20}$ 1.5538.

EXAMPLE 41

N-4-[(1,3-dimethyl-5-phenoxypyrazol-4yl) methyleneaminooxymethyl]phenyl-N-isopropylformamide (compound No. 636)

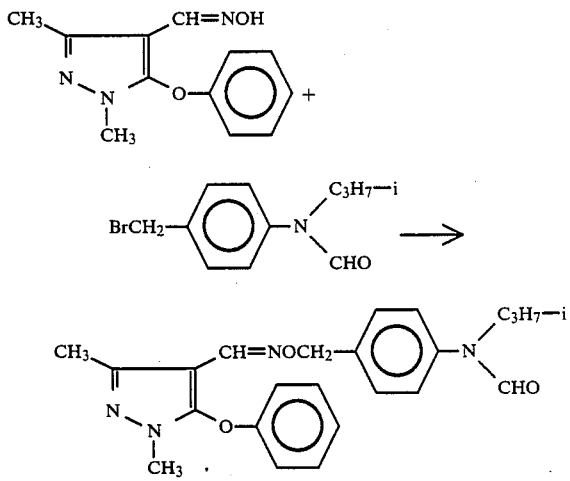

1.0 Gram (0.0043 mole) of 1,3-dimethyl-5-phenoxypyrazole-4-carbaldehyde oxime was dissolved in 20 ml of dioxane, and 0.1 g (0.0043 mole) of sodium hydride was added to synthesize the sodium salt of said oxime. To this reaction solution was added 1.1 g (0.0043 mole) of N-4-bromomethylphenyl-N-isopropylformamide, and reaction was carried out at from 40° to 50° C. for 3 hours. After completion of the reaction, the reaction solution was poured into 200 ml of water and extracted with ethyl acetate. The ethyl acetate extract was washed with water and dried, and ethyl acetate was removed by evaporation to obtain an oily product. This

EXAMPLE 42

N-4-[(1,3-dimethyl-5-phenoxypyrazol-4-yl)methyleneaminooxymethyl]phenyl-N-ethylpivalamide (compound No. 647)

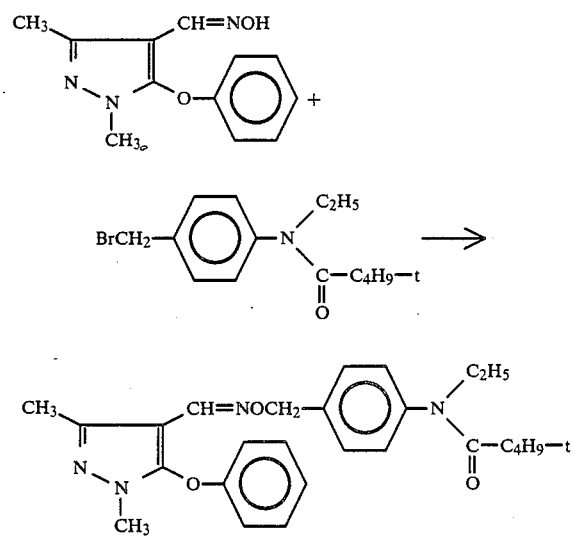

1.0 Gram (0.0043 mole) of 1,3-dimethyl-5-phenoxypyrazole-4-carbaldehyde oxime, 1.3 g (0.0043 mole) of N-4-bromomethylphenyl-N-ethylpivalamide and 0.2 g (0.005 mole) of potassium hydroxide were dissolved in 30 ml of dimethyl sulfoxide, and reaction was carried out at from 40° to 50° C. for 6 hours. After completion of the reaction, the reaction solution was poured into 200 ml of water and extracted with ethyl acetate. The ethyl acetate extract was washed with water and dried, and ethyl acetate was removed by evaporation to obtain an oily product. This oily product was column-chromatographed on silica gel to obtain 1.5 g of the desired compound.

Yield 78%. Form of product: paste.

EXAMPLE 43

5-Ethyl-3-[N-4[{5-(4-fluorophenoxy)-1,3-dimethylpyrazol-4-yl}methyleneaminooxymethyl]-phenyl]-2-oxazolidone (compound No. 657)

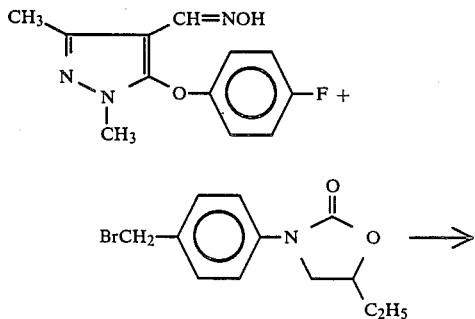

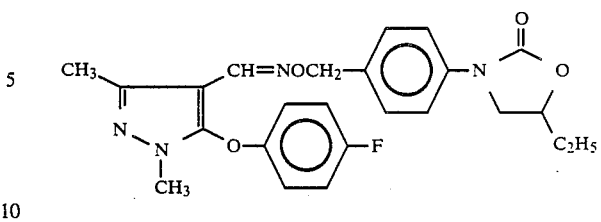

1.0 Gram (0.0040 mole) of 5-(4-fluorophenoxy)-1,3-dimethylpyrazole-4-carbaldehyde oxime and 1.1 g (0.0040 mole) of 3-(4-bromomethylphenyl)-5-ethyl-2-oxazolidone were dissolved in 20 ml of dimethyl sulfoxide, and 0.3 g (0.0053 mole) of powdery potassium hydroxide was added. Reaction was then carried out at from 40° to 50° C. for 5 hours. After completion of the reaction, the reaction solution was poured into 200 ml of water and extracted with ethyl acetate. The ethyl acetate extract was washed with water and dried, and ethyl acetate was removed by evaporation to obtain an oily product. This oily product was column-chromatographed on silica gel to obtain 1.3 g of the desired compound.

Yield 72%. $n_D^{20}$ 1.5601.

EXAMPLE 44

1,3-Dimethyl-5-phenozypyrazole-4-carbaldehyde oxime O-2-phenoxyethyl ether (compound No. 658)

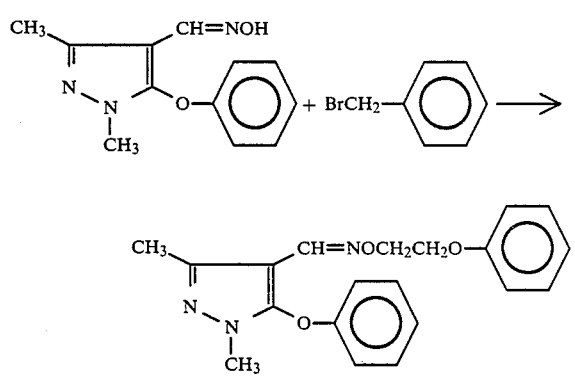

1.0 Gram (0.0043 mole) of 1,3-dimethyl-5-phenoxypyrazole-4-carbaldehyde oxime was dissolved in 20 ml of dimethyl sulfoxide, and after adding 0.3 g (0.0053 mole) of powdery potassium hydroxide, the resulting solution was stirred. To this solution was added 0.86 g (0.0043 mole) of 2-bromoethoxybenzene, and reaction was carried out at room temperature for 3 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.3 g of the desired compound.

Yield 86%. $n_D^{20}$ 1.5657.

EXAMPLE 45

1,3-Dimethyl-5-(3-trifluoromethyphenoxy)pyrazole-4-carbaldehyde oxime O-2-(4-tert-butylphenoxy)ethyl ether (compound No. 671)

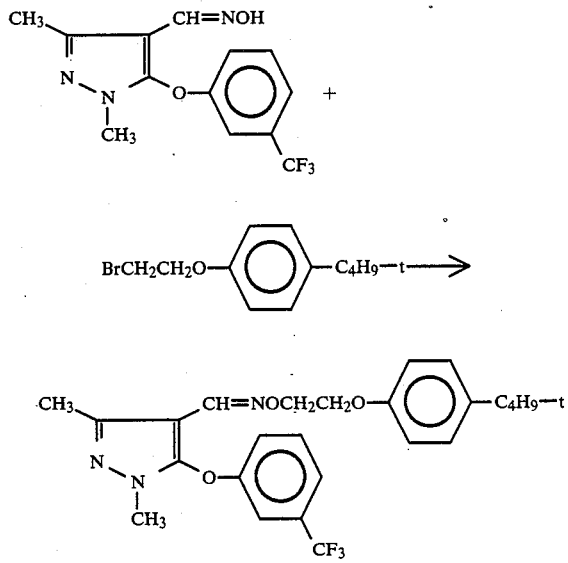

1.0 Gram (0.0030 mole) of 1,3-dimethyl-5-(3-trifluoromethylphenoxy)pyrazole-4-carbaldehyde oxime, 0.86 g (0.0034 mole) of p-(2-bromoethoxy)-tert-butylbenzene and 1.38 g of potassium carbonate were added to 50 ml of acetonitrile, and the resulting mixture was heated under reflux for 8 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.4 g of the desired compound.

Yield 89%. $n_D^{20}$ 1.5287.

EXAMPLE 46

Ethyl 4-[2-{(1,3-dimethyl-5-phenoxypyrazol-4-yl)methyleneaminooxy}ethoxy]benzoate (compound No. 706)

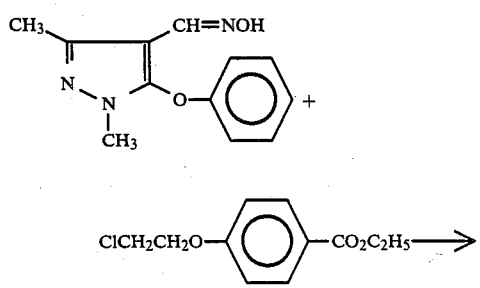

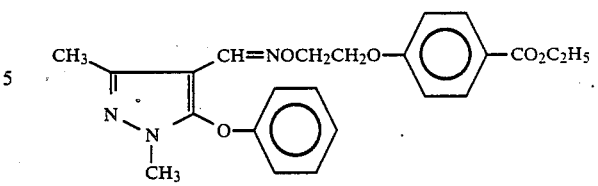

1.0 Gram (0.0043 mole) of 1,3-dimethyl-5-phenoxypyrazole-4-carbaldehyde oxume and 0.3 g (0.0075 mole) of powdery sodium hydroxyde were added to 30 ml of dimethylformamide, and the resulting mixture was stirred. To this solution was added 0.99 g (0.0043 mole) of ethyl p-(2-chloroethoxy)benzoate, and reaction was carried out at from 30° to 40° C. for 3 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.3 g of the desired compound.

Yield 72%. $n_D^{20}$ 1.5577.

EXAMPLE 47

5-(4-Chlorophenoxy)-1,3-dimethylpyrazole-4-carbaldehyde oxime O-2-(3,4-dichlorophenoxy)ethyl ether (compound No. 723)

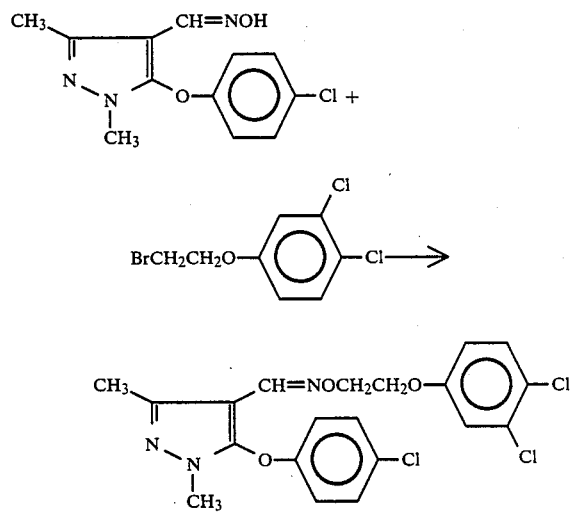

1.0 Gram (0.0038 mole) of 5-(4-chlorophenoxy)-1,3-dimethylpyrazole-4-carbaldehyde oxime, 1.0 g (0.0038 mole) of 2-bromoethoxy-3,4-dichlorobenzene and 0.58 g (0.0038 mole) of 1,8-diazabicyclo[5.4.0]-7-undecene were dissolved in 50 ml of dioxane, and rection was carried out at from 60° to 80° C. for 5 hours with stirring. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.5 g of the desired compound.

Yield 87%. $n_D^{20}$ 1.5756.

EXAMPLE 48

5-(4-Fluorophenoxy)-1,3-dimethylpyazole-4-carbaldehyde oxime O-2-phenoxypropyl ether (compound No. 741)

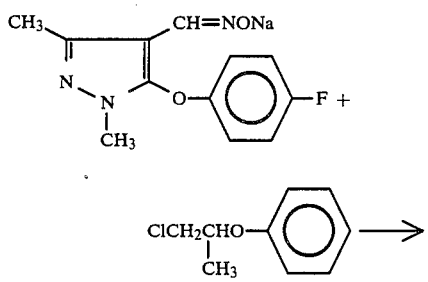

1.0 Gram (0.0037 mole) of sodium 5-(4-chlorophenoxy)-1,3-dimethylpyrazole-4-carbaldehyde oxime and 0.63 g (0.037 mole) of 2-chloro-1-methylethoxybenzene were added to 50 ml of tetrahydrofuran, and the resulting mixture was heated under reflux for 5 hours with stirring. After completion of the reaction, water was added to the reaction solution which was then extracted with ethyl acetate. The ethyl acetate was washed with water and dried, and ethyl acetate was removed by evaporation to obtain an oily product. This oily product was column-chromatographed on silica gel to obtain 1.3 g of the desired compound.

Yield 87%. $n_D^{20}$ 1.5484.

EXAMPLE 49

1,3-Dimethyl-5-phenoxypyrazole-4-carbaldehyde oxime O-2-(4-tert-butylphenylthio)ethyl ether (compound No. 753)

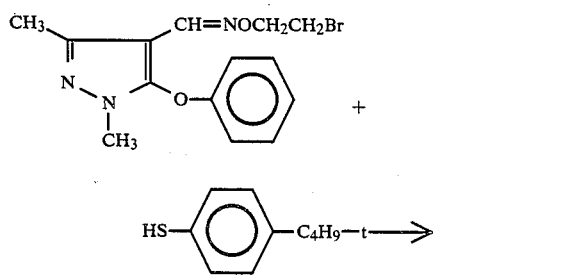

1.0 Gram (0.0030 mole) of 1,3-dimethyl-5-phenoxypyrazole-4-carbaldehyde oxime O-2-bromoethyl ether, 0.5 g (0.0030 mole) of p-tert-butylbenzenethiol and 1.0 g (0.0072 mole) of potassium carbonate were added to 60 ml of acetonitrile, and the resulting mixture was heated under reflux for 5 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.1 g of the desired compound.

Yield 87%. $n_D^{20}$ 1.5775.

EXAMPLE 50

1,3-Dimethyl-5-phenoxypyrazole-4-carbaldehyde oxime O-3-(4-chlorophenoxy)propyl ether (compound No. 761)

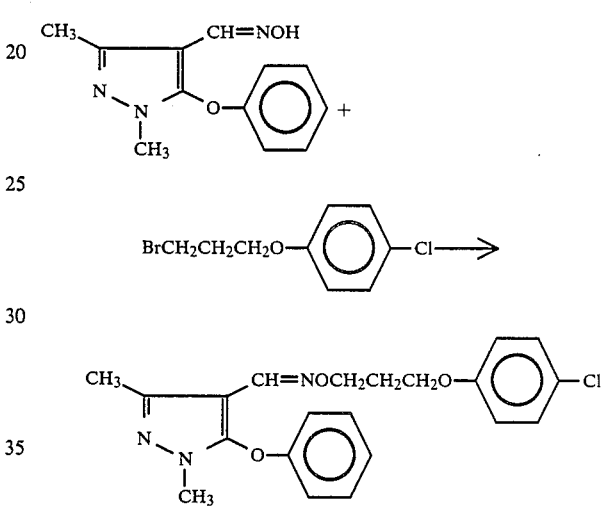

1.0 Gram (0.0043 mole) of 1,3-dimethyl-5-phenoxypyrazole-4-carbaldehyde oxime and 0.3 g (0.0053 mole) of potassium hydroxide were added to 20 ml of dimethyl sulfoxide, and the resulting mixture was stirred for 1 hour. To this solution was added 1.07 g (0.0043 mole) of p-chloro-3-bromopropoxybenzene, and reaction was carried out at from 40° to 50° C. for 4 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.3 g of the desired compound.

Yield 76%. $n_D^{20}$ 1.5746.

EXAMPLE 51

1,3-Dimethyl-5-phenoxypyrazole-4-carbaldehyde oxime O-4-(4-chlorophenoxy)-2-butenyl ether (compound No. 776)

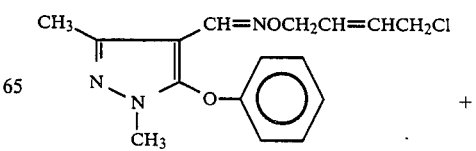

-continued

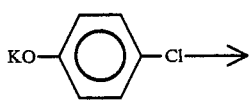

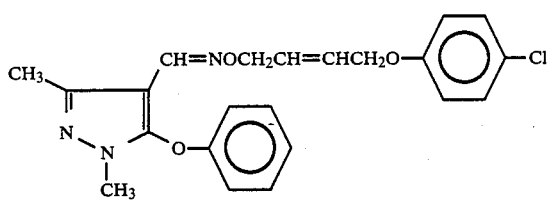

1.0 Gram (0.0031 mole) of 1,3-dimethyl-5-phenoxypyrazole-4-carbaldehyde oxime O-4-chloro-2-butenyl ether and 0.6 g (0.0036 mole) of the potassium salt of p-chlorophenol were added to 50 ml of tetrahydrofuran, and the resulting mixture was heated under reflux for 3 hours with stirring. After completion of the reaction, water was added to the reaction solution which was then extracted with ethyl acetate. The ethyl acetate extract was washed with water and dried, and ethyl acetate was removed by evaporation to obtain on oily product. This oily product was column-chromatographed on silica gel to obtain 1.2 g of the desired compound.

Yield 93%. $n_D^{20}$ 1.5712.

EXAMPLE 52

1,3-Dimethyl-5-phenoxypyrazole-4-carbaldehyde oxime O-6-phenoxyphenyl ether (compound No. 780)

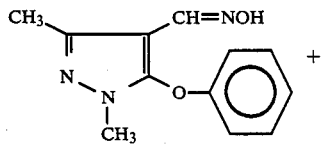

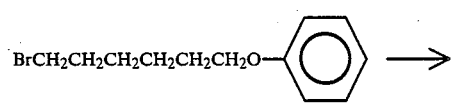

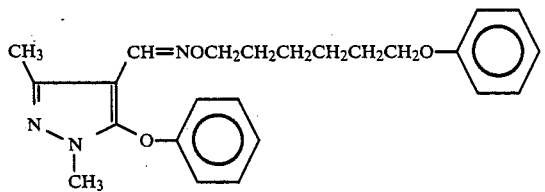

1.0 Gram (0.0043 mole) of 1,3-dimethyl-5-phenoxypyrazole-4-carbaldehyde oxime was dissolved in 10 ml of dimethyl sulfoxide, and after adding 0.11 g (0.0045 mole) of sodium hydride at room temperature, the resulting solution was stirred for 30 minutes. To this solution was added 1.1 g (0.0043 mole) of 6-bromohexyloxybenzene, and reaction was carried out at from 50° to 60° C. for 3 hours. After completion of the reaction, water was added to the reaction solution which was then extracted with acetate. The ethyl acetate was washed with water and dried, and ethyl acetate was removed by evaporation to obtain an oily product. This oily product was column-chromatographed on silica gel to obtain 1.4 g of the desired compound.

Yield 80%. $n_D^{20}$ 1.5583.

EXAMPLE 53

2-[(1,3-Dimethyl-5-phenoxypyrazol-4-yl)methyleneaminooxy]ethyl benzoate (compound No. 787)

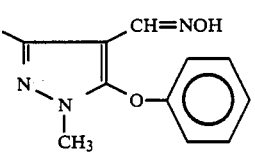

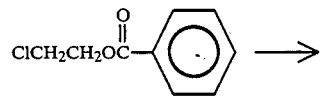

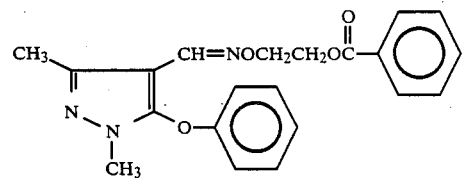

1.0 Gram (0.0043 mole) of 1,3-dimethyl-5-phenoxypyrazole-4-carbaldehyde oxime and 0.3 g (0.0054 mole) of powdery potassium hydroxide were added to 20 ml of dimethyl sulfoxide, and the resulting mixture was stirred for 30 minutes. To this solution was added 0.8 g (0.0043 mole) of 2-chloroethyl benzoate, and reaction was carried out at from 40° to 50° C. for 3 hours. After completion of the reaction, water was added to the reaction solution which was then extracted with ethyl acetate. The ethyl acetate was washed with water and dried, and ethyl acetate was removed by evaporation to obtain an oily product. This oily product was column-chromatographed on silica gel to obtain 1.3 g of the desired compound.

Yield 86%. $n_D^{20}$ 1.5632.

EXAMPLE 54

1,3-Dimethyl-5-phenoxypyrazole-4-carbaldehyde oxime O-2-ethoxyethyl ether (compound No. 789)

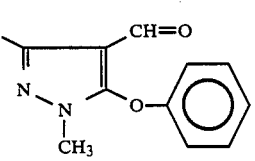

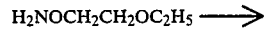

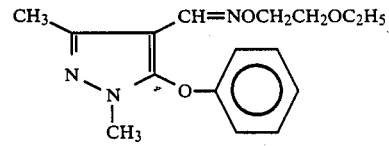

1.0 Gram (0.0046 mole) of 1,3-dimethyl-5-phenoxypyrazole-4-carbaldehyde was dissolved in 40 ml of ethanol, and 0.48 g (0.0046 mole) of O-(2-ethoxyethyl)hydroxylamine was added with stirring. Reaction was then carried out at room temperature for 3 hours. After completion of the reaction, water was added to the reaction solution which was then extracted with ethyl acetate. The ethyl acetate extract was washed with water and dried, and ethyl acetate was removed by evaporation to obtain an oily product. This oily product was column-chromatographed on silica gel to obtain 1.2 g of the desired compound.

Yield 86%. $n_D^{20}$ 1.5407.

EXAMPLE 55

1,3-Dimethyl-5-phenoxypyrazole-4-carbaldehyde oxime O-methyl ether (compound No. 790)

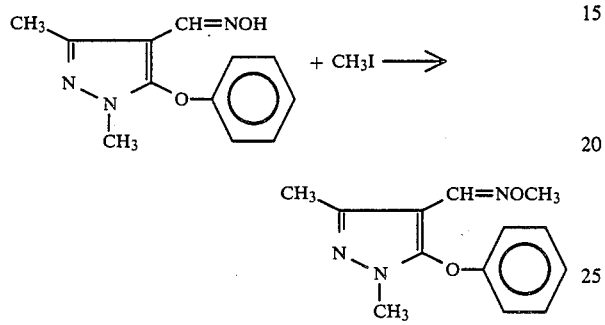

1.0 Gram (0.0043 mole) of 1,3-dimethyl-5-phenoxypyrazole-4-carbaldehyde oxime was dissolved in 20 ml of dimethyl sulfoxide, and after adding 0.3 g (0.0053 mole) of powdery potassium hydroxide, the resulting mixture was stirred. To this reaction was added 1.0 g (0.0063 mole) of methyl iodide, and reaction was carried out at room temperature for 3 hours. After completion of the reaction, the reaction solution was poured into 200 ml of water and extracted with ethyl acetate. The ethyl acetate extract was washed with water and dried, and ethyl acetate was removed by evaporation under reduced pressure to obtain an oily product. This oily product was column-chromatographed on silica gel to obtain 0.3 g of the desired compound.

Yield 76%. m.p. 70.2° C.

EXAMPLE 56

5-(4-Chlorophenoxy)-1,3-dimethylpyrazole-4-carbaldehyde oxime O-2-propynyl ether (compound No. 795)

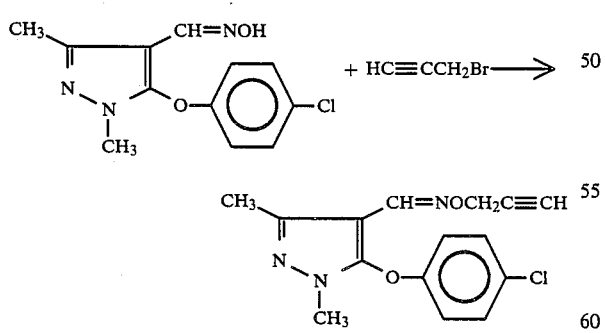

1.0 Gram (0.0033 mole) of 5-(4-chlorophenoxy)-1,3-dimethylpyrazole-4-carbaldehyde oxime, 0.5 g (0.0042 mole) of propargyl bromide and 1.0 g (0.0072 mole) of potassium carbonate were added to 50 ml of acetone, and the resulting mixture was heated under reflux. After completion of the reaction, the reaction solution was poured into 200 ml of water and extracted with ethyl acetate. The ethyl acetate extract was washed with water and dried, and ethyl acetate was removed by evaporation under reduced pressure to obtain an oily product. This oily product was column-chromatographed on silica gel to obtain 0.9 g of the desired compound.

Yield 87%. $n_D^{20}$ 1.5670.

EXAMPLE 57

5-(4-Methoxyphenoxy)-1,3-dimethylpyrazole-4-carbaldehyde oxime O-2-(4-fluorophenyl)ethyl ether (compound No. 815)

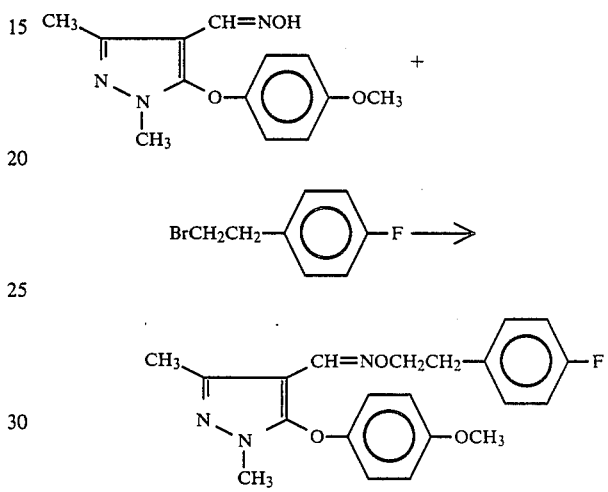

1.0 Gram (0.0038 mole) of 5-(4-methoxyphenoxy)-1,3-dimethylpyrazole-4-carbaldehyde oxime was dissolved in 20 ml of dioxane, and after adding 0.1 g (0.0042 mole) of sodium hydride, the resulting mixture was stirred. To this reaction solution was added 0.78 g (0.0038 mole) of 2-(4-fluorophenyl)ethyl bromide, and reaction was carried out at from 40° to 50° C. for 3 hours. After completion of the reaction, the reaction solution was poured into 200 ml of water and extracted with ethyl acetate. The ethyl acetate extract was washed with water and dried, and ethyl acetate was removed by evaporation under reduced pressure to obtain an oily product. This oily product was column-chromatograhed on silica gel to obtain 1.2 g of the desired compound.

Yield 82%. $n_D^{20}$ 1.5588.

EXAMPLE 58

5-(4-Chlorophenoxy)-1,3-dimethylpyrazole-4-carbaldehyde oxime O-3-(4-chlorophenyl)propyl ether (compound No. 824)

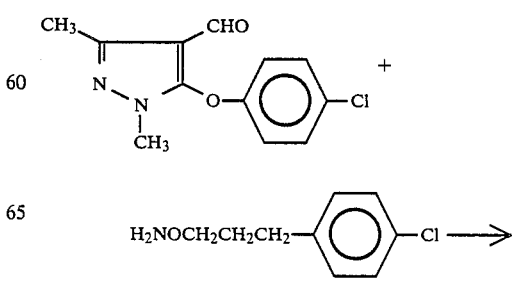

-continued

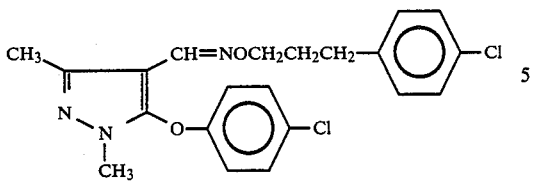

1.0 Gram (0.004 mole) of 5-(4-chlorophenoxy)-1,3-dimethylpyrazole-4-carbaldehyde was dissolved in 30 ml of methanol, and 0.74 g (0.004 mole) of O-[3-(4-chlorophenyl)propyl]hydroxylamine was added at room temperature with stirring. Reaction was then carried out at from 40° to 50° C. for 2 hours. Methanol was then removed by evaporation under reduced pressure, after which water was added to the residue and extraction was carried out with ethyl acetate. The ethyl acetate extract was washed with water and dried, and ethyl acetate was removed by evaporation under reduced pressure to obtain an oily product. This oily product was column-chromatographed on silica gel to obtain 1.1 g of the desired compound.

Yield 66%. $n_D^{20}$ 1.5751.

EXAMPLE 59

5-(4-Chlorophenoxy)-1-methyl-3-phenylpyrazole-4-carbaldehyde oxime O-4-chlorocinnamyl ether (compound No. 846)

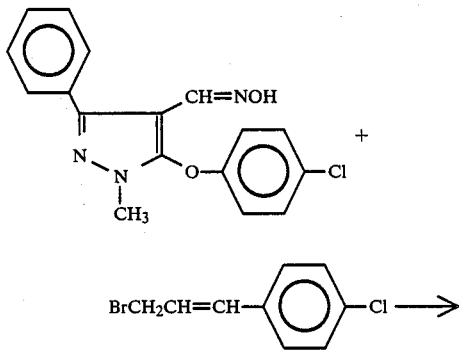

1.0 Gram (0.0030 mole) of 5-(4-chlorophenoxy)-1-methyl-3-phenylpyrazole-4-carbaldehyde oxime was reacted with 0.7 g (0.0030 mole) of p-chlorocinnamyl bromide and 0.2 g (0.005 mole) of sodium hydroxide at 30° C. for 6 hours in 30 ml of dimethyl sulfoxide. After completion of the reaction, the reaction solution was poured into 200 ml of water and extracted with ethyl acetate. The ethyl acetate extract was washed with water and dried, and ethyl acetate was removed by evaporation under reduced pressure to obtain an oily product. This oily product was column-chromato-graphed on silica gel to obtain 1.1 g of the desired compound.

Yield 76%. $n_D^{20}$ 1.5980.

EXAMPLE 60

1,3-Dimethyl-5-phenoxypyrazol-4-yl phenyl ketone oxime O-allyl ether (compound No. 857)

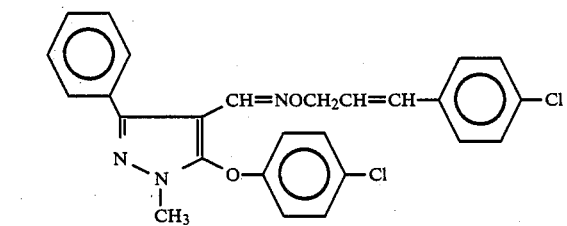

1.0 Gram (0.0033 mole) of 1,3-dimethyl-5-phenoxypyrazol-4-yl phenyl ketone oxime, 0.5 g (0.0041 mole) of allyl bromide and 1.0 g of potassium carbonate were added to 50 ml of acetone, and the resulting mixture was heated for 6 hours to carry out reaction. After completion of the reaction, the reaction solution was poured into 200 ml of water and extracted with ethyl acetate. The ethyl acetate extract was washed with water and dried, and ethyl acetate was removed by evaporation under reduced pressure to obtain an oily product. This oily product was column-chromatographed on silica gel to obtain 0.9 g of the desired compound.

Yield 79%. $n_D^{20}$ 1.5800.

Synthesis of Starting Materials

Synthetic Example 1

13.2 Grams (0.006 mole) of tert-butyl 4-methylbenzoate, 0.3 g (0.0012 mole) of benzoyl peroxide and 6 g (0.006 mole) of sodium carbonate were suspended in 100 ml of carbon tetrachloride, and 9.6 g (0.06 mole) of bromine was added dropwise at 50° C. over 30 minutes with stirring. After completion of the addition, reaction was continued for further 30 minutes. The reaction solution was then cooled and filtered to remove carbon tetrachloride-insoluble matters. Carbon tetrachloride was then removed by evaporation under reduced pressure to obtain 16.2 g of tert-butyl 4-bromomethylbenzoate as crystals.

Yield 90%. m.p. 53.4° C.

Synthetic Example 2

$$BrCH_2-\text{C}_6\text{H}_4-COOC_4H_9\text{-}t + \text{N-hydroxyphthalimide} \longrightarrow H_2NOCH_2-\text{C}_6\text{H}_4-COOC_4H_9\text{-}t$$

15.0 Grams (0.049 mole) of tert-butyl 4-bromomethylbenzoate, 8.2 g (0.05 mole) of N-hydroxyphthalimide and 3.0 (0.054 mole) of potassium hydroxide were added to 200 ml of dimethylformamide, and the resulting mixture was stirred at room temperature for 30 minutes and then an 50° C. for 30 minutes. The reaction solution was cooled with ice water and filtered to obtain crystals. The crystals were dissolved in 50 ml of methylene chloride, and to this solution was slowly added dropwise 3 ml of isopropanol containing 0.5 g (0.05 mole) of hydrazine hydrate at room temperature. After completion of the addition, the reaction solution was heated under reflux for 2 hours. The reaction solution was cooled and filtered, and the filtrate was concentrated to obtain 11.0 g of tert-butyl 4-(aminoxymethyl)-benzoate.

Yield 90%. $n_D^{15.6}$ 1.5296.

Synthetic Example 3

$$CH_3-\text{C}_6\text{H}_4-\text{C}_3H_4(CN) \xrightarrow{Br_2} BrCH_2-\text{C}_6\text{H}_4-\text{C}_3H_4(CN)$$

3.0 Grams (0.02 mole) of 1-p-tolylcyclopropane-1-carbonitrile and 0.1 g (0.0004 mole) of benzoyl peroxide were dissolved in 50 ml of carbon tetrachloride, and 3.2 g of bromine was added dropwise over 30 minutes under reflux. After completion of the addition, reaction was continued for further 30 minutes. After cooling the reaction solution, carbon tetrachloride was removed by evaporation to obtain 4.4 g of 1-(4-bromomethylphenyl)cyclopropane-1-carbonitrile.

Yield 90%. Form of product: paste.

NMR: δ (ppm) 1.15–1.40 (2H, m), 2.50–2.75 (2H, m), 4.45 (1H, s), 7.35 (4H, s).

Synthetic Example 4

[1,3-dimethyl-5-phenoxypyrazole-4-carbaldehyde oxime] $\xrightarrow{BrCH_2CH_2Br}$ [1,3-dimethyl-5-phenoxypyrazol-4-carbaldehyde oxime O-2-bromoethyl ether]

5.0 Grams (0.00216 mole) of 1,3-dimethyl-5-phenoxypyrazole-4-carbaldehyde oxime and 41.0 g (0.218 mole) of 1,2-dibromethane were dissolved in 100 ml of dimethyl sulfoxide, and after adding 14.4 g (0.219 mole) of 85% powdery potassium hydroxide with ice-cooling, the resulting solution was stirred for 30 minutes. After completion of the reaction, the reaction solution was poured into 300 ml of water, extracted with three 80-ml portions of ether and washed with 300 ml of water. The ether extract was dried over anydrous sodium sulfate, and ether was removed by evaporation. The residue was dry column-chromatographed on silica gel to obtain 5.2 g of 1,3-dimethyl-5-phenoxypyrazol-4-carbaldehyde oxime O-2-bromoethyl ether.

Yield 71.2%. $n_D^{23.8}$ 1.5721.

The present invention provides a technique for exterminating or controlling injurious insects and mites using the physiological activity of the compounds of the present invention. In one of the embodiments of the invention, the compounds are directly applied as such to the objects to be protected or to the pests to be controlled (undiluted spray). For instance, the compounds of the present invention in the form of a liquid of 95% or higher purity can be sprayed from aeroplanes to form a fog of extremely fine liquid particles.

The compounds of the present invention can also be used to treat ponds and pools in which the larvae of the insects or treat environmental water or irrigative water grown with hosts for the larvae to render the living environment or feet (hosts) toxic to the larvae.

As is customary in the art, however, in order to exterminate or control injurious insects and mites using the physiological activity of the compounds of the present invention, the compounds are applied in most cases in a form suitable for use, for example, as supported on or diluted with inert carriers and if necessary, mixed with auxiliary agents.

General suggestions regarding the formulation of insecticidal compositions with the compounds of the present invention will be described below.

The compounds of the present invention are mixed with a suitable proportion of suitable inert carriers together with auxiliary agents if necessary to allow the compounds to dissolve, disperse, suspend, mix, impregnate, adsorb or adhere, and thus they are formed into suitable preparations such as for example solutions, suspensions, emulsifiable concentrates, oil sprays, wettable powders, dusts, granules, tablets, pellets, pastes, aerosols, etc.

The inert carriers used in the formulation may be either solid or liquid. As examples of the solid carriers, there may be mentioned vegetable powders such as soybean flour, cereal flour, wood flour, bark flour, saw dust, powdered tobacco stalk, powdered walnut shell, bran, powdered cellulose, and extraction residues of vegetables; fibrous materials such as paper, corrugated paperboard, and waste cloth; synthetic polymers such as powdered synthetic resins; inorganic or mineral products such as clays (e.g. Kaolin, bentonite, and acid clay), talcs (e.g. talc and pyrophylite), siliceous substances [e.g. diatomaceous earth, silica sand, mica, and "white carbon" (highly dispersed synthetic silicon dioxide, also called finely divided hydrated silica or hydrated silicon dioxide, some commercial products containing calcium silicate as major constituent)], activated carbon, powdered sulfur, pumice, calcined diatomaceous earth, ground brick, fly ash, sand, calcium carbonate, and calcium phosphate; chemical fertilizers such as ammonium sulfate, ammonium nitrate, urea, and ammonium chloride; and farmyard manure. These materials are used alone or in combination. Materials usable as liquid carriers are selected from those which will dissolve the active ingredients and those which do not dissolve them, but can disperse them with the aid of adjuvants. For example, the following materials can be used alone or in combination: Water, alcohols (e.g. methanol, ethanol, isopropanol, butanol, ethylene glycol), ketones (e.g. acetone, methyl ethyl ketone, methyl isobutyl ketone, diisobutyl ketone and cyclohexanone), ethers (e.g. ethyl ether, dioxane, cellosolves, dipropyl ether and tetrahydrofuran), aliphatic hydrocarbons (e.g. gasoline and mineral oils), aromatic hydrocarbons (e.g. benzene, toluene, xylene, solvent naphtha and alkylnapththalenes), halohydrocarbons (e.g. dichloroethane, chlorinated benzenes, chloroform and carbon tetrachloride), esters (e.g. ethyl acetate, dibutyl phthalate, diisopropyl phthalate and dioctyl phthalate), acid amides (e.g. dimethylformamide, diethylformamide and dimethylacetamide), nitriles (e.g. acetonitrile), and dimethyl sulfoxide.

Gaseous carriers include freons and other aerosol propellants which are a gas under normal conditions.

The adjuvants, which are mentioned below, are used according to individual purposes. In some cases, they are used in combination with one another. In some other cases, no adjuvant is used at all.

For the purpose of emulsification, dispersion, solubilization and/or wetting of the active ingredients, there are used surface active agents such as for example polyoxyethylene alkylaryl ethers, polyoxyethylene alkyl ethers, polyoxyethylene higher fatty acid esters, polyoxyethylene resinates, polyoxyethylene sorbitan monolaurate, polyoxyethylene sorbitan monooleate, alkylarylsulfonates, naphthalenesulfonic acid condensation products, ligninsulfonates and higher alcohol sulfate esters.

For the purpose of stabilizing the dispersion, tackification and/or agglomeration of the active ingredients, there may be used for example casein, gelatin, starch, alginic acid, methylcellulose, carboxymethylcellulose, gum arabic, polyvinyl alcohol, turpentine oil, rice bran oil, bentonite and ligninsulfonates.

For the purpose of improving the flow property of the solid compositions, it is recommendable to use waxes, stearates or alkyl phosphates.

As peptizers for dispersible compositions, it is also recommendable to use naphthalenesulfonic acid condensation products and polyphosphates.

It is also possible to add a defoamer such as for example a silicone oil.

The content of the active ingredient may be adjusted as occasion demands. For the preparation of powdered or granulated products, the content is usually from 0.5 to 20% by weight, and for the preparation of emulsifiable concentrates, suspension concentrates or wettable powders, it is preferably from 0.1 to 50% by weight.

For controlling various insects, mites and fungi, inhibiting their growth and protecting useful plants from damage caused by these insects, mites and fungi, the compositions of the present invention for use in agriculture and horticulture are applied in insecticidally, acaricidally or fungicidally effective amounts. In applying the present compositions, they are applied, as such or after properly diluted with or suspended in water or other suitable medium, to soil or the foliage of crops to be protected from the attack of insects, mites and fungi.

The amount of the active ingredient used depends upon various factors such as for example the purpose of application, growth state of crops, weather, environmental conditions, the form of the composition, the mode of application, the type of fields to be treated, and the like.

In applying the present fungicidal compositions alone, the dosage of the present active ingredient is preferably selected from a range of from 0.1 to 500 g per 10 ares.

Furthermore, the present compounds can be applied in the form of mixed formulations with other fungicides, insecticides, fertilizers and plant growth regulators, as far as such agents can be used in combination with the present compounds.

Examples of pesticides usable in admixture with the insecticide of the present invention will be shown below:

O,O-dimethyl O-(4-nitro-3-methylphenyl)thiophosphate (Phenitrothion)
O,O-dimethyl O-(3-methyl-4-methylthiophenyl)thiophosphate (Baycid)
O,O-dimethyl S-(carbethoxyphenylmethyl)dithiophosphate (Elsan)
O,O-diethyl O-(2-isopropyl-4-methylpyrimidyl-6)thiophosphate (Diazinon)
O,O-dimethyl 2,2,2-trichloro-1-hydroxyethylphosphate (Dipterex)
O-ethyl O-p-cyanophenyl phenylphosphonothioate (Surecide)
O-ethyl O-p-nitrophenyl phenylthiophosphonate (EPN)
O,O-dipropyl O-4-methylthiophenylphosphate (Propaphos)
O,O-dimethyl S-phthalimidomethyl dithiophosphate (Imidan)
O,O-dimethyl O-dichlorovinyl phosphate (DDVP)
O,O-dimethyl S-(N-methylcarbamoylmethyl)dithiophosphate (Dimethoate)
O,O-dimethyl S-(1,2-dicarbethoxyethyl)dithiophosphate (Malathon)
1-Naphthyl N-methylcarbamate (NAC)
m-Tolyl N-methylcarbamate (MTMC)
2-Isopropoxyphenyl N-methylcarbamate (PHC)
Ethyl N-(diethyl-dithiophosphorylacetyl)-N-methylcarbamate (Mecarbam)
3,4-Xylyl N-methylcarbamate (MPMC)
2-s-Butylphenyl N-methylcarbamate (BPMC)
2-Isopropylphenyl N-methylcarbamate (MIPC)
2-Chlorophenyl N-methylcarbamate (CPMC)
3,5-Xylyl N-methylcarbamate (XMC)
2-(1,3-Dioxolan-2-)phenyl N-methylcarbamate (Dioxacarb)
3-tert-Butylphenyl N-methylcarbamate (Terbam)
4-Diallylamino-3,5-dimethylphenyl N-methylcarbamate (APC)
S-methyl-N-(methylcarbamoyloxy) thioacetoimidate (Methomil)

N-(2-methyl-4-chlorophenyl)-N,N-dimethylformamidine hydrochloride (Chlorophenamidine)
1,3-Bis(carbamoylthio)-2-(N,N-dimethylamino)propane hydrochloride (Cartap)
Diisopropyl-1,3-dithiolan-2-ylidene malonate (Isoprothiolan)
N-[[(4-chlorophenyl)amino]carbonyl]-2,6-difluorobenzamide (Diflubenzuron)
O,O-Dimethyl-S-[2-(isopropylthio)ethyl]-phosphorodithioate (Isothioate)
O,O-Diethyl-S-[2-(ethylthio)ethyl]-phosphorodithioate (Disulfoton)
2,3-Dihydro-2,2-dimethylbenzofuran-7-yl methylcarbamate (Carbofuran)
O-Ethyl S,S-diphenyl phosphorodithioate (Edibenfos)
N-(trichloromethylthio)cyclohex-4-ene-1,2-dicarboxamide (Captan)
2,4,5,6-Tetrachloro-1,3-isophthalonitril (Chlorothalonil)
N-(1,1,2,2-tetrachloroethylthio)cyclohex-4-ene-1,2-dicarboxamide (Captafol)
Dimethyl 4,4-o-phenylene bis(3-thioallophanate) (Thiophanate methyl)
Methyl 3-(butylcarbamoyl)-3H-benzimidazol-2-ylcarbamate (Benomyl)
Zinc ethylenebis(dithiocarbamate)(polymeric) (Zineb)
Manganese ethylenebis(dithiocarbamate)(polymeric) (Maneb)

In order to demonstrate the effectiveness of the present compounds, some test examples and formulation examples will be shown below, but the present invention is not limited to these examples only.

TEST EXAMPLE 1

Fungicidal activity against the powdery mildow of barley (*Erysiphe graminis* f. sp. hordei)

Barley seedlings at 2-leaf stage were sprayed with test compound (200 ppm) one day after inoculation with conidia of *Erysiphe graminis* f. sp. hordei. The seedlings were kept in a constant-temperature room at 25° C. for one week and the percentage of the infected area per leaf was examined. The fungicidal activity was judged based on the following criterion in comparison with the untreated plot.

The results are shown in Table 2.

TABLE 2

| Compound No. | Fungicidal activity | Compound No. | Fungicidal activity | Compound No. | Fungicidal activity |
|---|---|---|---|---|---|
| 4 | B | 55 | A | 97 | C |
| 9 | C | 56 | A | 98 | A |
| 16 | B | 57 | C | 102 | A |
| 17 | A | 58 | C | 103 | C |
| 18 | B | 59 | A | 105 | A |
| 19 | A | 60 | A | 109 | A |
| 20 | B | 66 | A | 110 | B |
| 21 | A | 67 | A | 111 | A |
| 22 | A | 68 | A | 112 | A |
| 23 | A | 69 | A | 113 | A |
| 24 | A | 71 | B | 114 | A |
| 25 | A | 73 | A | 118 | B |
| 26 | A | 74 | A | 119 | C |
| 27 | A | 85 | A | 120 | B |
| 33 | A | 86 | A | 123 | A |
| 34 | A | 87 | A | 124 | B |
| 35 | A | 88 | A | 133 | A |
| 36 | A | 89 | A | 134 | B |
| 41 | A | 90 | A | 136 | A |
| 42 | A | 91 | A | 140 | B |
| 50 | A | 92 | A | 142 | C |
| 51 | A | 93 | B | 144 | C |

TABLE 2-continued

| Compound No. | Fungicidal activity | Compound No. | Fungicidal activity | Compound No. | Fungicidal activity |
|---|---|---|---|---|---|
| 52 | B | 94 | A | 145 | A |
| 53 | A | 95 | B | 153 | A |
| 54 | A | 96 | C | 154 | A |
| 155 | A | 212 | A | 249 | C |
| 156 | A | 213 | A | 250 | A |
| 157 | A | 216 | A | 251 | B |
| 158 | A | 217 | B | 252 | A |
| 159 | A | 219 | C | 253 | A |
| 160 | A | 220 | A | 254 | A |
| 161 | B | 221 | A | 255 | A |
| 167 | A | 222 | C | 257 | B |
| 181 | C | 228 | B | 258 | B |
| 186 | B | 229 | A | 262 | B |
| 188 | A | 230 | A | 263 | A |
| 190 | C | 231 | A | 264 | A |
| 193 | A | 232 | A | 265 | A |
| 194 | A | 234 | A | 266 | A |
| 195 | A | 235 | A | 267 | A |
| 197 | A | 236 | C | 268 | A |
| 198 | A | 237 | A | 269 | B |
| 199 | A | 238 | C | 270 | B |
| 200 | A | 239 | A | 281 | B |
| 201 | A | 240 | A | 282 | C |
| 202 | A | 241 | A | 283 | A |
| 203 | A | 242 | A | 300 | C |
| 204 | B | 243 | A | 302 | B |
| 205 | A | 245 | A | 303 | B |
| 206 | C | 246 | B | 304 | B |
| 207 | C | 248 | A | 305 | B |
| 306 | A | 351 | A | 391 | A |
| 309 | B | 352 | B | 392 | A |
| 311 | C | 353 | A | 393 | A |
| 312 | B | 356 | A | 394 | A |
| 315 | A | 357 | A | 395 | A |
| 316 | A | 358 | A | 396 | A |
| 321 | A | 363 | A | 397 | A |
| 323 | A | 364 | A | 398 | A |
| 324 | C | 365 | A | 399 | A |
| 328 | B | 366 | A | 400 | A |
| 329 | A | 369 | A | 401 | A |
| 330 | A | 370 | A | 402 | A |
| 331 | A | 371 | C | 403 | A |
| 332 | A | 372 | A | 404 | A |
| 333 | A | 373 | C | 405 | A |
| 334 | A | 374 | A | 406 | A |
| 336 | B | 375 | A | 407 | A |
| 337 | B | 382 | A | 409 | A |
| 340 | A | 383 | A | 421 | A |
| 342 | A | 384 | A | 422 | A |
| 343 | A | 385 | A | 424 | A |
| 344 | A | 386 | A | 427 | A |
| 346 | A | 387 | A | 428 | A |
| 347 | A | 388 | C | 429 | A |
| 349 | B | 389 | A | 431 | A |
| 350 | A | 390 | A | 432 | B |
| 433 | A | 470 | B | 496 | A |
| 434 | A | 471 | A | 497 | A |
| 435 | B | 472 | A | 498 | A |
| 436 | A | 473 | A | 499 | A |
| 437 | A | 474 | A | 501 | A |
| 438 | A | 475 | B | 502 | A |
| 439 | A | 476 | A | 503 | A |
| 440 | A | 477 | A | 504 | A |
| 441 | A | 478 | B | 505 | A |
| 443 | A | 479 | A | 506 | A |
| 444 | A | 480 | A | 507 | A |
| 445 | A | 481 | A | 508 | A |
| 446 | A | 482 | A | 518 | C |
| 447 | A | 483 | A | 522 | B |
| 448 | A | 484 | A | 523 | B |
| 449 | A | 485 | A | 524 | B |
| 450 | A | 486 | A | 527 | A |
| 451 | A | 487 | A | 528 | A |
| 452 | A | 488 | B | 529 | B |
| 453 | A | 489 | B | 530 | B |
| 454 | A | 490 | B | 532 | A |
| 455 | A | 491 | C | 533 | A |
| 465 | A | 492 | B | 534 | C |
| 466 | A | 493 | A | 535 | B |

TABLE 2-continued

| Compound No. | Fungicidal activity | Compound No. | Fungicidal activity | Compound No. | Fungicidal activity |
|---|---|---|---|---|---|
| 468 | A | 494 | A | 536 | A |
| 469 | A | 495 | A | 537 | B |
| 538 | A | 574 | B | 612 | A |
| 541 | A | 576 | A | 613 | A |
| 545 | A | 578 | B | 614 | A |
| 546 | A | 579 | B | 615 | A |
| 547 | A | 580 | B | 616 | A |
| 548 | A | 581 | C | 617 | A |
| 549 | B | 584 | B | 618 | A |
| 550 | C | 586 | C | 619 | A |
| 551 | C | 587 | B | 620 | A |
| 552 | C | 589 | A | 621 | A |
| 553 | A | 591 | B | 622 | A |
| 554 | C | 592 | A | 623 | A |
| 555 | C | 593 | A | 624 | A |
| 556 | B | 594 | B | 625 | A |
| 557 | A | 595 | C | 626 | A |
| 562 | A | 596 | C | 627 | B |
| 563 | A | 597 | C | 628 | B |
| 565 | A | 598 | C | 629 | A |
| 566 | A | 601 | C | 630 | A |
| 567 | A | 602 | A | 631 | A |
| 568 | A | 603 | A | 636 | A |
| 569 | B | 604 | A | 637 | A |
| 570 | A | 608 | A | 638 | A |
| 571 | A | 609 | A | 639 | A |
| 572 | B | 610 | A | 640 | A |
| 573 | B | 611 | A | 641 | B |
| 642 | C | 677 | A | 727 | A |
| 643 | A | 678 | A | 729 | A |
| 644 | B | 680 | A | 730 | B |
| 645 | A | 682 | A | 731 | B |
| 646 | A | 683 | A | 732 | A |
| 648 | A | 684 | A | 733 | A |
| 649 | A | 691 | B | 737 | A |
| 650 | B | 692 | B | 739 | C |
| 652 | C | 693 | A | 740 | A |
| 653 | B | 694 | A | 741 | A |
| 654 | B | 695 | A | 746 | B |
| 655 | A | 696 | B | 751 | B |
| 656 | B | 697 | B | 753 | B |
| 657 | B | 700 | C | 754 | A |
| 658 | A | 701 | A | 755 | A |
| 659 | B | 702 | B | 757 | A |
| 660 | A | 707 | B | 758 | A |
| 661 | B | 708 | A | 759 | A |
| 662 | B | 713 | A | 763 | B |
| 663 | A | 715 | A | 766 | A |
| 667 | C | 716 | B | 767 | A |
| 668 | A | 718 | C | 768 | A |
| 670 | A | 719 | A | 769 | A |
| 672 | B | 720 | B | 772 | B |
| 675 | B | 724 | A | 773 | A |
| 676 | B | 726 | B | 775 | B |
| 783 | B | 823 | A | 841 | B |
| 784 | B | 824 | A | 842 | A |
| 795 | A | 825 | A | 843 | A |
| 796 | B | 827 | B | 844 | A |
| 803 | A | 828 | C | 848 | A |
| 804 | C | 829 | A | 849 | A |
| 805 | C | 831 | C | 850 | A |
| 816 | A | 833 | B | 851 | A |
| 817 | A | 834 | A | 852 | B |
| 818 | A | 835 | B | 853 | A |
| 819 | A | 836 | A | 854 | C |
| 821 | B | 839 | A | 855 | A |
| 822 | B | 840 | B | | |

A: Control of disease 100–95%
B: Control of disease 94–80%
C: Control of disease 79–60%
D: Control of disease 59–0%

TEST EXAMPLE 2

Fungicidal activity against the crown rust of oat (*Puccinia coronata* f.sp. avenae)

Oat seedling at 8-leaf stage were sprayed with test compound (200 ppm) one day after inoculation with uredospores of *Puccinia coronata* f.sp. avenae. The seedlings were kept in a constant-temperature room at 25° C. for ten days and the percentage of the infected area per leaf was examined. The fungicidal activity was judged according to the same criterion as in Test example 1.

The results are shown in Table 3.

TABLE 3

| Compound No. | Fungicidal activity | Compound No. | Fungicidal activity | Compound No. | Fungicidal activity |
|---|---|---|---|---|---|
| 14 | B | 60 | A | 111 | A |
| 18 | C | 66 | A | 112 | A |
| 19 | C | 67 | A | 113 | A |
| 21 | C | 68 | A | 114 | A |
| 22 | B | 69 | A | 133 | A |
| 23 | B | 71 | A | 134 | A |
| 24 | B | 73 | A | 135 | B |
| 25 | B | 74 | A | 136 | A |
| 27 | A | 85 | A | 138 | A |
| 33 | A | 86 | A | 139 | A |
| 34 | A | 87 | A | 140 | A |
| 35 | A | 88 | B | 142 | A |
| 36 | A | 89 | A | 143 | A |
| 41 | A | 90 | A | 144 | A |
| 42 | A | 91 | A | 145 | A |
| 50 | A | 92 | C | 153 | A |
| 51 | A | 93 | B | 154 | A |
| 52 | A | 94 | B | 155 | A |
| 53 | A | 95 | A | 156 | A |
| 54 | A | 96 | A | 157 | A |
| 55 | A | 97 | C | 158 | A |
| 56 | A | 98 | A | 159 | B |
| 57 | A | 105 | A | 160 | B |
| 58 | A | 109 | A | 161 | A |
| 59 | A | 110 | A | 186 | A |
| 188 | A | 241 | A | 328 | A |
| 193 | A | 242 | B | 329 | A |
| 194 | A | 243 | A | 330 | A |
| 195 | A | 245 | A | 331 | A |
| 198 | A | 246 | A | 332 | A |
| 199 | A | 248 | C | 333 | A |
| 200 | A | 250 | A | 337 | A |
| 201 | B | 251 | A | 340 | B |
| 202 | C | 254 | B | 342 | A |
| 203 | A | 257 | A | 343 | A |
| 204 | B | 258 | A | 344 | A |
| 205 | B | 263 | A | 345 | B |
| 212 | A | 264 | A | 346 | A |
| 213 | C | 265 | A | 347 | A |
| 217 | C | 266 | B | 349 | A |
| 220 | B | 267 | B | 350 | A |
| 221 | A | 268 | B | 351 | B |
| 228 | B | 283 | B | 353 | A |
| 229 | A | 303 | C | 355 | C |
| 230 | A | 305 | B | 356 | A |
| 231 | A | 306 | A | 357 | A |
| 234 | A | 309 | C | 358 | A |
| 237 | A | 312 | A | 363 | A |
| 238 | B | 315 | A | 364 | A |
| 239 | A | 316 | A | 366 | A |
| 240 | A | 323 | B | 369 | A |
| 370 | A | 402 | A | 446 | C |
| 371 | A | 403 | A | 447 | A |
| 372 | A | 404 | A | 448 | A |
| 373 | A | 405 | A | 449 | A |
| 374 | A | 406 | A | 450 | A |
| 375 | A | 407 | A | 451 | A |
| 381 | C | 409 | A | 452 | A |
| 382 | A | 421 | A | 453 | A |
| 383 | A | 422 | A | 454 | A |
| 384 | A | 427 | C | 455 | A |
| 385 | A | 428 | A | 465 | A |
| 386 | A | 429 | A | 468 | A |
| 387 | B | 431 | A | 469 | A |
| 388 | C | 433 | A | 470 | A |
| 390 | A | 434 | A | 471 | A |
| 391 | A | 435 | B | 472 | A |
| 392 | A | 436 | A | 473 | A |
| 393 | A | 437 | A | 474 | A |

TABLE 3-continued

| Compound No. | Fungicidal activity | Compound No. | Fungicidal activity | Compound No. | Fungicidal activity |
|---|---|---|---|---|---|
| 394 | A | 438 | C | 475 | A |
| 395 | A | 439 | A | 476 | B |
| 396 | A | 440 | A | 477 | A |
| 397 | A | 441 | A | 478 | A |
| 398 | A | 442 | A | 479 | A |
| 399 | A | 443 | B | 480 | A |
| 400 | A | 444 | A | 481 | C |
| 401 | A | 445 | B | 482 | A |
| 483 | A | 523 | A | 557 | A |
| 484 | A | 524 | A | 558 | C |
| 485 | A | 525 | A | 559 | C |
| 486 | A | 527 | C | 560 | B |
| 487 | A | 528 | A | 561 | A |
| 488 | A | 529 | A | 562 | B |
| 489 | A | 530 | A | 563 | A |
| 490 | A | 531 | A | 565 | A |
| 491 | A | 532 | A | 566 | A |
| 492 | A | 533 | A | 567 | A |
| 493 | A | 534 | A | 568 | A |
| 494 | A | 535 | A | 569 | A |
| 495 | A | 536 | A | 570 | A |
| 496 | A | 537 | A | 571 | A |
| 497 | A | 538 | A | 572 | A |
| 498 | A | 544 | B | 573 | C |
| 499 | A | 545 | A | 574 | B |
| 500 | C | 546 | A | 576 | A |
| 501 | A | 548 | A | 577 | A |
| 502 | A | 550 | C | 578 | A |
| 503 | A | 551 | A | 579 | A |
| 504 | A | 552 | C | 580 | A |
| 505 | A | 553 | B | 585 | C |
| 506 | A | 554 | A | 586 | A |
| 507 | A | 555 | A | 587 | A |
| 508 | A | 556 | A | 589 | A |
| 590 | A | 621 | A | 651 | B |
| 591 | A | 622 | A | 652 | A |
| 592 | A | 623 | A | 653 | B |
| 593 | A | 624 | A | 654 | A |
| 594 | A | 625 | A | 655 | A |
| 595 | A | 626 | A | 656 | A |
| 596 | B | 627 | A | 657 | A |
| 599 | B | 628 | A | 658 | A |
| 602 | A | 629 | A | 659 | B |
| 603 | A | 630 | A | 660 | A |
| 604 | A | 631 | A | 661 | A |
| 606 | C | 636 | A | 662 | A |
| 607 | A | 637 | A | 663 | A |
| 608 | A | 638 | A | 667 | C |
| 609 | A | 639 | A | 668 | A |
| 610 | A | 640 | A | 669 | B |
| 611 | A | 641 | A | 670 | B |
| 612 | A | 642 | A | 672 | B |
| 613 | A | 643 | A | 674 | B |
| 614 | A | 644 | A | 675 | A |
| 615 | A | 645 | A | 677 | A |
| 616 | A | 646 | A | 678 | A |
| 617 | A | 647 | A | 679 | B |
| 618 | A | 648 | A | 680 | A |
| 619 | A | 649 | A | 682 | A |
| 620 | A | 650 | A | 683 | A |
| 684 | A | 727 | A | 784 | B |
| 685 | A | 729 | A | 794 | C |
| 690 | C | 730 | A | 796 | A |
| 691 | C | 731 | A | 804 | A |
| 692 | A | 732 | A | 812 | B |
| 693 | A | 733 | A | 813 | A |
| 694 | A | 737 | B | 814 | B |
| 695 | A | 746 | B | 815 | B |
| 696 | A | 751 | B | 817 | C |
| 697 | A | 755 | A | 821 | A |
| 699 | A | 757 | B | 822 | C |
| 701 | A | 758 | A | 823 | A |
| 706 | B | 759 | A | 824 | A |
| 709 | A | 763 | A | 825 | A |
| 710 | A | 764 | B | 829 | A |
| 711 | A | 766 | A | 830 | C |
| 712 | A | 767 | A | 831 | A |
| 713 | B | 768 | A | 832 | C |
| 715 | B | 769 | A | 833 | A |
| 717 | C | 770 | B | 834 | A |
| 719 | A | 772 | A | 835 | A |
| 720 | C | 773 | A | 838 | A |
| 723 | B | 780 | B | 842 | A |
| 724 | A | 781 | C | 843 | A |
| 725 | A | 782 | A | 844 | A |
| 726 | A | 783 | B | 848 | A |
| 849 | B | 851 | A | 853 | A |
| 850 | A | 852 | B | 854 | A |

TEST EXAMPLE 3

Fungicidal activity against the downy mildew of cucumber (*Pseudoperonospora cubensis*)

Cucumber plants at 2-leaf stage were sprayed with test compound (200 ppm) one day before inoculation with zoospores of *Psudopernospora cubensis*. After the plants were kept in a humid room at 25° C. one day and then in a greenhouse for six days, the degree of infection per leaf was examined and the fungicidal activity was judged according to the same criterion as in Test example 1.

The results are shown in Table 4.

TABLE 4

| Compound No. | Fungicidal activity |
|---|---|
| 4 | B |
| 9 | A |
| 10 | B |
| 12 | C |
| 13 | B |
| 16 | C |
| 17 | A |
| 18 | C |
| 19 | A |
| 20 | B |
| 21 | A |
| 22 | A |
| 23 | A |
| 24 | A |
| 25 | A |
| 26 | A |
| 27 | A |
| 33 | A |
| 34 | A |
| 36 | A |
| 41 | A |
| 42 | A |
| 45 | A |
| 47 | C |
| 50 | A |
| 51 | B |
| 52 | B |
| 53 | C |
| 54 | A |
| 55 | A |
| 56 | A |
| 57 | A |
| 58 | C |
| 59 | C |
| 60 | A |
| 65 | C |
| 66 | A |
| 67 | A |
| 68 | A |
| 69 | B |
| 73 | C |
| 74 | A |
| 75 | B |
| 77 | B |
| 78 | A |
| 79 | C |

TABLE 4-continued

| Compound No. | Fungicidal activity |
|---|---|
| 85 | A |
| 86 | B |
| 87 | A |
| 88 | C |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 103 | B |
| 104 | C |
| 105 | B |
| 109 | B |
| 110 | A |
| 111 | A |
| 112 | B |
| 113 | A |
| 114 | A |
| 115 | A |
| 116 | A |
| 117 | B |
| 118 | B |
| 121 | C |
| 122 | A |
| 123 | B |
| 130 | A |
| 131 | A |
| 133 | C |
| 136 | A |
| 137 | B |
| 138 | B |
| 139 | A |
| 140 | A |
| 141 | C |
| 145 | B |
| 147 | A |
| 153 | B |
| 154 | A |
| 155 | A |
| 156 | A |
| 159 | C |
| 160 | B |
| 161 | A |
| 162 | A |
| 171 | C |
| 173 | A |
| 178 | A |
| 179 | A |
| 180 | A |
| 181 | C |
| 182 | A |
| 183 | B |
| 186 | C |
| 188 | A |
| 192 | A |
| 193 | A |
| 194 | A |
| 195 | B |
| 196 | B |
| 197 | A |
| 198 | A |
| 199 | A |
| 200 | A |
| 201 | B |
| 202 | B |
| 203 | A |
| 204 | A |
| 205 | A |
| 212 | A |
| 213 | A |
| 216 | C |
| 220 | B |
| 221 | A |
| 228 | B |
| 229 | B |
| 230 | B |
| 231 | C |
| 232 | B |
| 234 | A |
| 237 | A |
| 239 | C |
| 240 | A |
| 242 | C |
| 243 | A |
| 245 | A |
| 246 | B |
| 251 | C |
| 252 | B |
| 253 | A |
| 254 | A |
| 255 | B |
| 256 | B |
| 257 | C |
| 258 | C |
| 262 | C |
| 263 | C |
| 264 | C |
| 265 | A |
| 266 | B |
| 267 | C |
| 269 | B |
| 270 | C |
| 284 | C |
| 288 | C |
| 292 | A |
| 293 | B |
| 296 | B |
| 297 | A |
| 298 | C |
| 299 | A |
| 302 | A |
| 303 | C |
| 304 | A |
| 305 | B |
| 306 | B |
| 312 | B |
| 316 | C |
| 321 | A |
| 326 | B |
| 328 | B |
| 329 | B |
| 330 | B |
| 331 | A |
| 332 | A |
| 333 | A |
| 336 | A |
| 337 | B |
| 342 | A |
| 343 | C |
| 344 | B |
| 346 | A |
| 350 | B |
| 351 | A |
| 352 | B |
| 353 | A |
| 354 | C |
| 355 | C |
| 356 | A |
| 357 | A |
| 358 | A |
| 363 | A |
| 364 | A |
| 365 | A |
| 366 | A |
| 369 | A |
| 370 | A |
| 371 | B |
| 372 | A |
| 373 | A |
| 374 | A |
| 375 | A |
| 376 | B |

TABLE 4-continued

| Compound No. | Fungicidal activity |
|---|---|
| 377 | B |
| 378 | C |
| 383 | A |
| 385 | A |
| 386 | B |
| 387 | B |
| 388 | A |
| 389 | B |
| 390 | A |
| 391 | A |
| 392 | A |
| 393 | A |
| 394 | A |
| 395 | A |
| 396 | A |
| 397 | A |
| 398 | A |
| 399 | A |
| 400 | A |
| 401 | A |
| 402 | A |
| 403 | A |
| 404 | A |
| 405 | A |
| 406 | A |
| 407 | A |
| 409 | A |
| 420 | B |
| 421 | A |
| 424 | A |
| 428 | B |
| 429 | A |
| 431 | A |
| 432 | B |
| 433 | B |
| 434 | B |
| 436 | A |
| 437 | A |
| 438 | A |
| 439 | A |
| 440 | A |
| 441 | A |
| 442 | B |
| 444 | A |
| 445 | A |
| 446 | B |
| 447 | A |
| 448 | B |
| 449 | A |
| 450 | A |
| 451 | A |
| 452 | A |
| 453 | A |
| 454 | A |
| 455 | A |
| 465 | A |
| 468 | A |
| 469 | A |
| 471 | A |
| 473 | C |
| 474 | C |
| 476 | B |
| 477 | A |
| 478 | A |
| 479 | B |
| 480 | A |
| 481 | A |
| 482 | A |
| 483 | B |
| 484 | A |
| 485 | A |
| 486 | A |
| 487 | A |
| 488 | A |
| 489 | A |
| 490 | A |
| 491 | B |
| 492 | C |
| 493 | B |
| 496 | A |
| 497 | A |
| 498 | C |
| 499 | C |
| 502 | C |
| 503 | C |
| 504 | A |
| 505 | C |
| 506 | A |
| 507 | A |
| 508 | A |
| 511 | A |
| 512 | A |
| 513 | A |
| 514 | A |
| 515 | A |
| 516 | B |
| 518 | C |
| 523 | A |
| 524 | A |
| 525 | A |
| 527 | B |
| 528 | A |
| 529 | B |
| 531 | C |
| 532 | A |
| 533 | A |
| 534 | A |
| 535 | A |
| 536 | A |
| 537 | A |
| 538 | A |
| 541 | B |
| 544 | A |
| 546 | A |
| 548 | A |
| 551 | A |
| 553 | C |
| 554 | C |
| 555 | B |
| 556 | C |
| 557 | B |
| 562 | A |
| 563 | A |
| 565 | A |
| 566 | A |
| 567 | B |
| 568 | B |
| 569 | A |
| 570 | A |
| 572 | A |
| 574 | B |
| 576 | A |
| 577 | A |
| 578 | C |
| 579 | B |
| 584 | B |
| 585 | B |
| 586 | A |
| 588 | C |
| 589 | A |
| 590 | A |
| 591 | A |
| 592 | A |
| 593 | A |
| 594 | A |
| 595 | A |
| 596 | C |
| 597 | C |
| 598 | C |
| 599 | B |
| 602 | A |
| 603 | A |
| 604 | A |
| 605 | A |
| 608 | A |
| 609 | A |
| 610 | A |
| 611 | A |
| 612 | A |
| 613 | A |

TABLE 4-continued

| Compound No. | Fungicidal activity |
|---|---|
| 614 | A |
| 615 | A |
| 616 | A |
| 617 | A |
| 618 | A |
| 619 | A |
| 620 | A |
| 621 | A |
| 622 | B |
| 623 | A |
| 624 | A |
| 625 | A |
| 626 | A |
| 627 | A |
| 628 | A |
| 629 | A |
| 630 | A |
| 631 | C |
| 632 | A |
| 633 | A |
| 636 | A |
| 637 | A |
| 638 | A |
| 639 | A |
| 640 | A |
| 641 | A |
| 642 | A |
| 643 | C |
| 644 | B |
| 645 | A |
| 646 | A |
| 647 | A |
| 648 | A |
| 649 | A |
| 650 | A |
| 651 | A |
| 652 | A |
| 653 | A |
| 654 | A |
| 655 | A |
| 656 | A |
| 657 | A |
| 658 | A |
| 659 | A |
| 660 | A |
| 661 | A |
| 662 | A |
| 663 | A |
| 668 | A |
| 669 | A |
| 670 | A |
| 673 | B |
| 674 | A |
| 675 | A |
| 676 | A |
| 677 | A |
| 678 | A |
| 680 | A |
| 681 | A |
| 682 | A |
| 683 | A |
| 684 | A |
| 685 | A |
| 686 | A |
| 690 | B |
| 691 | A |
| 692 | A |
| 693 | A |
| 694 | A |
| 695 | A |
| 696 | A |
| 697 | A |
| 698 | A |
| 699 | C |
| 700 | C |
| 701 | A |
| 702 | A |
| 705 | A |
| 706 | C |
| 709 | A |
| 713 | A |
| 714 | B |
| 715 | B |
| 716 | B |
| 717 | A |
| 719 | B |
| 720 | A |
| 725 | B |
| 726 | B |
| 727 | B |
| 728 | B |
| 729 | A |
| 730 | A |
| 731 | B |
| 732 | A |
| 733 | A |
| 737 | C |
| 739 | B |
| 740 | B |
| 741 | A |
| 742 | A |
| 746 | A |
| 751 | A |
| 752 | A |
| 754 | B |
| 755 | A |
| 756 | A |
| 757 | A |
| 758 | A |
| 759 | A |
| 761 | C |
| 763 | C |
| 764 | A |
| 765 | B |
| 766 | A |
| 767 | A |
| 768 | A |
| 769 | A |
| 770 | B |
| 772 | A |
| 773 | A |
| 774 | A |
| 775 | A |
| 776 | A |
| 777 | A |
| 780 | A |
| 782 | B |
| 783 | A |
| 784 | A |
| 787 | B |
| 789 | B |
| 804 | A |
| 812 | A |
| 813 | A |
| 814 | A |
| 815 | C |
| 817 | C |
| 820 | C |
| 821 | A |
| 822 | A |
| 823 | A |
| 824 | A |
| 825 | A |
| 826 | B |
| 827 | B |
| 828 | B |
| 829 | A |
| 831 | A |
| 833 | A |
| 834 | A |
| 835 | A |
| 836 | A |
| 837 | B |
| 838 | C |
| 839 | C |
| 840 | C |
| 841 | C |
| 842 | A |
| 843 | A |
| 844 | A |

TABLE 4-continued

| Compound No. | Fungicidal activity |
|---|---|
| 845 | B |
| 848 | A |
| 849 | A |
| 850 | A |
| 851 | A |
| 852 | A |
| 853 | A |
| 854 | A |
| 855 | A |

TEST EXAMPLE 4

Insecticidal activity against the brown planthopper (*Nilaparvata lugens*)

Rice seedlings were dipped into the aqueous emulsion of the compound at 200 ppm for 30 seconds. After air-drying, the seedling were placed in a glass tube, and the 3rd instar nymphs were inoculated on the plants. On 8th day after treatment, the corrected mortality was caluculated and the insecticidal activity was judged based on the following criterion.

The results are shown in Table 5.

TABLE 5

| Compound No. | Insecticidal activity |
|---|---|
| 16 | A |
| 17 | A |
| 19 | A |
| 20 | A |
| 21 | A |
| 22 | A |
| 23 | A |
| 27 | A |
| 32 | A |
| 33 | A |
| 34 | A |
| 35 | A |
| 36 | A |
| 40 | C |
| 41 | A |
| 42 | A |
| 54 | A |
| 55 | A |
| 56 | B |
| 60 | A |
| 65 | C |
| 66 | A |
| 67 | A |
| 68 | A |
| 69 | A |
| 71 | A |
| 72 | B |
| 73 | A |
| 74 | A |
| 85 | A |
| 86 | A |
| 87 | A |
| 88 | A |
| 89 | A |
| 90 | A |
| 91 | A |
| 92 | A |
| 95 | A |
| 96 | C |
| 102 | A |
| 103 | A |
| 104 | A |
| 105 | A |
| 109 | A |
| 110 | A |
| 111 | A |
| 112 | A |
| 113 | A |
| 114 | A |
| 122 | A |
| 123 | A |
| 124 | A |
| 125 | A |
| 133 | A |
| 134 | A |
| 135 | A |
| 136 | A |
| 140 | A |
| 154 | A |
| 155 | A |
| 157 | A |
| 158 | A |
| 159 | A |
| 160 | A |
| 161 | A |
| 166 | A |
| 193 | A |
| 194 | A |
| 195 | A |
| 198 | A |
| 199 | B |
| 200 | A |
| 203 | A |
| 204 | A |
| 211 | C |
| 212 | A |
| 214 | B |
| 217 | C |
| 221 | A |
| 229 | A |
| 230 | A |
| 231 | A |
| 232 | A |
| 234 | A |
| 235 | B |
| 236 | A |
| 237 | A |
| 239 | A |
| 240 | A |
| 241 | A |
| 242 | A |
| 248 | A |
| 250 | A |
| 255 | A |
| 257 | A |
| 258 | A |
| 260 | C |
| 266 | A |
| 267 | A |
| 268 | C |
| 269 | C |
| 283 | A |
| 302 | A |
| 303 | B |
| 304 | C |
| 305 | C |
| 306 | A |
| 310 | A |
| 311 | A |
| 314 | C |
| 315 | A |
| 316 | A |
| 321 | A |
| 328 | A |
| 329 | A |
| 330 | A |
| 331 | A |
| 332 | A |
| 333 | A |
| 334 | A |
| 336 | A |
| 337 | A |
| 339 | C |
| 340 | A |
| 342 | A |
| 343 | A |
| 344 | A |
| 345 | A |
| 346 | C |

TABLE 5-continued

| Compound No. | Insecticidal activity |
|---|---|
| 347 | A |
| 349 | A |
| 350 | A |
| 351 | A |
| 352 | A |
| 353 | A |
| 355 | A |
| 356 | A |
| 357 | A |
| 358 | A |
| 363 | A |
| 364 | A |
| 365 | A |
| 366 | A |
| 369 | A |
| 370 | A |
| 371 | A |
| 372 | A |
| 373 | A |
| 374 | A |
| 375 | A |
| 388 | A |
| 389 | A |
| 390 | A |
| 391 | A |
| 392 | A |
| 394 | A |
| 395 | A |
| 396 | A |
| 397 | A |
| 398 | A |
| 399 | A |
| 400 | B |
| 401 | A |
| 402 | A |
| 403 | A |
| 404 | A |
| 405 | A |
| 406 | A |
| 407 | A |
| 409 | A |
| 421 | A |
| 422 | A |
| 424 | A |
| 427 | A |
| 428 | A |
| 429 | A |
| 431 | A |
| 433 | A |
| 434 | A |
| 435 | B |
| 436 | A |
| 437 | A |
| 438 | A |
| 439 | A |
| 440 | A |
| 441 | B |
| 442 | A |
| 443 | A |
| 444 | B |
| 445 | C |
| 446 | B |
| 447 | A |
| 448 | A |
| 449 | A |
| 450 | A |
| 451 | A |
| 452 | A |
| 453 | A |
| 454 | A |
| 465 | A |
| 466 | A |
| 467 | A |
| 468 | A |
| 469 | A |
| 470 | A |
| 471 | A |
| 472 | A |
| 473 | A |
| 474 | A |
| 475 | A |
| 476 | A |
| 477 | A |
| 479 | A |
| 480 | A |
| 481 | A |
| 482 | A |
| 483 | A |
| 484 | A |
| 485 | A |
| 486 | A |
| 487 | A |
| 488 | A |
| 489 | A |
| 499 | A |
| 500 | B |
| 501 | A |
| 502 | A |
| 503 | A |
| 504 | A |
| 505 | A |
| 506 | A |
| 507 | A |
| 508 | A |
| 516 | C |
| 517 | A |
| 518 | A |
| 523 | A |
| 524 | A |
| 525 | A |
| 527 | A |
| 528 | A |
| 529 | A |
| 531 | A |
| 532 | A |
| 533 | A |
| 534 | A |
| 535 | A |
| 536 | A |
| 537 | A |
| 538 | A |
| 541 | A |
| 544 | A |
| 545 | A |
| 546 | A |
| 547 | A |
| 548 | A |
| 549 | A |
| 551 | A |
| 552 | A |
| 553 | A |
| 554 | A |
| 555 | A |
| 556 | A |
| 557 | A |
| 562 | A |
| 563 | A |
| 564 | A |
| 565 | A |
| 566 | A |
| 567 | A |
| 568 | A |
| 569 | A |
| 570 | A |
| 571 | A |
| 572 | A |
| 573 | A |
| 574 | A |
| 575 | A |
| 576 | A |
| 577 | B |
| 578 | B |
| 579 | A |
| 580 | B |
| 581 | A |
| 584 | B |
| 585 | A |
| 586 | A |
| 587 | A |
| 588 | B |

TABLE 5-continued

| Compound No. | Insecticidal activity |
|---|---|
| 589 | B |
| 594 | B |
| 595 | A |
| 602 | A |
| 603 | A |
| 604 | A |
| 608 | A |
| 609 | A |
| 610 | A |
| 611 | A |
| 612 | A |
| 613 | A |
| 614 | A |
| 615 | A |
| 616 | A |
| 617 | A |
| 618 | A |
| 619 | A |
| 620 | A |
| 621 | A |
| 623 | A |
| 624 | A |
| 625 | A |
| 626 | A |
| 627 | A |
| 628 | A |
| 629 | A |
| 630 | A |
| 631 | A |
| 636 | A |
| 637 | A |
| 638 | A |
| 639 | A |
| 640 | A |
| 641 | C |
| 642 | A |
| 643 | A |
| 644 | A |
| 645 | A |
| 646 | A |
| 647 | A |
| 648 | A |
| 649 | B |
| 652 | B |
| 653 | A |
| 654 | A |
| 655 | A |
| 656 | B |
| 657 | A |
| 658 | A |
| 659 | C |
| 660 | A |
| 661 | A |
| 662 | A |
| 663 | A |
| 668 | A |
| 669 | A |
| 670 | A |
| 671 | A |
| 672 | C |
| 673 | C |
| 674 | B |
| 675 | A |
| 677 | A |
| 679 | A |
| 680 | A |
| 682 | A |
| 683 | A |
| 684 | A |
| 685 | A |
| 686 | C |
| 691 | A |
| 692 | A |
| 693 | A |
| 694 | B |
| 695 | B |
| 696 | A |
| 697 | A |
| 698 | A |
| 699 | A |

TABLE 5-continued

| Compound No. | Insecticidal activity |
|---|---|
| 701 | A |
| 702 | A |
| 703 | C |
| 710 | C |
| 713 | A |
| 715 | A |
| 716 | A |
| 717 | A |
| 719 | A |
| 720 | C |
| 723 | B |
| 724 | A |
| 725 | A |
| 726 | A |
| 727 | A |
| 728 | A |
| 729 | A |
| 730 | C |
| 731 | A |
| 732 | A |
| 733 | A |
| 734 | A |
| 735 | A |
| 739 | B |
| 740 | A |
| 741 | A |
| 742 | A |
| 744 | A |
| 745 | A |
| 746 | A |
| 751 | A |
| 752 | C |
| 753 | A |
| 756 | A |
| 757 | A |
| 758 | A |
| 759 | A |
| 761 | A |
| 762 | A |
| 763 | A |
| 764 | A |
| 766 | A |
| 767 | A |
| 768 | A |
| 769 | A |
| 770 | A |
| 772 | A |
| 774 | A |
| 775 | A |
| 776 | A |
| 790 | A |
| 791 | A |
| 792 | C |
| 793 | A |
| 794 | A |
| 795 | A |
| 799 | A |
| 801 | C |
| 812 | C |
| 813 | A |
| 814 | C |
| 815 | C |
| 816 | A |
| 817 | A |
| 818 | C |
| 819 | C |
| 820 | A |
| 821 | A |
| 822 | A |
| 823 | A |
| 824 | A |
| 825 | A |
| 826 | A |
| 827 | A |
| 828 | A |
| 829 | A |
| 830 | A |
| 831 | A |
| 832 | A |
| 833 | A |

TABLE 5-continued

| Compound No. | Insecticidal activity |
|---|---|
| 834 | A |
| 835 | A |
| 836 | A |
| 837 | C |
| 838 | A |
| 839 | A |
| 840 | A |
| 841 | A |
| 842 | A |
| 843 | A |
| 844 | A |
| 845 | A |
| 847 | B |
| 848 | A |
| 849 | A |
| 850 | A |
| 851 | A |
| 852 | A |
| 853 | A |
| 854 | A |
| 855 | A |

A: Reviced Mortality 100–90%
B: Reviced Mortality 89–80%
C: Reviced Mortality 79–50%

TEST EXAMPLE 5

Insecticidal activity against the diamondback moth (*Plutella xylostella*)

Eggs laid on a leaf piece (6 cm×5 cm) of a chinese cabbage were dipped into the aqueous emulsion of the compound at 500 ppm for 30 seconds. After air-drying, the insects and the plant were placed in a petri dish. On 6th day after treatment, the corrected mortality was calculated and the insecticidal activity was judged according to the same criterion as in the test example 4.

The results are shown in Table 6.

TABLE 6

| Compound No. | Insecticidal activity | Compound No. | Insecticidal activity | Compound No. | Insecticidal activity |
|---|---|---|---|---|---|
| 8 | A | 74 | A | 133 | A |
| 18 | C | 85 | A | 136 | B |
| 26 | A | 86 | C | 142 | C |
| 27 | C | 87 | A | 154 | A |
| 33 | A | 88 | B | 155 | A |
| 34 | A | 89 | A | 156 | A |
| 35 | A | 90 | A | 157 | B |
| 36 | B | 91 | A | 158 | A |
| 41 | A | 92 | A | 159 | B |
| 42 | A | 94 | A | 160 | A |
| 51 | C | 95 | A | 169 | C |
| 52 | A | 97 | C | 192 | A |
| 53 | B | 98 | A | 193 | A |
| 54 | B | 102 | A | 195 | A |
| 55 | B | 103 | A | 196 | A |
| 56 | A | 104 | A | 197 | B |
| 57 | C | 105 | C | 198 | A |
| 59 | A | 109 | A | 199 | A |
| 60 | A | 110 | B | 200 | A |
| 66 | A | 111 | B | 201 | A |
| 67 | A | 112 | A | 202 | A |
| 68 | A | 113 | A | 203 | A |
| 69 | A | 122 | A | 204 | A |
| 72 | A | 123 | A | 205 | B |
| 73 | A | 126 | C | 206 | B |
| 207 | A | 251 | C | 328 | A |
| 212 | A | 252 | C | 329 | A |
| 213 | A | 253 | A | 330 | A |
| 215 | A | 254 | A | 331 | B |
| 216 | A | 255 | B | 333 | A |
| 217 | A | 256 | A | 337 | A |
| 220 | B | 257 | A | 340 | A |
| 221 | C | 262 | A | 342 | A |

TABLE 6-continued

| Compound No. | Insecticidal activity | Compound No. | Insecticidal activity | Compound No. | Insecticidal activity |
|---|---|---|---|---|---|
| 228 | A | 263 | A | 343 | A |
| 229 | A | 264 | A | 344 | A |
| 230 | A | 265 | C | 345 | B |
| 231 | A | 266 | A | 346 | A |
| 232 | B | 267 | A | 347 | A |
| 234 | B | 268 | A | 349 | A |
| 235 | A | 269 | C | 350 | A |
| 237 | C | 280 | B | 351 | A |
| 239 | B | 281 | A | 352 | A |
| 240 | A | 283 | A | 353 | A |
| 241 | A | 284 | A | 355 | A |
| 242 | A | 300 | A | 356 | A |
| 243 | A | 302 | C | 357 | A |
| 244 | A | 303 | A | 358 | A |
| 245 | A | 312 | A | 365 | A |
| 246 | A | 316 | A | 366 | A |
| 248 | B | 321 | A | 369 | A |
| 250 | B | 324 | A | 370 | B |
| 371 | B | 407 | A | 449 | A |
| 372 | A | 409 | A | 450 | A |
| 373 | A | 420 | A | 451 | A |
| 374 | A | 421 | A | 452 | A |
| 375 | B | 424 | B | 453 | A |
| 383 | C | 425 | A | 454 | A |
| 384 | B | 427 | A | 455 | A |
| 386 | C | 428 | A | 465 | A |
| 388 | A | 429 | A | 466 | A |
| 390 | A | 431 | A | 467 | A |
| 391 | A | 432 | B | 468 | A |
| 392 | A | 433 | A | 469 | A |
| 393 | A | 434 | A | 470 | A |
| 394 | A | 435 | A | 471 | A |
| 395 | A | 436 | A | 472 | A |
| 396 | A | 437 | A | 473 | A |
| 397 | A | 438 | A | 474 | A |
| 398 | A | 439 | A | 475 | A |
| 399 | A | 440 | A | 476 | A |
| 400 | A | 441 | A | 477 | A |
| 401 | A | 442 | A | 478 | A |
| 402 | A | 444 | A | 479 | A |
| 403 | A | 445 | A | 480 | A |
| 404 | A | 446 | A | 481 | A |
| 405 | A | 447 | A | 482 | A |
| 406 | A | 448 | A | 483 | A |
| 484 | A | 524 | B | 564 | A |
| 485 | A | 525 | B | 567 | A |
| 486 | A | 527 | A | 568 | A |
| 487 | A | 531 | A | 569 | A |
| 489 | A | 532 | A | 570 | A |
| 490 | A | 533 | A | 571 | A |
| 491 | A | 534 | A | 572 | A |
| 492 | A | 535 | C | 573 | A |
| 493 | A | 536 | A | 576 | A |
| 494 | A | 537 | A | 577 | A |
| 495 | A | 538 | C | 578 | A |
| 496 | A | 544 | C | 579 | A |
| 497 | A | 545 | A | 580 | B |
| 498 | A | 546 | A | 581 | A |
| 499 | A | 547 | A | 585 | C |
| 500 | C | 548 | A | 586 | B |
| 501 | A | 549 | A | 587 | C |
| 502 | A | 551 | A | 588 | C |
| 503 | A | 552 | C | 589 | B |
| 504 | A | 553 | B | 590 | C |
| 505 | A | 554 | B | 592 | B |
| 506 | A | 555 | C | 593 | C |
| 507 | A | 556 | C | 599 | C |
| 508 | A | 557 | C | 602 | A |
| 517 | C | 562 | A | 603 | A |
| 518 | C | 563 | A | 604 | A |
| 606 | C | 636 | A | 676 | A |
| 607 | C | 638 | A | 677 | A |
| 608 | A | 639 | C | 678 | A |
| 609 | A | 640 | A | 679 | A |
| 610 | A | 641 | A | 680 | A |
| 611 | B | 642 | A | 682 | A |
| 612 | A | 643 | A | 683 | A |
| 613 | B | 648 | B | 684 | A |
| 614 | B | 649 | A | 685 | A |

TABLE 6-continued

| Compound No. | Insecticidal activity | Compound No. | Insecticidal activity | Compound No. | Insecticidal activity |
|---|---|---|---|---|---|
| 615 | B | 650 | A | 686 | B |
| 616 | A | 651 | C | 687 | C |
| 617 | B | 653 | B | 688 | C |
| 618 | A | 657 | A | 691 | C |
| 619 | A | 658 | A | 692 | B |
| 620 | A | 659 | B | 693 | A |
| 621 | A | 660 | A | 694 | A |
| 622 | A | 661 | A | 695 | A |
| 623 | A | 662 | A | 696 | B |
| 624 | A | 663 | A | 698 | C |
| 625 | B | 667 | C | 699 | C |
| 626 | A | 668 | A | 701 | A |
| 627 | A | 670 | A | 702 | A |
| 628 | A | 671 | C | 703 | C |
| 629 | A | 673 | A | 710 | C |
| 630 | A | 674 | A | 713 | A |
| 631 | A | 675 | B | 714 | A |
| 715 | A | 760 | B | 818 | A |
| 716 | A | 761 | B | 819 | A |
| 717 | A | 762 | A | 821 | A |
| 719 | A | 763 | C | 822 | A |
| 720 | A | 764 | A | 823 | A |
| 721 | A | 766 | A | 824 | A |
| 723 | A | 767 | A | 825 | A |
| 724 | A | 768 | A | 826 | A |
| 725 | A | 769 | A | 827 | A |
| 726 | A | 770 | A | 828 | A |
| 727 | A | 772 | A | 829 | A |
| 728 | A | 773 | A | 830 | A |
| 729 | A | 774 | A | 831 | A |
| 731 | A | 775 | A | 832 | B |
| 732 | A | 776 | C | 833 | A |
| 733 | A | 777 | A | 834 | A |
| 734 | A | 780 | C | 835 | A |
| 735 | A | 784 | C | 836 | A |
| 737 | B | 786 | C | 837 | A |
| 740 | A | 795 | A | 838 | A |
| 741 | A | 799 | C | 839 | A |
| 742 | A | 802 | A | 840 | B |
| 746 | A | 805 | C | 841 | A |
| 756 | A | 812 | C | 842 | A |
| 757 | A | 815 | C | 843 | A |
| 759 | B | 817 | A | 844 | A |
| 845 | A | 850 | A | 853 | A |
| 847 | A | 851 | A | 854 | A |
| 848 | B | 852 | A | 855 | A |
| 849 | A | | | | |

TEST EXAMPLE 6

Insecticidal activity against the green peach aphid (*Myzus percicae*)

All stages of the aphids ware inoculated on a chinese cabbage. Insects and the plant were sprayed with the aqueous emulsion of the compound at 200 ppm. On 3rd day after treatment, the insecticidal activity was judged according to the same criterion as in the test example 4. The results are shown in Table 7.

TABLE 7

| Compound No. | Insecticidal activity | Compound No. | Insecticidal activity | Compound No. | Insecticidal activity |
|---|---|---|---|---|---|
| 9 | B | 54 | A | 99 | A |
| 10 | B | 55 | A | 100 | B |
| 12 | C | 56 | A | 101 | A |
| 14 | C | 57 | A | 102 | B |
| 16 | C | 58 | A | 103 | A |
| 18 | A | 59 | A | 104 | A |
| 19 | A | 60 | A | 105 | C |
| 20 | A | 66 | A | 106 | A |
| 21 | A | 67 | A | 107 | C |
| 22 | A | 68 | A | 108 | C |
| 23 | A | 69 | A | 109 | A |
| 24 | B | 71 | A | 110 | A |
| 26 | A | 72 | B | 111 | A |
| 27 | A | 73 | A | 112 | A |
| 33 | A | 74 | A | 113 | A |
| 34 | A | 77 | A | 114 | C |
| 35 | B | 85 | A | 115 | A |
| 36 | A | 86 | B | 116 | A |
| 41 | C | 87 | A | 117 | A |
| 42 | A | 88 | A | 122 | B |
| 45 | A | 89 | A | 123 | C |
| 50 | A | 90 | A | 124 | C |
| 51 | A | 91 | A | 130 | A |
| 52 | A | 92 | A | 131 | A |
| 53 | A | 95 | A | 132 | A |
| 133 | A | 197 | A | 237 | A |
| 134 | A | 198 | A | 238 | B |
| 135 | C | 199 | A | 239 | A |
| 136 | A | 200 | A | 240 | A |
| 138 | C | 201 | A | 241 | C |
| 139 | B | 202 | A | 243 | A |
| 140 | A | 203 | A | 245 | B |
| 141 | A | 204 | A | 246 | A |
| 143 | A | 205 | A | 248 | B |
| 145 | A | 207 | C | 249 | B |
| 153 | A | 211 | A | 250 | C |
| 154 | B | 212 | A | 251 | A |
| 155 | B | 213 | A | 253 | C |
| 156 | B | 215 | A | 254 | A |
| 157 | A | 216 | B | 255 | A |
| 158 | B | 217 | C | 257 | C |
| 159 | C | 220 | A | 258 | A |
| 160 | A | 221 | A | 262 | C |
| 161 | C | 228 | C | 263 | B |
| 163 | A | 229 | A | 264 | A |
| 173 | A | 230 | A | 265 | A |
| 180 | A | 231 | A | 266 | B |
| 193 | A | 232 | A | 267 | A |
| 194 | A | 234 | A | 268 | A |
| 195 | A | 235 | A | 282 | C |
| 196 | A | 236 | A | 296 | A |
| 299 | A | 355 | A | 401 | B |
| 302 | B | 356 | A | 402 | B |
| 306 | A | 357 | A | 403 | A |
| 311 | C | 358 | A | 404 | A |
| 315 | A | 364 | B | 405 | A |
| 316 | B | 365 | A | 406 | C |
| 321 | A | 366 | A | 407 | B |
| 328 | A | 370 | B | 409 | A |
| 329 | A | 371 | B | 421 | A |
| 330 | A | 372 | C | 422 | A |
| 331 | A | 373 | B | 424 | B |
| 332 | B | 374 | B | 427 | A |
| 333 | A | 375 | A | 428 | A |
| 334 | B | 388 | B | 429 | A |
| 337 | A | 389 | A | 431 | A |
| 340 | A | 390 | A | 432 | A |
| 342 | A | 391 | A | 433 | A |
| 343 | A | 392 | A | 434 | A |
| 344 | A | 393 | B | 435 | A |
| 345 | A | 394 | A | 436 | A |
| 346 | A | 395 | A | 437 | A |
| 347 | A | 396 | A | 438 | A |
| 349 | A | 397 | A | 439 | B |
| 350 | A | 398 | B | 440 | A |
| 352 | A | 399 | B | 441 | A |
| 353 | A | 400 | A | 442 | A |
| 443 | A | 479 | A | 507 | A |
| 444 | A | 480 | A | 508 | A |
| 445 | A | 481 | A | 511 | A |
| 446 | A | 482 | A | 512 | A |
| 447 | B | 483 | A | 513 | A |
| 448 | A | 484 | A | 514 | A |
| 449 | A | 485 | A | 515 | A |
| 450 | A | 486 | A | 517 | C |
| 451 | A | 487 | A | 518 | C |
| 452 | A | 488 | A | 527 | A |
| 453 | A | 489 | A | 532 | A |
| 454 | A | 490 | A | 533 | A |
| 455 | B | 491 | A | 534 | A |

TABLE 7-continued

| Compound No. | Insecticidal activity | Compound No. | Insecticidal activity | Compound No. | Insecticidal activity |
|---|---|---|---|---|---|
| 465 | B | 492 | A | 537 | A |
| 466 | A | 493 | A | 538 | A |
| 467 | A | 495 | A | 541 | B |
| 468 | A | 496 | B | 544 | C |
| 469 | B | 497 | A | 545 | A |
| 470 | A | 498 | A | 546 | A |
| 471 | B | 499 | A | 547 | A |
| 472 | B | 501 | A | 548 | A |
| 473 | A | 502 | A | 549 | A |
| 474 | A | 503 | A | 550 | C |
| 476 | A | 504 | A | 551 | C |
| 477 | A | 505 | A | 552 | C |
| 478 | B | 506 | A | 553 | A |
| 554 | A | 595 | A | 630 | A |
| 555 | B | 602 | A | 631 | A |
| 556 | B | 603 | A | 633 | A |
| 557 | C | 604 | B | 634 | B |
| 561 | A | 608 | A | 636 | A |
| 562 | A | 609 | A | 637 | A |
| 563 | B | 610 | A | 638 | B |
| 564 | A | 611 | C | 639 | C |
| 565 | C | 612 | A | 640 | A |
| 566 | A | 613 | A | 642 | B |
| 567 | A | 614 | B | 643 | B |
| 568 | A | 615 | B | 644 | C |
| 569 | A | 616 | C | 645 | A |
| 570 | A | 617 | A | 646 | A |
| 571 | A | 618 | B | 652 | A |
| 572 | B | 619 | A | 654 | B |
| 573 | C | 620 | A | 656 | A |
| 574 | A | 621 | B | 657 | A |
| 576 | B | 622 | B | 658 | A |
| 577 | A | 623 | C | 660 | A |
| 578 | C | 624 | A | 661 | A |
| 580 | C | 625 | A | 662 | B |
| 584 | C | 626 | A | 663 | A |
| 585 | A | 627 | A | 664 | C |
| 586 | C | 628 | A | 665 | C |
| 588 | C | 629 | A | 667 | B |
| 668 | A | 697 | A | 737 | A |
| 669 | A | 698 | C | 741 | C |
| 670 | A | 699 | A | 742 | C |
| 671 | A | 701 | A | 743 | C |
| 673 | B | 702 | A | 746 | C |
| 674 | A | 703 | C | 751 | C |
| 675 | B | 710 | C | 752 | C |
| 676 | B | 713 | A | 757 | B |
| 677 | A | 715 | A | 758 | A |
| 678 | A | 716 | A | 759 | A |
| 679 | A | 717 | C | 762 | A |
| 680 | A | 719 | A | 763 | C |
| 681 | C | 720 | C | 764 | C |
| 682 | A | 723 | B | 766 | A |
| 683 | A | 724 | A | 767 | A |
| 684 | B | 725 | A | 768 | A |
| 685 | C | 726 | A | 769 | A |
| 686 | A | 727 | A | 770 | A |
| 687 | B | 728 | A | 772 | A |
| 689 | B | 729 | A | 774 | A |
| 691 | B | 730 | A | 775 | B |
| 692 | A | 731 | A | 776 | B |
| 693 | A | 732 | A | 777 | B |
| 694 | A | 733 | A | 779 | A |
| 695 | A | 734 | A | 798 | A |
| 696 | A | 735 | A | 799 | A |
| 801 | C | 824 | B | 840 | C |
| 804 | C | 825 | B | 841 | A |
| 805 | C | 826 | B | 842 | A |
| 812 | A | 827 | A | 843 | A |
| 813 | B | 828 | A | 844 | A |
| 814 | B | 829 | A | 848 | C |
| 815 | B | 831 | A | 849 | A |
| 816 | C | 832 | A | 850 | B |
| 817 | C | 833 | A | 851 | A |
| 818 | C | 834 | A | 852 | A |
| 819 | C | 835 | A | 853 | A |
| 821 | A | 836 | A | 854 | A |
| 822 | A | 837 | A | 855 | B |
| 823 | A | 839 | A | | |

TEST EXAMPLE 7

Acaricidal acitivity against the citrus red mite (*Panonychus citri*)

Female adults were inoculated on a grapefruit leaf, and were sprayed with the aqueous emulsion of the compound at 200 ppm. On 10th day after treatment, the number of the progeny survived was counted and acaricidal activity was judged according to the same criterion as in the test example 4.

The results are shown in Table 8.

TABLE 8

| Compound No. | Acaricidal activity |
|---|---|
| 8 | A |
| 9 | A |
| 10 | A |
| 11 | A |
| 12 | A |
| 13 | B |
| 24 | A |
| 25 | B |
| 27 | A |
| 32 | A |
| 33 | A |
| 34 | A |
| 35 | A |
| 41 | A |
| 42 | A |
| 50 | A |
| 51 | A |
| 53 | C |
| 54 | A |
| 55 | A |
| 56 | A |
| 57 | A |
| 65 | A |
| 68 | A |
| 69 | A |
| 71 | A |
| 74 | A |
| 86 | A |
| 87 | A |
| 88 | A |
| 89 | A |
| 90 | A |
| 91 | A |
| 92 | A |
| 94 | B |
| 95 | A |
| 96 | A |
| 97 | A |
| 98 | A |
| 102 | A |
| 103 | A |
| 105 | A |
| 109 | A |
| 112 | A |
| 113 | A |
| 114 | A |
| 118 | A |
| 119 | B |
| 120 | B |
| 121 | A |
| 122 | A |
| 124 | A |
| 125 | A |
| 126 | A |
| 133 | A |
| 134 | A |
| 135 | A |

TABLE 8-continued

| Compound No. | Acaricidal activity |
|---|---|
| 136 | A |
| 140 | B |
| 147 | B |
| 150 | C |
| 152 | A |
| 153 | A |
| 154 | A |
| 155 | A |
| 156 | A |
| 157 | A |
| 158 | A |
| 159 | A |
| 160 | A |
| 161 | C |
| 164 | A |
| 166 | A |
| 167 | B |
| 169 | A |
| 170 | A |
| 171 | A |
| 193 | A |
| 194 | A |
| 195 | B |
| 196 | C |
| 197 | A |
| 198 | A |
| 199 | A |
| 200 | A |
| 201 | A |
| 202 | A |
| 206 | A |
| 207 | C |
| 211 | A |
| 212 | A |
| 214 | A |
| 217 | A |
| 218 | A |
| 219 | A |
| 220 | A |
| 221 | C |
| 227 | A |
| 230 | A |
| 232 | A |
| 233 | B |
| 235 | A |
| 237 | A |
| 238 | A |
| 239 | A |
| 240 | A |
| 241 | A |
| 242 | A |
| 243 | A |
| 245 | A |
| 246 | A |
| 248 | A |
| 251 | B |
| 252 | A |
| 253 | A |
| 254 | A |
| 255 | B |
| 256 | A |
| 257 | A |
| 258 | A |
| 262 | A |
| 263 | A |
| 264 | A |
| 265 | A |
| 266 | A |
| 267 | A |
| 268 | A |
| 269 | A |
| 282 | A |
| 283 | A |
| 284 | C |
| 300 | C |
| 329 | B |
| 330 | B |
| 333 | A |
| 334 | A |
| 335 | A |

TABLE 8-continued

| Compound No. | Acaricidal activity |
|---|---|
| 337 | A |
| 342 | A |
| 343 | A |
| 344 | A |
| 347 | A |
| 349 | A |
| 350 | A |
| 351 | A |
| 353 | A |
| 354 | A |
| 355 | A |
| 356 | A |
| 357 | A |
| 358 | A |
| 363 | A |
| 364 | A |
| 365 | A |
| 366 | A |
| 367 | A |
| 369 | A |
| 370 | A |
| 371 | A |
| 373 | A |
| 374 | A |
| 375 | B |
| 376 | B |
| 377 | B |
| 381 | A |
| 385 | A |
| 387 | A |
| 388 | A |
| 389 | A |
| 390 | A |
| 391 | A |
| 392 | A |
| 393 | A |
| 394 | A |
| 397 | C |
| 399 | A |
| 400 | B |
| 401 | A |
| 402 | A |
| 403 | A |
| 404 | A |
| 406 | B |
| 407 | C |
| 408 | C |
| 409 | A |
| 410 | C |
| 421 | A |
| 422 | A |
| 431 | A |
| 432 | A |
| 433 | A |
| 434 | B |
| 437 | A |
| 439 | C |
| 442 | A |
| 443 | A |
| 444 | A |
| 447 | A |
| 448 | A |
| 449 | A |
| 450 | A |
| 451 | A |
| 452 | A |
| 453 | A |
| 455 | A |
| 465 | A |
| 466 | A |
| 467 | C |
| 468 | A |
| 469 | A |
| 470 | A |
| 471 | A |
| 472 | A |
| 473 | A |
| 476 | A |
| 477 | A |
| 478 | C |

TABLE 8-continued

| Compound No. | Acaricidal activity |
|---|---|
| 479 | A |
| 480 | A |
| 481 | A |
| 482 | A |
| 483 | A |
| 484 | A |
| 485 | A |
| 486 | A |
| 487 | A |
| 488 | A |
| 489 | A |
| 516 | A |
| 517 | A |
| 518 | A |
| 523 | A |
| 524 | A |
| 525 | A |
| 527 | A |
| 529 | A |
| 532 | A |
| 533 | A |
| 534 | A |
| 535 | B |
| 537 | A |
| 538 | A |
| 541 | B |
| 543 | C |
| 544 | A |
| 545 | A |
| 546 | A |
| 547 | B |
| 548 | A |
| 549 | A |
| 552 | A |
| 553 | A |
| 554 | A |
| 555 | A |
| 556 | A |
| 557 | A |
| 562 | A |
| 563 | A |
| 564 | A |
| 565 | A |
| 566 | A |
| 567 | A |
| 568 | A |
| 569 | A |
| 570 | A |
| 571 | A |
| 572 | A |
| 573 | B |
| 574 | A |
| 575 | A |
| 576 | A |
| 577 | A |
| 578 | A |
| 579 | B |
| 580 | A |
| 584 | A |
| 585 | A |
| 586 | A |
| 587 | A |
| 588 | A |
| 589 | C |
| 592 | C |
| 594 | A |
| 595 | A |
| 596 | B |
| 597 | A |
| 598 | B |
| 599 | B |
| 602 | B |
| 603 | C |
| 604 | A |
| 605 | B |
| 606 | A |
| 607 | A |
| 608 | A |
| 609 | A |
| 610 | A |
| 611 | A |
| 612 | A |
| 613 | A |
| 614 | A |
| 615 | A |
| 616 | A |
| 617 | A |
| 618 | A |
| 619 | B |
| 620 | A |
| 621 | A |
| 623 | A |
| 624 | A |
| 625 | A |
| 626 | A |
| 627 | A |
| 628 | A |
| 629 | A |
| 630 | A |
| 631 | A |
| 636 | A |
| 637 | A |
| 638 | A |
| 639 | A |
| 640 | A |
| 641 | A |
| 642 | A |
| 643 | A |
| 644 | B |
| 645 | A |
| 646 | A |
| 647 | A |
| 648 | A |
| 649 | A |
| 650 | B |
| 651 | A |
| 652 | A |
| 653 | A |
| 654 | B |
| 655 | B |
| 656 | B |
| 657 | C |
| 658 | A |
| 659 | A |
| 660 | A |
| 661 | A |
| 662 | A |
| 663 | A |
| 664 | A |
| 665 | A |
| 666 | A |
| 667 | A |
| 668 | A |
| 669 | A |
| 670 | A |
| 671 | A |
| 672 | A |
| 673 | A |
| 674 | A |
| 675 | A |
| 677 | A |
| 678 | A |
| 680 | A |
| 681 | A |
| 682 | A |
| 683 | A |
| 684 | A |
| 685 | B |
| 686 | B |
| 688 | C |
| 690 | A |
| 691 | A |
| 692 | A |
| 693 | A |
| 694 | A |
| 695 | A |
| 696 | A |
| 697 | A |
| 698 | A |
| 699 | A |

TABLE 8-continued

| Compound No. | Acaricidal activity |
|---|---|
| 700 | A |
| 701 | A |
| 702 | C |
| 703 | A |
| 705 | A |
| 710 | A |
| 711 | C |
| 712 | A |
| 713 | A |
| 714 | A |
| 715 | A |
| 716 | A |
| 717 | A |
| 719 | A |
| 720 | A |
| 725 | A |
| 726 | A |
| 727 | C |
| 728 | A |
| 729 | A |
| 730 | A |
| 731 | A |
| 732 | A |
| 733 | A |
| 734 | A |
| 735 | A |
| 737 | A |
| 739 | A |
| 740 | A |
| 741 | A |
| 742 | A |
| 743 | A |
| 744 | A |
| 745 | A |
| 746 | A |
| 749 | A |
| 750 | C |
| 751 | A |
| 754 | A |
| 755 | A |
| 756 | A |
| 757 | A |
| 758 | B |
| 759 | A |
| 760 | A |
| 761 | A |
| 763 | B |
| 764 | C |
| 766 | A |
| 767 | A |
| 768 | A |
| 769 | A |
| 772 | B |
| 773 | C |
| 774 | A |
| 775 | A |
| 777 | A |
| 778 | B |
| 795 | A |
| 800 | A |
| 801 | B |
| 802 | A |
| 812 | A |
| 813 | A |
| 815 | A |
| 816 | A |
| 817 | A |
| 818 | A |
| 819 | A |
| 821 | A |
| 822 | A |
| 823 | A |
| 824 | B |
| 825 | A |
| 826 | A |
| 827 | A |
| 828 | A |
| 829 | A |
| 830 | A |
| 831 | B |
| 832 | B |
| 834 | C |
| 835 | A |
| 836 | A |
| 839 | B |
| 840 | C |
| 842 | A |
| 843 | B |
| 845 | A |
| 848 | A |
| 850 | A |
| 851 | A |
| 852 | A |
| 853 | A |
| 854 | B |
| 856 | B |
| 857 | B |

TEST EXAMPLE 8

Acaricidal activity against the twospotted spidermite (*Tetranychus urticae*)

All stages of the mites were inoculated on a soybean plant. The mites and the plant were sprayed with the aqueous emulsion of the compound at 200 ppm. On 8th day after treatment, the acaricidal activity was judged according to the same criterion as in the test example 4. The results are shown in table 9.

TABLE 9

| Compound No. | Acaricidal activity |
|---|---|
| 8 | A |
| 9 | A |
| 10 | A |
| 11 | A |
| 12 | A |
| 13 | A |
| 17 | C |
| 19 | A |
| 20 | A |
| 21 | A |
| 22 | A |
| 23 | A |
| 24 | A |
| 25 | A |
| 32 | A |
| 33 | B |
| 34 | A |
| 35 | A |
| 36 | A |
| 40 | A |
| 41 | A |
| 42 | B |
| 50 | A |
| 51 | B |
| 52 | A |
| 53 | A |
| 54 | A |
| 55 | A |
| 56 | A |
| 57 | A |
| 58 | A |
| 59 | A |
| 60 | A |
| 65 | B |
| 66 | A |
| 67 | A |
| 68 | A |
| 69 | A |
| 71 | A |
| 72 | A |
| 73 | A |
| 74 | A |
| 85 | A |

TABLE 9-continued

| Compound No. | Acaricidal activity |
|---|---|
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 102 | A |
| 103 | A |
| 104 | A |
| 105 | A |
| 109 | A |
| 110 | A |
| 111 | A |
| 112 | A |
| 113 | A |
| 114 | A |
| 118 | A |
| 119 | A |
| 120 | A |
| 121 | A |
| 122 | A |
| 123 | A |
| 124 | A |
| 125 | A |
| 126 | A |
| 127 | A |
| 133 | A |
| 134 | A |
| 135 | A |
| 136 | A |
| 138 | A |
| 139 | A |
| 140 | A |
| 141 | A |
| 142 | C |
| 143 | A |
| 144 | C |
| 145 | A |
| 146 | A |
| 147 | A |
| 149 | C |
| 150 | C |
| 151 | C |
| 152 | B |
| 153 | A |
| 154 | A |
| 155 | A |
| 156 | A |
| 157 | A |
| 158 | A |
| 159 | A |
| 160 | A |
| 161 | C |
| 164 | A |
| 166 | A |
| 167 | A |
| 169 | A |
| 170 | A |
| 171 | A |
| 193 | A |
| 194 | A |
| 195 | A |
| 197 | B |
| 198 | A |
| 199 | A |
| 200 | A |
| 201 | A |
| 202 | A |
| 203 | A |
| 204 | A |
| 205 | A |
| 206 | A |
| 207 | A |
| 211 | A |
| 212 | A |
| 213 | B |
| 214 | A |
| 215 | A |
| 217 | A |
| 219 | A |
| 220 | A |
| 221 | A |
| 228 | A |
| 229 | A |
| 230 | A |
| 231 | A |
| 232 | B |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 248 | A |
| 249 | A |
| 250 | A |
| 251 | A |
| 253 | A |
| 254 | A |
| 255 | A |
| 256 | A |
| 257 | A |
| 258 | A |
| 262 | A |
| 263 | A |
| 264 | A |
| 265 | A |
| 266 | A |
| 267 | A |
| 268 | A |
| 269 | A |
| 281 | B |
| 282 | A |
| 283 | A |
| 302 | B |
| 304 | C |
| 328 | C |
| 331 | C |
| 332 | C |
| 333 | A |
| 334 | A |
| 335 | B |
| 337 | C |
| 342 | B |
| 343 | C |
| 344 | B |
| 350 | C |
| 353 | A |
| 354 | A |
| 355 | A |
| 356 | A |
| 357 | A |
| 358 | B |
| 363 | A |
| 364 | A |
| 365 | A |
| 366 | A |
| 367 | B |
| 369 | A |
| 370 | B |
| 371 | A |
| 372 | A |
| 373 | A |
| 374 | A |
| 375 | A |

TABLE 9-continued

| Compound No. | Acaricidal activity |
|---|---|
| 376 | B |
| 377 | C |
| 378 | C |
| 379 | C |
| 382 | A |
| 383 | A |
| 384 | A |
| 385 | B |
| 386 | A |
| 387 | A |
| 388 | A |
| 389 | A |
| 390 | A |
| 391 | A |
| 392 | A |
| 393 | A |
| 394 | A |
| 395 | A |
| 396 | B |
| 397 | B |
| 399 | A |
| 400 | A |
| 401 | A |
| 402 | A |
| 403 | A |
| 404 | A |
| 405 | A |
| 406 | A |
| 407 | A |
| 409 | A |
| 421 | A |
| 422 | A |
| 424 | B |
| 427 | B |
| 428 | B |
| 431 | B |
| 432 | B |
| 433 | C |
| 434 | C |
| 436 | A |
| 437 | C |
| 438 | A |
| 439 | A |
| 440 | B |
| 441 | A |
| 443 | A |
| 444 | A |
| 445 | A |
| 446 | A |
| 447 | C |
| 448 | A |
| 449 | A |
| 450 | A |
| 451 | A |
| 452 | A |
| 453 | A |
| 454 | A |
| 455 | A |
| 465 | A |
| 466 | A |
| 467 | A |
| 468 | A |
| 469 | A |
| 470 | A |
| 471 | A |
| 472 | A |
| 473 | A |
| 474 | A |
| 476 | A |
| 477 | A |
| 478 | C |
| 479 | A |
| 480 | A |
| 481 | A |
| 482 | A |
| 483 | A |
| 484 | A |
| 485 | A |
| 486 | A |
| 487 | A |
| 488 | A |
| 489 | A |
| 490 | A |
| 491 | A |
| 492 | A |
| 493 | A |
| 494 | A |
| 495 | A |
| 496 | A |
| 497 | A |
| 498 | A |
| 499 | A |
| 500 | A |
| 501 | A |
| 502 | A |
| 503 | A |
| 504 | A |
| 505 | A |
| 506 | A |
| 507 | A |
| 508 | C |
| 516 | C |
| 517 | A |
| 518 | A |
| 523 | A |
| 524 | A |
| 525 | A |
| 527 | A |
| 531 | A |
| 532 | A |
| 533 | A |
| 534 | A |
| 535 | A |
| 536 | A |
| 537 | A |
| 538 | A |
| 541 | A |
| 544 | A |
| 545 | A |
| 546 | A |
| 547 | A |
| 548 | A |
| 549 | A |
| 550 | B |
| 551 | A |
| 552 | A |
| 553 | A |
| 554 | A |
| 555 | A |
| 556 | A |
| 557 | A |
| 558 | A |
| 559 | B |
| 561 | A |
| 562 | A |
| 563 | A |
| 564 | A |
| 565 | B |
| 566 | B |
| 567 | A |
| 568 | A |
| 569 | A |
| 570 | A |
| 571 | A |
| 572 | A |
| 573 | A |
| 574 | A |
| 575 | B |
| 576 | A |
| 577 | A |
| 578 | A |
| 579 | A |
| 580 | A |
| 584 | A |
| 585 | A |
| 587 | A |
| 588 | A |
| 594 | A |
| 595 | A |
| 596 | C |

TABLE 9-continued

| Compound No. | Acaricidal activity |
|---|---|
| 597 | B |
| 599 | B |
| 600 | B |
| 602 | A |
| 603 | A |
| 604 | A |
| 605 | A |
| 606 | A |
| 607 | B |
| 608 | A |
| 609 | A |
| 610 | A |
| 611 | A |
| 612 | A |
| 613 | A |
| 614 | A |
| 615 | A |
| 616 | A |
| 617 | A |
| 618 | A |
| 619 | A |
| 620 | A |
| 621 | A |
| 623 | A |
| 624 | A |
| 625 | A |
| 626 | A |
| 627 | A |
| 628 | A |
| 629 | A |
| 630 | A |
| 631 | A |
| 636 | A |
| 637 | A |
| 638 | A |
| 639 | A |
| 640 | A |
| 642 | A |
| 643 | A |
| 644 | C |
| 645 | A |
| 646 | A |
| 647 | A |
| 648 | A |
| 650 | C |
| 652 | A |
| 653 | B |
| 654 | A |
| 655 | A |
| 656 | A |
| 657 | A |
| 658 | A |
| 659 | A |
| 660 | A |
| 661 | A |
| 662 | A |
| 663 | A |
| 664 | A |
| 665 | A |
| 666 | A |
| 667 | A |
| 668 | A |
| 669 | A |
| 670 | A |
| 671 | A |
| 672 | A |
| 673 | A |
| 674 | A |
| 675 | A |
| 677 | A |
| 678 | A |
| 680 | A |
| 681 | A |
| 682 | A |
| 683 | A |
| 684 | A |
| 691 | A |
| 692 | A |
| 694 | A |
| 695 | C |
| 696 | A |
| 697 | A |
| 699 | A |
| 701 | A |
| 702 | A |
| 703 | A |
| 704 | B |
| 705 | A |
| 706 | A |
| 709 | A |
| 710 | A |
| 712 | A |
| 713 | A |
| 714 | B |
| 715 | A |
| 716 | A |
| 717 | A |
| 718 | C |
| 719 | A |
| 720 | A |
| 721 | A |
| 723 | A |
| 724 | A |
| 725 | A |
| 726 | A |
| 727 | A |
| 728 | A |
| 729 | A |
| 730 | A |
| 731 | A |
| 732 | A |
| 733 | A |
| 734 | A |
| 735 | B |
| 736 | C |
| 737 | A |
| 739 | A |
| 740 | A |
| 741 | A |
| 742 | A |
| 743 | A |
| 745 | B |
| 746 | A |
| 751 | A |
| 752 | A |
| 753 | A |
| 754 | B |
| 756 | B |
| 757 | A |
| 758 | A |
| 759 | A |
| 760 | A |
| 761 | A |
| 762 | B |
| 763 | A |
| 764 | B |
| 765 | C |
| 766 | A |
| 767 | A |
| 768 | A |
| 769 | A |
| 770 | A |
| 771 | A |
| 772 | A |
| 773 | A |
| 774 | A |
| 775 | A |
| 776 | A |
| 777 | A |
| 778 | A |
| 779 | A |
| 780 | A |
| 782 | A |
| 785 | B |
| 789 | C |
| 791 | C |
| 792 | B |
| 799 | B |
| 800 | B |
| 801 | B |

TABLE 9-continued

| Compound No. | Acaricidal activity |
|---|---|
| 804 | A |
| 811 | C |
| 816 | A |
| 817 | A |
| 818 | A |
| 819 | A |
| 821 | A |
| 822 | A |
| 823 | A |
| 824 | A |
| 825 | B |
| 826 | A |
| 827 | A |
| 828 | A |
| 829 | A |
| 830 | A |
| 831 | A |
| 832 | A |
| 833 | A |
| 834 | A |
| 835 | A |
| 836 | A |
| 837 | A |
| 838 | B |
| 839 | A |
| 840 | A |
| 842 | A |
| 843 | A |
| 844 | A |
| 845 | C |
| 848 | A |
| 850 | A |
| 851 | A |
| 852 | A |
| 853 | A |
| 854 | A |
| 855 | A |

Next, formulation examples will be shown. In the examples, all parts are by weight.

FORMULATION EXAMPLE 1

Wettable powder

| | |
|---|---|
| Compound No. 60 | 50 parts |
| Mixture of diatomaceous earth and clay | 45 parts |
| Polyoxyethylene nonylphenyl ether | 5 parts |

The above materials were uniformly mixed and ground to obtain a wettable powder.

FORMULATION EXAMPLE 2

Emulsion

| | |
|---|---|
| Compound No. 154 | 20 parts |
| Tetrahydrofuran | 20 parts |
| Xylene | 45 parts |
| Mixture of polyoxyethylene nonylphenyl ether and a salt of alkylbenzenesulfonic acid | 15 parts |

The above materials were uniformly mixed and dissolved to obtain an emulsion.

FORMULATION EXAMPLE 3

Dust

| | |
|---|---|
| Compound No. 503 | 4 parts |
| Mixture of diatomaceous earth, clay and talc | 95 parts |
| Calcium stearate | 1 part |

The above materials were univormly mixed and ground to obtain a dust.

FORMULATION EXAMPLE 4

Granule

| | |
|---|---|
| Compound No. 237 | 3 parts |
| Mixture of bentonite and clay | 92 parts |
| Calcium ligninsulfonate | 5 parts |

The above materials were uniformly mixed and ground. The resulting ground mixture were thoroughly kneaded with a proper amount of water and pelletized to obtain granules.

What is claimed is:

1. A pyrazole oxime derivative represented by the general formula (I),

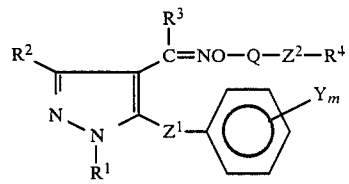

wherein $R^1$ represents $C_1$-$C_4$ alkyl or phenyl; $R^2$ represents hydrogen, $C_1$-$C_5$ alkyl, $C_1$-$C_3$ haloalkyl or phenyl; $R^3$ represents hydrogen, $C_1$-$C_4$ alkyl or phenyl; $R^4$ represents hydrogen, $C_2$-$C_4$ alkylcarbonyl, benzoyl, naphthyl or a substituent of the formula,

[in which X represents hydrogen; halogen; $C_1$-$C_{12}$ alkyl; $C_1$-$C_6$ alkyl substituted with halogen, cyano, hydroxy, $C_1$-$C_5$ alkoxy or $C_2$-$C_6$ alkoxycarbonyl; $C_3$-$C_8$ cycloalkyl; cycloalkyl substituted with from one to three members selected from the group consisting of $C_1$-$C_4$ alkyl, halogen and cyano; $C_2$-$C_4$ alkenyl substituted with halogen, hydroxy, $C_2$-$C_4$ alkoxycarbonyl or $C_2$-$C_6$ alkylcarbonyl; phenyl; hydroxy; $C_1$-$C_6$ alkoxy; $C_1$-$C_4$ alkoxy substituted with halogen or $C_2$-$C_6$ alkoxycarbonyl; phenoxy which may or may not be sustituted with $C_1$-$C_3$ haloalkyl; benzyloxy; $C_1$-$C_3$ alklenedioxy formed by two adjacent Xs; pyridyloxy which may or may not be substituted with halogen of $C_1$-$C_3$ haloalkyl; a substituent of the formula, —S(O)$_p$R$^5$ (in which $R^5$ represents $C_1$-$C_6$ alkyl, $C_1$-$C_5$ haloalkyl or phenyl, and p represents an integer of 0, 1 or 2); cyano; formyl; nitro; a substituent of the formula, —COOR$^6$ {in which $R^6$ represents hydrogen; alkali metal; $C_1$-$C_{10}$ alkyl; $C_1$-$C_5$ alkyl substituted with halogen, $C_1$-$C_4$ alkoxy, phenoxy, $C_2$-$C_4$ alkoxycarbonyl or phenoxyphenyl; $C_2$-$C_7$ alkenyl; $C_3$-$C_7$ alkynyl; $C_3$-$C_8$ cycloalkyl; $C_3$-$C_8$ cycloalkyl substituted with $C_1$-$C_3$ alkyl; phenyl; or a substituent of the formula,

(in which $R^7$, $R^8$ and $R^9$, which may be the same or different, represent $C_1$-$C_4$ alkyl or $C_3$-$C_8$ cycloalkyl)}; $C_2$-$C_6$ alkylcarbonyl; $C_2$-$C_6$ alkylcarbonyl substituted with cyano or $C_2$-$C_6$ alkoxycarbonyl; benzoyl which may or may not be substituted with halogen or $C_1$-$C_6$ alkyl; $C_2$-$C_6$ alkylthiocarbonyl; $C_3$-$C_7$ alkoxycarbonylcarbonyl; a substituent of the formula,

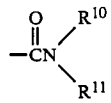

(in which $R^{10}$ and $R^{11}$, which may be the same or different, represent hydrogen, $C_1$-$C_6$ alkyl or phenyl); piperidinocarbonyl; morpholinocarbonyl which may be or may not be substituted with one or two $C_1$-$C_4$ alkyls; a substituent of the formula,

(in which $R^{12}$ represents hydrogen or $C_1$-$C_5$ alkyl, and $R^{13}$ represents formyl, $C_2$-$C_{12}$ alkoxycarbonyl, or $C_2$-$C_5$ alkoxycarbonyl substituted with halogen or $C_1$-$C_4$ alkoxy); a substituent of the formula,

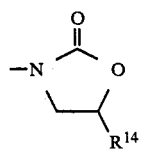

(in which $R^{14}$ represents hydrogen, $C_{1-C_4}$ alkyl or $C_2$-$C_6$ alkoxyalkyl); a substituent of the formula,

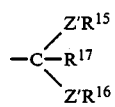

(in which $R^{15}$ and $R^{16}$, which may be the same or different, represent $C_1$-$C_4$ alkyl or, taken together, may form $C_1$-$C_4$ alkylene, $R^{17}$ represents $C_1$-$C_5$ alkyl, cyano or $C_2$-$C_6$ alkoxycarbonyl, and $Z^1$ represents oxygen or sulfur); a substituent of the formula,

(in which $R^{18}$ represents hydrogen or $C_2$-$C_4$ alkycarbonyl, and $R^{19}$ and $R^{20}$, which may be the same or different, represent hydrogen or $C_1$-$C_6$ alkyl); a substituent of the formula,

(in which $R^{21}$, $R^{22}$ and $R^{23}$, which may be the same or different, represent $C_1$-$C_4$ alkyl); or a substituent of the formula,

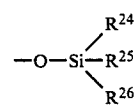

(in which $R^{24}$, $R^{25}$ and $R^{26}$, which may be the same or different, represent $C_1$-$C_4$ alkyl), and n represents an integer of from 1 to 5, and when n represents an integer of from 2 to 5, X may be the same or different]; Y represents hydrogen, $C_1$-$C_6$ alkyl, $C_1$-$C_4$ haloalkyl, halogen, hydroxy, $C_1$-$C_4$ alkoxy, $C_1$-$C_4$ haloalkoxy, $C_1$-$C_3$ alkylenedioxy, phenoxy which may or may not be substituted with trifluoromethyl, a substituent of the formula, —$S(O)_qR^{27}$ (in which $R^{27}$ represents $C_1$-$C_3$ alkyl and q represents an integer of 0, 1 or 2), hydroxycarbonyl, $C_2$-$C_5$ alkoxycarbonyl or a substituent of the formula,

(in which $R^{28}$ and $R^{29}$, which may be the same or different, represent hydrogen, $C_1$-$C_4$ alkyl, or benzyl which may or may not be substituted with $C_2$-$C_6$ alkoxycarbonyl); $Z^1$ represents oxygen or sulfur; $Z^2$ represents oxygen, sulfur or single bond; Q represents $C_1$-$C_8$ alkylene, $C_1$-$C_8$ alkylene substituted with halogen or phenyl, $C_3$-$C_{12}$ alkenylene, $C_3$-$C_{12}$ haloalkenylene or $C_3$-$C_6$ alkynylene; and m represents an integer of from 1 to 3, and when m represents an integer of 2 or 3, Y may be the same or different.

2. A pyrazole oxime derivative according to claim 1, wherein $R^1$ represents $C_1$-$C_4$ alkyl; $R^2$ represents $C_1$-$C_4$ alkyl or $C_1$-$C_3$ haloalkyl; $R^3$ represents hydrogen, $C_1$-$C_4$ alkyl or phenyl; $R^4$ represents a substituent of the formula,

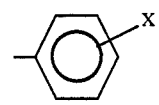

[in which X represents $C_1$-$C_{12}$ alkyl; $C_1$-$C_4$ haloalkyl; $C_3$-$C_7$ cycloalkyl; $C_3$-$C_7$ cycloalkyl substituted with from one to three members selected from the group consisting of $C_1$-$C_4$ alkyl, halogen and cyano; $C_1$-$C_5$ alkoxy; $C_1$-$C_4$ haloalkoxy; 3-chloro-5-trifluoromethyl-pyridin-2-yloxy; a substituent of the formula, —S-$(O)_pR^5$ (in which $R^5$ represents $C_1$-$C_5$ alkyl, $C_1$-$C_5$ haloalkyl or phenyl, and p represents an integer of 0, 1 or 2); a substituent of the formula, —$COOR^6$ (in which $R^6$ represents $C_1$-$C_8$ alkyl, $C_1$-$C_6$ haloalkyl, $C_5$-$C_7$ cycloalkyl; or $C_3$-$C_8$ cycloalkyl substituted with $C_1$-$C_3$ alkyl); $C_2$-$C_6$ alkylcarbonyl; $C_2$-$C_6$ alkylthiocarbonyl;

$C_3$–$C_9$ N,N-dialkylcarbonyl; a substituent of the formula,

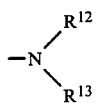

(in which $R^{12}$ represents $C_1$–$C_5$ alkyl, and $R^{13}$ represents $C_2$–$C_{10}$ alkoxycarbonyl or formyl); a substituent of the formula,

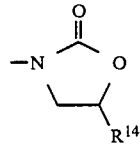

(in which $R^{14}$ represents hydrogen, $C_1$–$C_4$ alkyl or $C_2$–$C_5$ alkoxyalkyl); a substituent of the formula,

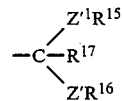

(in which $R^{15}$ and $R^{16}$, taken together, form $C_1$–$C_7$ alkylene, $R^{17}$ represents $C_1$–$C_4$ alkyl and $Z^1$ represents oxygen or sulfur); or trimethylsilyl]; Y represents hydrogen, $C_1$–$C_6$ alkyl, halogen, $C_1$–$C_4$ alkoxy or $C_1$–$C_4$ haloalkoxy; and Q represents $C_1$–$C_4$ alkylene which may have a branched chain.

3. A pyrazole oxime derivative according to claim 1, wherein $R^1$ represents methyl; $R^2$ represents methyl or trifluoromethyl; $R^3$ represents hydrogen or methyl; $R^4$ represents a substituent of the formula,

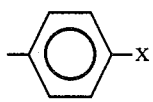

[in which X represents tert-butyl, 2,2-dichloro-1-methlcyclopropyl, 1-cyanocyclopentyl, cyclohexyl, tert-butoxy, 1,1,2,2-tetrafluoroethoxy, 3-chloro-5-trifluoromethylpyridin-2-yloxy, $C_1$–$C_4$ alkylthio, heptafluoropropylthio, $C_1$–$C_3$ haloalkylsulfinyl, tert-butylcarbonyl, tert-butylthiocarbonyl, $C_3$–$C_7$ N,N-dialkylcarbamoyl, 2-methyl-1,3-dioxolane-2-yl, 2,4-dimethyl-1,3-dioxolane-2-yl, 2-isopropyl-1,3-dioxolane-2-yl, 2-isopropyl-1,3-dithiolane-2-yl, a substituent of the formula, —COOR$^6$ (in which $R^6$ represents $C_3$–$C_5$ alkyl, 1,1-dimethyl-2-chloroethyl, cyclohexyl or 1-methylcyclohexyl), a substituent of the formula,

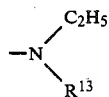

(in which $R^{13}$ represents $C_2$–$C_9$ alkoxycarbonyl or 2-chloroethoxycarbonyl), 5-ethyl-1,3-oxazolidone-2-yl or trimethylsilyl]; Y represents hydrogen or fluorine; $Z^1$ represents oxygen; $Z^2$ represents oxygen or single bond; and Q represents $C_1$–$C_3$ alkylene which may have a branched chain.

4. A pyrazoline oxime derivative according to claim 1, wherein $R^1$ represents methyl; $R^2$ represents methyl or trifluoromethyl; $R^3$ represents hydrogen; $R^4$ represents a substituent of the formula,

[in which X represents tert-butyl, 2,2-dichloro-1-methylcyclopropyl, 1-cyanocyclopentyl, tert-butoxy, 1,1,2,2-tetrafluoroethoxy, heptafluoropropylthio, $C_1$–$C_3$ haloalkylsulfinyl, tert-butylcarbonyl, $C_3$–$C_7$ N,N-dialkylcarbamoyl, 2-isopropyl-1,3-dioxolane-2-yl, 2-isopropyl-1,3-dithiolane-2-yl, a substituent of the formula, —COOR$^6$ (in which $R^6$ represents $C_3$–$C_5$ alkyl, 1,1-dimethyl-2-chloroethyl, cyclohexyl or 1-methylcyclohexyl), a substituent of the formula,

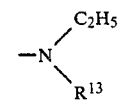

(in which $R^{13}$ represents $C_2$–$C_5$ alkoxycarbonyl) or 5-ethyl-1,3-oxazolidone-2-yl]; Y represents hydrogen or fluorine; $Z^1$ represents oxygen; $Z^2$ represents oxygen or single bond; Q represents $C_1$–$C_2$ alkylene which may have a brached chain; and m represents an integer of 1.

5. An insecticidal and acaricidal composition for use in agriculture and horticulture comprising an insecticidally and/or acaricidally effective amount of a pyrazole oxime derivative as an active ingredient and a suitable carrier, said pyrazole, oxime derivative being represented by the general formula (I),

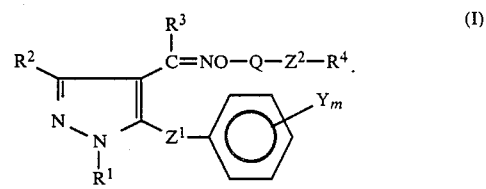

wherein $R^1$ represents $C_1$–$C_4$ alkyl or phenyl; $R^2$ represents hydrogen, $C_1$–$C_5$ alkyl, $C_1$–$C_3$ haloalkyl or phenyl; $R^3$ represents hydrogen, $C_1$–$C_4$ alkyl or phenyl; $R^4$ represents hydrogen, $C_2$–$C_4$ alkylcarbonyl, benzoyl, naphthyl or a substituent of the formula,

[in which X represents hydrogen; halogen; $C_1$–$C_{12}$ alkyl; $C_1$–$C_6$ alkyl substituted with halogen, cyano, hydroxy, $C_1$–$C_5$ alkoxy or $C_2$–$C_6$ alkoxycarbonyl; $C_3$–$C_8$ cycloalkyl; cycloalkyl substituted with from one to three members selected from the group consisting of $C_1$–$C_4$ alkyl, halogen and cyano; $C_2$–$C_4$ alkenyl substituted with halogen, hydroxy, $C_2$–$C_4$ alkoxycarbonyl or $C_2$–$C_6$ alkylcarbonyl; phenyl; hydroxy; $C_1$–$C_6$ alkoxy; $C_1$–$C_4$ alkoxy substituted with halogen or $C_2$–$C_6$ alkoxycarbonyl; phenoxy which may or may not be substituted with $C_1$–$C_3$ haloalkyl; benzyloxy; $C_1$–$C_3$ alkylenedioxy formed by two adjacent Xs; pyridyloxy which may or may not be substituted with halogen or $C_1$–$C_3$ haloalkyl; a substituent of the formula, —S(O)$_p$R$^5$ (in which R$^5$ represents $C_1$–$C_6$ alkyl, $C_1$–$C_5$ haloalkyl or phenyl, and p represents an integer of 0, 1 or 2); cyano; formyl; nitro; a substituent of the formula, —COOR$^6$ {in which R$^6$ represents hydrogen; alkali metal; $C_1$–$C_{10}$ alkyl, $C_1$–$C_5$ alkyl substituted with halogen, $C_1$–$C_4$ alkoxy, phenoxy, $C_2$–$C_4$ alkoxycarbonyl or phenoxyphenyl; $C_2$–$C_7$ alkenyl; $C_3$–$C_7$ alkynyl; $C_3$–$C_8$ cycloalkyl; $C_3$–$C_8$ cycloalkyl substituted with $C_1$–$C_3$ alkyl; phenyl; or a substituent of the formula,

(in which R$^7$, R$^8$ and R$^9$, which may be the same or different, represent $C_1$–$C_4$ alkyl or $C_3$–$C_8$ cycloalkyl)}; $C_2$–$C_6$ alkylcarbonyl; $C_2$–$C_6$ alkylcarbonyl substituted with cyano or $C_2$–$C_6$ alkoxycarbonyl; benzoyl which may or may not be substituted with halogen or $C_1$–$C_6$ alkyl; $C_2$–$C_6$ alkylthiocarbonyl; $C_3$–$C_7$ alkoxycarbonylcarbonyl; a substituent of the formula,

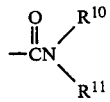

(in which R$^{10}$ and R$^{11}$, which may be the same or different, represent hydrogen, $C_1$–$C_6$ alkyl or phenyl); piperidinocarbonyl; morpholinocarbonyl which may or may not be substituted with one or two $C_1$–$C_4$ alkyls; a substituent of the formula,

(in which R$^{12}$ represents hydrogen or $C_1$–$C_5$ alkyl, and R$^{13}$ represents formyl, $C_2$–$C_{12}$ alkoxycarbonyl, or $C_2$–$C_5$ alkoxycarbonyl substituted with halogen or $C_1$–$C_4$ alkoxy); a substituent of the formula,

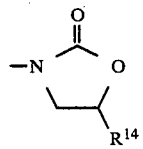

(in which R$^{14}$ represents hydrogen, $C_1$–$C_4$ alkyl or $C_2$–$C_6$ alkoxyalkyl; a substituent of the formula,

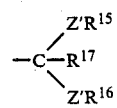

(in which R$^{15}$ and R$^{16}$, which may be the same or different, represent $C_1$–$C_4$ alkyl or, taken together, may form $C_1$–$C_4$ alkylene, R$^{17}$ represents $C_1$–$C_5$ alkyl, cyano or $C_2$–$C_6$ alkoxycarbonyl, and Z$^1$ represents oxygen or sulfur); a substituent of the formula,

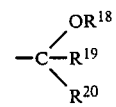

(in which R$^{18}$ represents hydrogen or $C_2$–$C_4$ alkylcarbonyl, and R$^{19}$ and R$^{20}$, which may be the same or different, represent hydrogen or $C_1$–$C_6$ alkyl); a substituent of the formula,

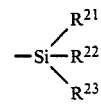

(in which R$^{21}$, R$^{22}$ and R$^{23}$, which may be the same or different, represent $C_1$–$C_4$ alkyl); or a substituent of the formula,

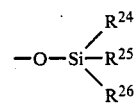

(in which R$^{24}$, R$^{25}$ and R$^{26}$, which may be the same or different, represent $C_1$–$C_4$ alkyl), and n represents an integer of from 1 to 5, and when n represents an integer of from 2 to 5, X may be the same or different]; Y represents hydrogen, $C_1$–$C_6$ alkyl, $C_1$–$C_4$ haloalkyl, halogen, hydroxy, $C_1$–$C_4$ alkoxy, $C_1$–$C_4$ haloalkoxy, $C_1$–$C_3$ alkylenedioxy, phenoxy which may or may not be substituted with trifluoromethyl, a substituent of the formula, —S(O)$_q$R$^{27}$ (in which R$^{27}$ represents $C_1$–$C_3$ alkyl and q represents an integer of 0, 1 or 2), hydroxycarbonyl, $C_2$–$C_5$ alkoxycarbonyl or a substituent of the formula,

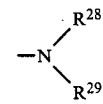

(in which R$^{28}$ and R$^{29}$, which may be the same or different, represent hydrogen, $C_1$–$C_4$ alkyl, or benzyl which may or may not be substituted with $C_2$–$C_6$ alkoxycarbonyl); Z$^1$ represents oxygen or sulfur; Z$^2$ represents oxygen, sulfur or single bond; Q represents $C_1$–$C_8$ alkylene, $C_1$–$C_8$ alkylene substituted with halogen or phenyl, $C_3$–$C_{12}$ alkenylene, $C_3$–$C_{12}$ haloalkenylene or $C_3$–$C_6$ alkynylene; and m represents an integer of from 1 to 3, and when m represents an integer of 2 or 3, Y may be the same or different.

6. An insecticidal and acaricidal composition for use in agriculture and horticulture according to claim 5, wherein R$^1$ represents $C_1$–$C_4$ alkyl; R$^2$ represents $C_1$–$C_4$ alkyl or $C_1$–$C_3$ haloalkyl; R$^3$ represents hydrogen or $C_1$–$C_4$ alkyl; R$^4$ represents a substituent of the formula,

[in which X represents $C_1$-$C_{12}$ alkyl, $C_1$-$C_4$ haloalkyl, $C_5$-$C_7$ cycloalkyl; $C_3$-$C_7$ cycloalkyl substituted with from one to three members selected from the group consisting of $C_1$-$C_3$ alkyl, halogen and cyano; $C_3$-$C_4$ alkoxy; $C_1$-$C_2$ haloalkoxy; 3-chloro-5-trifluoromethylpyridin-2-yloxy; a substituent of the formula, —S(O)$_p$R$^5$ (in which R$^5$ represents $C_2$-$C_4$ alkyl, $C_1$-$C_3$ haloalkyl or phenyl, and p represents an integer of 0, 1 or 2); a substituent of the formula, —COOR$^6$ (in which R$^6$ represents $C_3$-$C_7$ alkyl; $C_4$-$C_6$ haloalkyl; $C_5$-$C_6$ cycloalkyl; or $C_5$-$C_6$ cycloalkyl substituted with $C_1$-$C_3$ alkyl); $C_2$-$C_6$ alkylcarbonyl; $C_2$-$C_6$ alkylthiocarbonyl; $C_3$-$C_9$ N,N-dialkylcarbamoyl; a substituent of the formula,

(in which R$^{12}$ represents $C_1$-$C_5$ alkyl and R$^{13}$ represents $C_2$-$C_{10}$ alkoxycarbonyl or formyl); 1,3-dioxolane-2-yl substituted with $C_1$-$C_4$ alkyl; 1,3-dithiolane-2-yl substituted with $C_1$-$C_4$ alkyl; or trimethylsilyl]; Y represents hydrogen, halogen, $C_1$-$C_4$ alkoxy or $C_1$-$C_4$ haloalkoxy; and Q represents $C_1$-$C_4$ alkylene.

7. An insecticidal and acaricidal composition for use in agriculture and horticulture according to claim 5, wherein R$^1$ represents methyl; R$^2$ represents methyl or trifluoromethyl; R$^3$ represents hydrogen or methyl; R$^4$ represents a substituent of the formula,

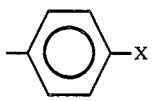

[in which X represents tert-butyl, 2,2-dichloro-1-methylcyclopropyl, 1-cyanocyclopentyl, cyclohexyl, tert-butoxy, 1,1,2,2-tetrafluoroethoxy, 3-chloro-5-trifluoromethylpyridin-2-yloxy, tert-butylthio, heptafluoropropylthio, heptafluoropropylsulfinyl, 1,1,2,2-tetrafluoroethylsulfinyl, a substituent of the formula, —COOR$^6$ (in which R$^6$ represents $C_3$-$C_5$ alkyl, 1,1-dimethyl-2-chloroethyl, cyclohexyl or 1-methylcyclohexyl), tert-butylcarbonyl, tert-butylthiocarbonyl, N,N-diisopropylcarbamoyl, a substituent of the formula,

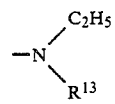

(in which R$^{13}$ represents $C_4$-$C_9$ alkoxycarbonyl or 2-chloroethoxycarbonyl), 2-isopropyl-1,3-dioxolane-2-yl, 2-isopropyl-1,3-dithiolane-2-yl or trimethylsilyl]; Y represents hydrogen or fluorine; Z$^1$ represents oxygen; Z$^2$ represents oxygen or single bond; Q represents $C_1$-$C_2$ alkylene which may have a branched chain; and m represents an integer of 1.

8. An insecticidal and acaricidal composition for use in agriculture and horticulture according to claim 5, wherein R$^1$ represents methyl; R$^2$ represents methyl or trifluoromethyl; R$^3$ represents hydrogen; R$^4$ represents a substituent of the formula,

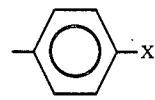

[in which X represents tert-butyl, 2,2-dichloro-1-methylcyclopropyl, 1-cyanocyclopentyl, tert-butoxy, 1,1,2,2-tetrafluoroethoxy, heptafluoropropylthio, heptafluoropropylsulfinyl, a substituent of the formula, —COOR$^6$ (in which R$^6$ represents $C_3$-$C_5$ alkyl, 1,1-dimethyl-2-chloroethyl, cyclohexyl or 1-methylcyclohexyl), tert-butylcarbonyl, N,N-diisopropylcarbamoyl, a substituent of the formula,

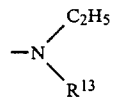

(in which R$^{13}$ represents $C_4$-$C_8$ alkoxycarbonyl), 2-isopropyl-1,3-dioxolane-2-yl, 2-isopropyl-1,3-dithiolane-2-yl or trimethylsilyl]; Y represents hydrogen or fluorine; Z$^1$ represents oxygen; Z$^2$ represents oxygen or single bond; Q represents $C_1$-$C_2$ alkylene which may have a branched chain; and m represents an integer of 1.

* * * * *